(12) United States Patent
Quirk

(10) Patent No.: US 7,547,662 B1
(45) Date of Patent: Jun. 16, 2009

(54) TARGET RECOGNIZING BINDING AGENTS

(75) Inventor: Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 170 days.

(21) Appl. No.: 11/220,245

(22) Filed: Sep. 6, 2005

Related U.S. Application Data

(62) Division of application No. 10/335,181, filed on Dec. 30, 2002, now Pat. No. 6,974,860.

(51) Int. Cl.
| | |
|---|---|
| C40B 50/06 | (2006.01) |
| C12P 21/06 | (2006.01) |
| C40B 40/10 | (2006.01) |
| G01N 33/53 | (2006.01) |
| A61K 38/00 | (2006.01) |
| C12P 21/08 | (2006.01) |
| C07K 16/00 | (2006.01) |

(52) U.S. Cl. .................. 506/26; 506/18; 530/350; 530/324; 435/7.1; 435/69.1; 514/12

(58) Field of Classification Search .................. 506/18, 506/26; 435/7.1, 69.1; 530/324, 387; 514/12
See application file for complete search history.

(56) References Cited

U.S. PATENT DOCUMENTS

| | | | |
|---|---|---|---|
| 6,670,453 B2 | 12/2003 | Frenken et al. | |
| 6,838,254 B1 * | 1/2005 | Hamers et al. | ............ 435/69.1 |
| 7,166,697 B1 * | 1/2007 | Galanis et al. | ............ 530/350 |
| 7,195,866 B2 * | 3/2007 | Griffiths et al. | ............... 435/5 |

OTHER PUBLICATIONS

Decanniere et al., 2001, Degenerate Interfaces in Antigen-Antibody Complexes, Journal of Molecular Biology, 313: 473-478.*
Dumoulin et al., 2002, Single-doamin Antibody Fragments with High Conformational Stability, Protein Science, 11: 500-515.*
Protein Data Bank, retrieved Sep. 11, 2007, citation for 1jtt, www.rcsb.org/pdb/explore/explore.do?structuredId=1JTT, 2 pages.*
Alzari, P. M., et al., "Three-Dimensional Structure of Antibodies", *Annual Review of Immunology*, 6, (1988),555-580.
Arnold, Ulrich , "Kinetic and Thermodynamic Thermal Stabilities of Ribonuclease A and Ribonuclease B", *Biochemistry*, 36(8), (Feb. 25, 1997),2166-2172.
Clark, Matthew , et al., "Validation of the General Purpose Tripos 5.2 Force Field", *Journal of Computational Chemistry*, 10 (8), (1989),982-1012.
Guex, Nicolas , "Swiss-Model and the Swiss-Pdb Viewer: An environment for comparative protein modeling", *Electrophesis*, 18, (1997),2714-2723.
Hamers-Casterman, C. , et al., "Naturally Occuring Antibodies Devoid of Light Chains", *Nature*, 363, (Jun. 3, 1993),446-448.
Higgins, Desmond G., "Clustal V: improved software for multiple sequence alignment", *Computer applications in the biosciences*, 8 (2), (1992), 189-191.
McDonnell, J. M., "Surface Plasmon Resonance: Towards an Understanding of the Mechanisms of Biological Molecular Recognition", *Current Opinion in Chemical Biology*, 5, (Jun. 2001),572-577.
Mulydermans, Serge , "Single domain camel antibodies: current status", *Reviews in Molecular Biotechnology*, 74, (2001),277-302.
Oliphant, Arnold R., et al., "Cloning of random-sequence oligodeoxynucleotides", *Gene*, 44, (1986),177-183.
Pace, C. Nick , "Measuring the conformational stability of a protein", *In Protein Structure: A Practical Approach*, Chapter 13,(1989),311-330.
Peitsch, Manuel C., "Automated Modelling of the Transmembrance Region of G-protein Coupled Receptor by Swiss-Model", *Receptors and Channels*, 4, (1996),161-164.
Peitsch, M. C., "ProMod and Swiss-Model: Internet-based tools for automated comparative protein modelling", *Biochemical Society Transactions*, 24, (1996),274-279.
Sayle, Roger A., "RASMOL: biomolecular graphics for all", *Trends in Biochemical Sciences*, 20, (1995),333-379.
Siegel, Lewis M., "Determination of Molecular Weights and Frictional Ratios of Proteins . . . ", *Biochemica Et Biophysica Acta*, 112, (1966),346-362.
"Supplementary European Search Report for corresponding EP Application No. 03814602.3", (Nov. 20, 2006), 3 pgs.
Claussen, H., et al., "FlexE: Efficient Molecular Docking Considering Protein Structure Variations", *Journal of Molecular Biology*, 308(2), (Apr. 27, 2001), 377-395.

* cited by examiner

*Primary Examiner*—Amber D. Steele
(74) *Attorney, Agent, or Firm*—Armstrong Teasdale LLP

(57) ABSTRACT

The invention is directed to binding agents having binding loops and a stable beta barrel conformation. The binding loops of these agents can easily be altered so that the binding agent can bind any selected target molecule. A variety of methods for generating binding agents with different binding loops are also provided.

5 Claims, 26 Drawing Sheets

```
1          11         21         31         41
ACACACCATA TGGACGTTCA GCTGCAGGCT TCTGGTGGTG GTTCTGTTCA 51         61         71         81         91
GGCTGGTGGT TCTCTGCGTC TGTCTTGCGC TGCTAGCnnn nnnnnnnnn 101        111        121        131        141
nnnnnnnnTG CGCAGGTTGG TTCCGTCAGG CTCCGGGTAA AGAACGTGAA 151        161        171        181        191
GGTGTTGCTG CTATTAATnn nnnnnnnnnn nnnACTAGTT ACGCTGACTC 201        211        221        231        241
TGTTAAAGGT CGTTTCACCA TCTCTCAATT Gnnnnnnnnn nnnAACGTTT 251        261        271        281        291
ACCTGCTGAT GAACTCTCTG GAACCGGAAG ACACCGCTAT CTACTACTGC 301        311        321        331        341
GCTGCTGGCC ACnnnnnnnn nnnnnnnnnn nnCACGTGCG GTCACGGTCT 351        361        371        381        391
GAGTACTnnn nnnnnnnnnn nnnnnCCATG GGGTCAGGGT ACCCAGGTTA 401        411        421
CCGTTTCTTC TTAGATATCA CAC
```

FIG. 2

```
1          11         21         31         41
MDVQLQASGG GSVQAGGSLR LSCAASxxxx xxxCAGWFRQ APGKEREGVA (ii)                  (iii)
51         61         71         81         91
AINxxxxxTS YADSVKGRFT ISQLxxxxNV YLLMNSLEPE DTAIYYCAAG (iv)         (v)
101        111        121        131
HxxxxxxxxC GHGLSTxxxx xxPWGQGTQV TVSS
```

FIG. 3

```
1            11           21           31           41
ACACACCATA   TGGACGTTCA   GCTGCAGGCT   TCTGGTGGTG   GTTCTGTTCA 51           61           71           81           91
GGCTGGTGGT   TCTCTGCGTC   TGTCTTGCGC   TGCTAGCGCT   GGTGCTGCTG 101          111          121          131          141
GTGCTGCTTG   CGCAGGTTGG   TTCCGTCAGG   CTCCGGGTAA   AGAACGTGAA 151          161          171          181          191
GGTGTTGCTG   CTATTAATGC   TGGTGCTGCT   GGTACTAGTT   ACGCTGACTC 201          211          221          231          241
TGTTAAAGGT   CGTTTCACCA   TCTCTCAATT   GGCTGGTGCT   GCTAACGTTT 251          261          271          281          291
ACCTGCTGAT   GAACTCTCTG   GAACCGGAAG   ACACCGCTAT   CTACTACTGC 301          311          321          331          341
GCTGCTGGCC   ACGCTGGTGC   TGCTGGTGCT   GCCACGTGCG   GTCACGGTCT 351          361          371          381          391
GAGTACTGCT   GGTGCTGCTG   GTGCTCCATG   GGGTCAGGGT   ACCCAGGTTA 401          411          421
CCGTTTCTTC   TTAGATATCA   CAC
```

FIG. 4

```
                                      (i)
1            11           21           31           41
MDVQLQASGG   GSVQAGGSLR   LSCAASAGAA   GAACAGWFRQ   APGKEREGVA (ii)                    (iii)
51           61           71           81           91
AINAGAAGTS   YADSVKGRFT   ISQLAGAANV   YLLMNSLEPE   DTAIYYCAAG (iv)          (v)
101          111          121          131
HAGAAGAATC   GHGLSTAGAA   GAPWGQGTQV   TVSS
```

FIG. 5

```
REMARK      Generic Binding reagent
REMARK      SEQ ID NO:38

SEQRES    1    132   VAL GLN LEU GLN ALA SER GLY GLY GLY SER VAL GLN ALA
SEQRES    2    132   GLY GLY SER LEU ARG LEU SER CYS ALA ALA SER ALA GLY
SEQRES    3    132   ALA ALA GLY ALA ALA CYS ALA GLY TRP PHE ARG GLN ALA
SEQRES    4    132   PRO GLY LYS GLU ARG GLU GLY VAL ALA ALA ILE ASN ALA
SEQRES    5    132   GLY ALA ALA GLY THR SER TYR ALA ASP SER VAL LYS GLY
SEQRES    6    132   ARG PHE THR ILE SER GLN LEU ALA GLY ALA ALA ASN VAL
SEQRES    7    132   TYR LEU LEU MET ASN SER LEU GLU PRO GLU ASP THR ALA
SEQRES    8    132   ILE TYR TYR CYS ALA ALA GLY HIS ALA GLY ALA ALA GLY
SEQRES    9    132   ALA ALA THR CYS GLY HIS GLY LEU SER THR ALA GLY ALA
SEQRES   10    132   ALA GLY ALA PRO TRP GLY GLN GLY THR GLN VAL THR VAL
SEQRES   11    132   SER SER
CRYST1     1.000     1.000     1.000  90.00   90.00   90.00 P 1           1
ORIGX1       1.000000  0.000000  0.000000        0.00000
ORIGX2       0.000000  1.000000  0.000000        0.00000
ORIGX3       0.000000  0.000000  1.000000        0.00000
SCALE1       1.000000  0.000000  0.000000        0.00000
SCALE2       0.000000  1.000000  0.000000        0.00000
SCALE3       0.000000  0.000000  1.000000        0.00000
ATOM       1   N    VAL     3      66.585  51.191  31.477  1.00 10.00
ATOM       2   CA   VAL     3      66.737  51.193  30.006  1.00 10.00
ATOM       3   C    VAL     3      66.940  52.625  29.475  1.00 10.00
ATOM       4   O    VAL     3      66.271  53.562  29.907  1.00 10.00
ATOM       5   CB   VAL     3      65.527  50.541  29.317  1.00 10.00
ATOM       6   CG1  VAL     3      65.733  50.530  27.797  1.00 10.00
ATOM       7   CG2  VAL     3      65.291  49.109  29.816  1.00 10.00
ATOM       8   N    GLN     4      67.867  52.734  28.532  1.00 10.00
ATOM       9   CA   GLN     4      68.182  54.005  27.863  1.00 10.00
ATOM      10   C    GLN     4      68.347  53.814  26.357  1.00 10.00
ATOM      11   O    GLN     4      68.847  52.777  25.920  1.00 10.00
ATOM      12   CB   GLN     4      69.467  54.589  28.459  1.00 10.00
ATOM      13   CG   GLN     4      69.295  55.005  29.927  1.00 10.00
ATOM      14   CD   GLN     4      68.226  56.086  30.139  1.00 10.00
ATOM      15   OE1  GLN     4      67.680  56.694  29.227  1.00 10.00
ATOM      16   NE2  GLN     4      67.946  56.375  31.390  1.00 10.00
ATOM      17   N    LEU     5      67.887  54.814  25.613  1.00 10.00
ATOM      18   CA   LEU     5      68.062  54.859  24.151  1.00 10.00
ATOM      19   C    LEU     5      68.836  56.103  23.730  1.00 10.00
ATOM      20   O    LEU     5      68.367  57.232  23.878  1.00 10.00
ATOM      21   CB   LEU     5      66.725  54.777  23.401  1.00 10.00
ATOM      22   CG   LEU     5      65.960  53.469  23.642  1.00 10.00
ATOM      23   CD1  LEU     5      64.735  53.410  22.734  1.00 10.00
ATOM      24   CD2  LEU     5      66.820  52.242  23.360  1.00 10.00
ATOM      25   N    GLN     6      70.057  55.841  23.287  1.00 10.00
ATOM      26   CA   GLN     6      71.002  56.888  22.874  1.00 10.00
ATOM      27   C    GLN     6      71.068  56.973  21.349  1.00 10.00
ATOM      28   O    GLN     6      71.514  56.030  20.694  1.00 10.00
ATOM      29   CB   GLN     6      72.393  56.588  23.443  1.00 10.00
ATOM      30   CG   GLN     6      72.426  56.658  24.975  1.00 10.00
ATOM      31   CD   GLN     6      72.096  58.048  25.535  1.00 10.00
```

FIG. 12A

| ATOM | 32 | OE1 | GLN | 6 | 71.909 | 59.044 | 24.850 | 1.00 | 10.00 |
|------|----|-----|-----|---|--------|--------|--------|------|-------|
| ATOM | 33 | NE2 | GLN | 6 | 72.024 | 58.126 | 26.843 | 1.00 | 10.00 |
| ATOM | 34 | N   | ALA | 7 | 70.498 | 58.053 | 20.829 | 1.00 | 10.00 |
| ATOM | 35 | CA  | ALA | 7 | 70.470 | 58.307 | 19.378 | 1.00 | 10.00 |
| ATOM | 36 | C   | ALA | 7 | 71.535 | 59.345 | 19.001 | 1.00 | 10.00 |
| ATOM | 37 | O   | ALA | 7 | 71.851 | 60.246 | 19.779 | 1.00 | 10.00 |
| ATOM | 38 | CB  | ALA | 7 | 69.084 | 58.808 | 18.965 | 1.00 | 10.00 |
| ATOM | 39 | N   | SER | 8 | 72.145 | 59.115 | 17.850 | 1.00 | 10.00 |
| ATOM | 40 | CA  | SER | 8 | 73.180 | 60.012 | 17.304 | 1.00 | 10.00 |
| ATOM | 41 | C   | SER | 8 | 73.058 | 60.098 | 15.776 | 1.00 | 10.00 |
| ATOM | 42 | O   | SER | 8 | 72.334 | 59.326 | 15.140 | 1.00 | 10.00 |
| ATOM | 43 | CB  | SER | 8 | 74.589 | 59.559 | 17.723 | 1.00 | 10.00 |
| ATOM | 44 | OG  | SER | 8 | 74.918 | 58.375 | 17.009 | 1.00 | 10.00 |
| ATOM | 45 | N   | GLY | 9 | 73.716 | 61.134 | 15.250 | 1.00 | 10.00 |
| ATOM | 46 | CA  | GLY | 9 | 73.710 | 61.452 | 13.813 | 1.00 | 10.00 |
| ATOM | 47 | C   | GLY | 9 | 72.764 | 62.633 | 13.578 | 1.00 | 10.00 |
| ATOM | 48 | O   | GLY | 9 | 72.472 | 63.403 | 14.494 | 1.00 | 10.00 |
| ATOM | 49 | N   | GLY | 10 | 72.251 | 62.690 | 12.346 | 1.00 | 10.00 |
| ATOM | 50 | CA  | GLY | 10 | 71.296 | 63.739 | 11.948 | 1.00 | 10.00 |
| ATOM | 51 | C   | GLY | 10 | 71.977 | 65.101 | 11.965 | 1.00 | 10.00 |
| ATOM | 52 | O   | GLY | 10 | 73.148 | 65.236 | 12.320 | 1.00 | 10.00 |
| ATOM | 53 | N   | GLY | 11 | 71.224 | 66.060 | 11.446 | 1.00 | 10.00 |
| ATOM | 54 | CA  | GLY | 11 | 71.723 | 67.431 | 11.273 | 1.00 | 10.00 |
| ATOM | 55 | C   | GLY | 11 | 71.069 | 68.014 | 10.024 | 1.00 | 10.00 |
| ATOM | 56 | O   | GLY | 11 | 69.924 | 67.694 | 9.710  | 1.00 | 10.00 |
| ATOM | 57 | N   | SER | 12 | 71.834 | 68.822 | 9.313  | 1.00 | 10.00 |
| ATOM | 58 | CA  | SER | 12 | 71.363 | 69.438 | 8.060  | 1.00 | 10.00 |
| ATOM | 59 | C   | SER | 12 | 72.107 | 68.842 | 6.861  | 1.00 | 10.00 |
| ATOM | 60 | O   | SER | 12 | 73.262 | 68.428 | 6.957  | 1.00 | 10.00 |
| ATOM | 61 | CB  | SER | 12 | 71.565 | 70.953 | 8.093  | 1.00 | 10.00 |
| ATOM | 62 | OG  | SER | 12 | 72.959 | 71.252 | 8.206  | 1.00 | 10.00 |
| ATOM | 63 | N   | VAL | 13 | 71.398 | 68.814 | 5.744  | 1.00 | 10.00 |
| ATOM | 64 | CA  | VAL | 13 | 71.900 | 68.267 | 4.471  | 1.00 | 10.00 |
| ATOM | 65 | C   | VAL | 13 | 71.092 | 68.871 | 3.315  | 1.00 | 10.00 |
| ATOM | 66 | O   | VAL | 13 | 69.914 | 69.202 | 3.452  | 1.00 | 10.00 |
| ATOM | 67 | CB  | VAL | 13 | 71.822 | 66.723 | 4.493  | 1.00 | 10.00 |
| ATOM | 68 | CG1 | VAL | 13 | 70.392 | 66.204 | 4.676  | 1.00 | 10.00 |
| ATOM | 69 | CG2 | VAL | 13 | 72.476 | 66.082 | 3.264  | 1.00 | 10.00 |
| ATOM | 70 | N   | GLN | 14 | 71.780 | 69.017 | 2.195  | 1.00 | 10.00 |
| ATOM | 71 | CA  | GLN | 14 | 71.137 | 69.412 | 0.933  | 1.00 | 10.00 |
| ATOM | 72 | C   | GLN | 14 | 70.237 | 68.283 | 0.427  | 1.00 | 10.00 |
| ATOM | 73 | O   | GLN | 14 | 70.570 | 67.105 | 0.580  | 1.00 | 10.00 |
| ATOM | 74 | CB  | GLN | 14 | 72.219 | 69.727 | -0.102 | 1.00 | 10.00 |
| ATOM | 75 | CG  | GLN | 14 | 72.979 | 71.008 | 0.260  | 1.00 | 10.00 |
| ATOM | 76 | CD  | GLN | 14 | 72.087 | 72.257 | 0.289  | 1.00 | 10.00 |
| ATOM | 77 | OE1 | GLN | 14 | 70.907 | 72.273 | -0.037 | 1.00 | 10.00 |
| ATOM | 78 | NE2 | GLN | 14 | 72.656 | 73.350 | 0.741  | 1.00 | 10.00 |
| ATOM | 79 | N   | ALA | 15 | 69.102 | 68.660 | -0.154 | 1.00 | 10.00 |
| ATOM | 80 | CA  | ALA | 15 | 68.192 | 67.697 | -0.804 | 1.00 | 10.00 |
| ATOM | 81 | C   | ALA | 15 | 68.978 | 66.844 | -1.812 | 1.00 | 10.00 |
| ATOM | 82 | O   | ALA | 15 | 69.923 | 67.327 | -2.434 | 1.00 | 10.00 |
| ATOM | 83 | CB  | ALA | 15 | 67.068 | 68.429 | -1.540 | 1.00 | 10.00 |
| ATOM | 84 | N   | GLY | 16 | 68.710 | 65.541 | -1.756 | 1.00 | 10.00 |
| ATOM | 85 | CA  | GLY | 16 | 69.421 | 64.536 | -2.564 | 1.00 | 10.00 |
| ATOM | 86 | C   | GLY | 16 | 70.616 | 63.927 | -1.814 | 1.00 | 10.00 |
| ATOM | 87 | O   | GLY | 16 | 71.227 | 62.976 | -2.296 | 1.00 | 10.00 |

FIG. 12B

```
ATOM   88  N    GLY  17     70.934  64.510  -0.648  1.00 10.00
ATOM   89  CA   GLY  17     72.033  64.042   0.208  1.00 10.00
ATOM   90  C    GLY  17     71.604  62.814   1.020  1.00 10.00
ATOM   91  O    GLY  17     70.485  62.309   0.891  1.00 10.00
ATOM   92  N    SER  18     72.505  62.438   1.914  1.00 10.00
ATOM   93  CA   SER  18     72.298  61.278   2.797  1.00 10.00
ATOM   94  C    SER  18     72.742  61.568   4.228  1.00 10.00
ATOM   95  O    SER  18     73.640  62.376   4.470  1.00 10.00
ATOM   96  CB   SER  18     73.045  60.047   2.271  1.00 10.00
ATOM   97  OG   SER  18     72.564  59.710   0.967  1.00 10.00
ATOM   98  N    LEU  19     72.024  60.939   5.147  1.00 10.00
ATOM   99  CA   LEU  19     72.348  60.928   6.582  1.00 10.00
ATOM  100  C    LEU  19     72.188  59.530   7.171  1.00 10.00
ATOM  101  O    LEU  19     71.490  58.685   6.612  1.00 10.00
ATOM  102  CB   LEU  19     71.506  61.930   7.383  1.00 10.00
ATOM  103  CG   LEU  19     72.072  63.355   7.327  1.00 10.00
ATOM  104  CD1  LEU  19     71.197  64.284   8.167  1.00 10.00
ATOM  105  CD2  LEU  19     73.519  63.419   7.834  1.00 10.00
ATOM  106  N    ARG  20     72.911  59.289   8.254  1.00 10.00
ATOM  107  CA   ARG  20     72.827  57.999   8.948  1.00 10.00
ATOM  108  C    ARG  20     72.591  58.233  10.436  1.00 10.00
ATOM  109  O    ARG  20     73.387  58.890  11.108  1.00 10.00
ATOM  110  CB   ARG  20     74.122  57.225   8.756  1.00 10.00
ATOM  111  CG   ARG  20     73.880  55.729   8.973  1.00 10.00
ATOM  112  CD   ARG  20     75.161  54.910   8.817  1.00 10.00
ATOM  113  NE   ARG  20     75.932  55.312   7.619  1.00 10.00
ATOM  114  CZ   ARG  20     77.256  55.433   7.565  1.00 10.00
ATOM  115  NH1  ARG  20     78.001  55.161   8.629  1.00 10.00
ATOM  116  NH2  ARG  20     77.854  55.848   6.455  1.00 10.00
ATOM  117  N    LEU  21     71.431  57.773  10.869  1.00 10.00
ATOM  118  CA   LEU  21     71.074  57.821  12.291  1.00 10.00

ATOM  119  C    LEU  21     71.355  56.483  12.954  1.00 10.00
ATOM  120  O    LEU  21     71.276  55.432  12.319  1.00 10.00
ATOM  121  CB   LEU  21     69.602  58.204  12.468  1.00 10.00
ATOM  122  CG   LEU  21     69.286  59.612  11.958  1.00 10.00
ATOM  123  CD1  LEU  21     67.876  60.050  12.339  1.00 10.00
ATOM  124  CD2  LEU  21     70.220  60.597  12.622  1.00 10.00
ATOM  125  N    SER  22     71.771  56.572  14.199  1.00 10.00
ATOM  126  CA   SER  22     72.048  55.373  15.000  1.00 10.00
ATOM  127  C    SER  22     71.357  55.504  16.351  1.00 10.00
ATOM  128  O    SER  22     70.998  56.599  16.789  1.00 10.00
ATOM  129  CB   SER  22     73.547  55.200  15.209  1.00 10.00
ATOM  130  OG   SER  22     73.977  56.271  16.011  1.00 10.00
ATOM  131  N    CYS  23     71.162  54.349  16.961  1.00 10.00
ATOM  132  CA   CYS  23     70.453  54.258  18.240  1.00 10.00
ATOM  133  C    CYS  23     70.902  53.003  18.977  1.00 10.00
ATOM  134  O    CYS  23     70.736  51.891  18.477  1.00 10.00
ATOM  135  CB   CYS  23     68.949  54.208  17.975  1.00 10.00
ATOM  136  SG   CYS  23     67.962  54.160  19.511  1.00 10.00
ATOM  137  N    ALA  24     71.461  53.236  20.152  1.00 10.00
ATOM  138  CA   ALA  24     71.942  52.158  21.027  1.00 10.00
ATOM  139  C    ALA  24     71.003  52.034  22.229  1.00 10.00
ATOM  140  O    ALA  24     70.631  53.032  22.853  1.00 10.00
ATOM  141  CB   ALA  24     73.365  52.471  21.496  1.00 10.00
ATOM  142  N    ALA  25     70.602  50.794  22.478  1.00 10.00
ATOM  143  CA   ALA  25     69.757  50.444  23.629  1.00 10.00
```

FIG. 12C

```
ATOM  144  C   ALA  25   70.653  49.919  24.747  1.00  10.00
ATOM  145  O   ALA  25   71.562  49.120  24.528  1.00  10.00
ATOM  146  CB  ALA  25   68.747  49.363  23.238  1.00  10.00
ATOM  147  N   SER  26   70.452  50.480  25.925  1.00  10.00
ATOM  148  CA  SER  26   71.251  50.125  27.110  1.00  10.00
ATOM  149  C   SER  26   70.324  49.716  28.245  1.00  10.00
ATOM  150  O   SER  26   69.171  50.151  28.285  1.00  10.00
ATOM  151  CB  SER  26   72.111  51.314  27.544  1.00  10.00
ATOM  152  OG  SER  26   72.993  51.665  26.476  1.00  10.00
ATOM  153  N   ALA  27   70.857  48.883  29.142  1.00  10.00
ATOM  154  CA  ALA  27   70.150  48.348  30.329  1.00  10.00
ATOM  155  C   ALA  27   69.063  47.308  29.984  1.00  10.00
ATOM  156  O   ALA  27   68.098  47.104  30.724  1.00  10.00
ATOM  157  CB  ALA  27   69.593  49.486  31.206  1.00  50.00
ATOM  158  N   GLY  28   69.307  46.570  28.893  1.00  10.00
ATOM  159  CA  GLY  28   68.426  45.466  28.476  1.00  10.00
ATOM  160  C   GLY  28   69.107  44.128  28.787  1.00  10.00
ATOM  161  O   GLY  28   70.273  43.932  28.453  1.00  10.00
ATOM  162  N   ALA  29   68.383  43.289  29.518  1.00  10.00
ATOM  163  CA  ALA  29   68.831  41.909  29.808  1.00  10.00
ATOM  164  C   ALA  29   68.451  40.996  28.632  1.00  10.00
ATOM  165  O   ALA  29   69.262  40.235  28.113  1.00  10.00
ATOM  166  CB  ALA  29   68.190  41.413  31.108  1.00  50.00
ATOM  167  N   ALA  30   67.196  41.148  28.215  1.00  10.00
ATOM  168  CA  ALA  30   66.626  40.498  27.029  1.00  10.00
ATOM  169  C   ALA  30   65.824  41.539  26.247  1.00  10.00
ATOM  170  O   ALA  30   65.140  42.388  26.829  1.00  10.00
ATOM  171  CB  ALA  30   65.713  39.350  27.463  1.00  50.00
ATOM  172  N   GLY  31   65.998  41.465  24.927  1.00  10.00
ATOM  173  CA  GLY  31   65.350  42.389  23.995  1.00  10.00
ATOM  174  C   GLY  31   66.193  43.663  23.777  1.00  10.00
ATOM  175  O   GLY  31   67.394  43.671  24.033  1.00  10.00
ATOM  176  N   ALA  32   65.582  44.753  23.320  1.00  10.00
ATOM  177  CA  ALA  32   64.146  44.868  22.974  1.00  10.00
ATOM  178  C   ALA  32   63.755  43.961  21.795  1.00  10.00
ATOM  179  O   ALA  32   64.617  43.466  21.077  1.00  10.00
ATOM  180  CB  ALA  32   63.820  46.319  22.631  1.00  50.00
ATOM  181  N   ALA  33   62.474  43.624  21.738  1.00  10.00
ATOM  182  CA  ALA  33   61.915  42.814  20.634  1.00  10.00

ATOM  183  C   ALA  33   61.840  43.616  19.325  1.00  10.00
ATOM  184  O   ALA  33   62.004  43.083  18.229  1.00  10.00
ATOM  185  CB  ALA  33   60.516  42.331  21.010  1.00  50.00
ATOM  186  N   CYS  34   61.538  44.902  19.471  1.00  10.00
ATOM  187  CA  CYS  34   61.412  45.836  18.343  1.00  10.00
ATOM  188  C   CYS  34   62.227  47.103  18.585  1.00  10.00
ATOM  189  O   CYS  34   62.340  47.558  19.720  1.00  10.00
ATOM  190  CB  CYS  34   59.943  46.227  18.174  1.00  10.00
ATOM  191  SG  CYS  34   58.894  44.820  17.670  1.00  10.00
ATOM  192  N   ALA  35   62.802  47.596  17.502  1.00  10.00
ATOM  193  CA  ALA  35   63.445  48.918  17.452  1.00  10.00
ATOM  194  C   ALA  35   63.068  49.555  16.113  1.00  10.00
ATOM  195  O   ALA  35   62.999  48.863  15.094  1.00  10.00
ATOM  196  CB  ALA  35   64.962  48.766  17.556  1.00  50.00
ATOM  197  N   GLY  36   62.700  50.831  16.186  1.00  10.00
ATOM  198  CA  GLY  36   62.293  51.583  14.993  1.00  10.00
ATOM  199  C   GLY  36   62.538  53.081  15.153  1.00  10.00
```

FIG. 12D

| ATOM | 200 | O   | GLY | 36 | 63.047 | 53.544 | 16.175 | 1.00 | 10.00 |
| ATOM | 201 | N   | TRP | 37 | 62.106 | 53.789 | 14.125 | 1.00 | 10.00 |
| ATOM | 202 | CA  | TRP | 37 | 62.222 | 55.248 | 14.045 | 1.00 | 10.00 |
| ATOM | 203 | C   | TRP | 37 | 60.867 | 55.859 | 13.711 | 1.00 | 10.00 |
| ATOM | 204 | O   | TRP | 37 | 60.129 | 55.357 | 12.861 | 1.00 | 10.00 |
| ATOM | 205 | CB  | TRP | 37 | 63.237 | 55.638 | 12.970 | 1.00 | 10.00 |
| ATOM | 206 | CG  | TRP | 37 | 64.663 | 55.256 | 13.371 | 1.00 | 10.00 |
| ATOM | 207 | CD1 | TRP | 37 | 65.258 | 54.083 | 13.163 | 1.00 | 10.00 |
| ATOM | 208 | CD2 | TRP | 37 | 65.589 | 56.091 | 13.976 | 1.00 | 10.00 |
| ATOM | 209 | NE1 | TRP | 37 | 66.519 | 54.144 | 13.592 | 1.00 | 10.00 |
| ATOM | 210 | CE2 | TRP | 37 | 66.756 | 55.353 | 14.096 | 1.00 | 10.00 |
| ATOM | 211 | CE3 | TRP | 37 | 65.537 | 57.410 | 14.408 | 1.00 | 10.00 |
| ATOM | 212 | CZ2 | TRP | 37 | 67.887 | 55.936 | 14.653 | 1.00 | 10.00 |
| ATOM | 213 | CZ3 | TRP | 37 | 66.672 | 57.997 | 14.953 | 1.00 | 10.00 |
| ATOM | 214 | CH2 | TRP | 37 | 67.845 | 57.260 | 15.078 | 1.00 | 10.00 |
| ATOM | 215 | N   | PHE | 38 | 60.557 | 56.890 | 14.469 | 1.00 | 10.00 |
| ATOM | 216 | CA  | PHE | 38 | 59.366 | 57.726 | 14.263 | 1.00 | 10.00 |
| ATOM | 217 | C   | PHE | 38 | 59.851 | 59.160 | 14.058 | 1.00 | 10.00 |
| ATOM | 218 | O   | PHE | 38 | 60.934 | 59.524 | 14.501 | 1.00 | 10.00 |
| ATOM | 219 | CB  | PHE | 38 | 58.456 | 57.654 | 15.489 | 1.00 | 10.00 |
| ATOM | 220 | CG  | PHE | 38 | 57.988 | 56.219 | 15.737 | 1.00 | 10.00 |
| ATOM | 221 | CD1 | PHE | 38 | 58.765 | 55.357 | 16.501 | 1.00 | 10.00 |
| ATOM | 222 | CD2 | PHE | 38 | 56.789 | 55.781 | 15.196 | 1.00 | 10.00 |
| ATOM | 223 | CE1 | PHE | 38 | 58.339 | 54.054 | 16.721 | 1.00 | 10.00 |
| ATOM | 224 | CE2 | PHE | 38 | 56.361 | 54.480 | 15.419 | 1.00 | 10.00 |
| ATOM | 225 | CZ  | PHE | 38 | 57.137 | 53.616 | 16.184 | 1.00 | 10.00 |
| ATOM | 226 | N   | ARG | 39 | 59.103 | 59.918 | 13.286 | 1.00 | 10.00 |
| ATOM | 227 | CA  | ARG | 39 | 59.462 | 61.314 | 13.004 | 1.00 | 10.00 |
| ATOM | 228 | C   | ARG | 39 | 58.227 | 62.194 | 13.157 | 1.00 | 10.00 |
| ATOM | 229 | O   | ARG | 39 | 57.103 | 61.782 | 12.858 | 1.00 | 10.00 |
| ATOM | 230 | CB  | ARG | 39 | 60.062 | 61.464 | 11.604 | 1.00 | 10.00 |
| ATOM | 231 | CG  | ARG | 39 | 59.033 | 61.188 | 10.506 | 1.00 | 10.00 |
| ATOM | 232 | CD  | ARG | 39 | 59.637 | 61.476 | 9.147 | 1.00 | 10.00 |
| ATOM | 233 | NE  | ARG | 39 | 58.621 | 61.221 | 8.113 | 1.00 | 10.00 |
| ATOM | 234 | CZ  | ARG | 39 | 58.837 | 61.345 | 6.807 | 1.00 | 10.00 |
| ATOM | 235 | NH1 | ARG | 39 | 60.019 | 61.741 | 6.355 | 1.00 | 10.00 |
| ATOM | 236 | NH2 | ARG | 39 | 57.884 | 61.042 | 5.937 | 1.00 | 10.00 |
| ATOM | 237 | N   | GLN | 40 | 58.495 | 63.406 | 13.593 | 1.00 | 10.00 |
| ATOM | 238 | CA  | GLN | 40 | 57.442 | 64.403 | 13.752 | 1.00 | 10.00 |
| ATOM | 239 | C   | GLN | 40 | 57.880 | 65.670 | 13.012 | 1.00 | 10.00 |
| ATOM | 240 | O   | GLN | 40 | 58.803 | 66.368 | 13.441 | 1.00 | 10.00 |
| ATOM | 241 | CB  | GLN | 40 | 57.233 | 64.627 | 15.254 | 1.00 | 10.00 |
| ATOM | 242 | CG  | GLN | 40 | 55.809 | 65.054 | 15.598 | 1.00 | 10.00 |
| ATOM | 243 | CD  | GLN | 40 | 55.357 | 66.337 | 14.867 | 1.00 | 10.00 |
| ATOM | 244 | OE1 | GLN | 40 | 56.096 | 67.127 | 14.335 | 1.00 | 10.00 |
| ATOM | 245 | NE2 | GLN | 40 | 54.119 | 66.641 | 15.027 | 1.00 | 10.00 |
| ATOM | 246 | N   | ALA | 41 | 57.240 | 65.883 | 11.863 | 1.00 | 10.00 |
| ATOM | 247 | CA  | ALA | 41 | 57.396 | 67.123 | 11.087 | 1.00 | 10.00 |
| ATOM | 248 | C   | ALA | 41 | 56.501 | 68.246 | 11.650 | 1.00 | 10.00 |
| ATOM | 249 | O   | ALA | 41 | 55.348 | 67.984 | 12.011 | 1.00 | 10.00 |
| ATOM | 250 | CB  | ALA | 41 | 57.052 | 66.853 | 9.618 | 1.00 | 10.00 |
| ATOM | 251 | N   | PRO | 42 | 56.962 | 69.505 | 11.577 | 1.00 | 10.00 |
| ATOM | 252 | CA  | PRO | 42 | 56.224 | 70.674 | 12.098 | 1.00 | 10.00 |
| ATOM | 253 | C   | PRO | 42 | 54.804 | 70.714 | 11.512 | 1.00 | 10.00 |
| ATOM | 254 | O   | PRO | 42 | 54.626 | 70.595 | 10.302 | 1.00 | 10.00 |
| ATOM | 255 | CB  | PRO | 42 | 56.999 | 71.889 | 11.590 | 1.00 | 10.00 |

FIG. 12E

| | | | | | | | | |
|---|---|---|---|---|---|---|---|---|
| ATOM | 256 | CG | PRO | 42 | 58.424 | 71.371 | 11.411 | 1.00 10.00 |
| ATOM | 257 | CD | PRO | 42 | 58.231 | 69.930 | 10.949 | 1.00 10.00 |
| ATOM | 258 | N | GLY | 43 | 53.822 | 70.741 | 12.421 | 1.00 10.00 |
| ATOM | 259 | CA | GLY | 43 | 52.388 | 70.810 | 12.066 | 1.00 10.00 |
| ATOM | 260 | C | GLY | 43 | 51.783 | 69.523 | 11.470 | 1.00 10.00 |
| ATOM | 261 | O | GLY | 43 | 50.607 | 69.511 | 11.114 | 1.00 10.00 |
| ATOM | 262 | N | LYS | 44 | 52.539 | 68.430 | 11.486 | 1.00 10.00 |
| ATOM | 263 | CA | LYS | 44 | 52.057 | 67.133 | 10.971 | 1.00 10.00 |
| ATOM | 264 | C | LYS | 44 | 51.934 | 66.101 | 12.097 | 1.00 10.00 |
| ATOM | 265 | O | LYS | 44 | 52.306 | 66.381 | 13.216 | 1.00 10.00 |
| ATOM | 266 | CB | LYS | 44 | 52.992 | 66.586 | 9.896 | 1.00 10.00 |
| ATOM | 267 | CG | LYS | 44 | 53.007 | 67.517 | 8.687 | 1.00 10.00 |
| ATOM | 268 | CD | LYS | 44 | 53.689 | 66.830 | 7.511 | 1.00 10.00 |
| ATOM | 269 | CE | LYS | 44 | 53.714 | 67.768 | 6.308 | 1.00 10.00 |
| ATOM | 270 | NZ | LYS | 44 | 54.153 | 67.038 | 5.113 | 1.00 10.00 |
| ATOM | 271 | N | GLU | 45 | 51.192 | 65.042 | 11.872 | 1.00 10.00 |
| ATOM | 272 | CA | GLU | 45 | 51.086 | 63.939 | 12.851 | 1.00 10.00 |
| ATOM | 273 | C | GLU | 45 | 52.397 | 63.143 | 12.901 | 1.00 10.00 |
| ATOM | 274 | O | GLU | 45 | 53.095 | 63.040 | 11.892 | 1.00 10.00 |
| ATOM | 275 | CB | GLU | 45 | 49.913 | 63.036 | 12.469 | 1.00 10.00 |
| ATOM | 276 | CG | GLU | 45 | 48.576 | 63.786 | 12.543 | 1.00 10.00 |
| ATOM | 277 | CD | GLU | 45 | 48.244 | 64.210 | 13.977 | 1.00 10.00 |
| ATOM | 278 | OE1 | GLU | 45 | 48.728 | 65.288 | 14.387 | 1.00 10.00 |
| ATOM | 279 | OE2 | GLU | 45 | 47.565 | 63.408 | 14.649 | 1.00 10.00 |
| ATOM | 280 | N | ARG | 46 | 52.719 | 62.607 | 14.075 | 1.00 10.00 |
| ATOM | 281 | CA | ARG | 46 | 53.894 | 61.726 | 14.216 | 1.00 10.00 |
| ATOM | 282 | C | ARG | 46 | 53.699 | 60.504 | 13.302 | 1.00 10.00 |
| ATOM | 283 | O | ARG | 46 | 52.618 | 59.916 | 13.253 | 1.00 10.00 |
| ATOM | 284 | CB | ARG | 46 | 54.031 | 61.267 | 15.665 | 1.00 10.00 |
| ATOM | 285 | CG | ARG | 46 | 55.350 | 60.514 | 15.863 | 1.00 10.00 |
| ATOM | 286 | CD | ARG | 46 | 55.448 | 59.922 | 17.262 | 1.00 10.00 |
| ATOM | 287 | NE | ARG | 46 | 54.435 | 58.869 | 17.451 | 1.00 10.00 |
| ATOM | 288 | CZ | ARG | 46 | 54.296 | 58.142 | 18.557 | 1.00 10.00 |
| ATOM | 289 | NH1 | ARG | 46 | 55.054 | 58.354 | 19.623 | 1.00 10.00 |
| ATOM | 290 | NH2 | ARG | 46 | 53.436 | 57.155 | 18.595 | 1.00 10.00 |
| ATOM | 291 | N | GLU | 47 | 54.757 | 60.159 | 12.588 | 1.00 10.00 |
| ATOM | 292 | CA | GLU | 47 | 54.701 | 59.065 | 11.609 | 1.00 10.00 |
| ATOM | 293 | C | GLU | 47 | 55.831 | 58.067 | 11.895 | 1.00 10.00 |
| ATOM | 294 | O | GLU | 47 | 56.971 | 58.459 | 12.133 | 1.00 10.00 |
| ATOM | 295 | CB | GLU | 47 | 54.831 | 59.733 | 10.232 | 1.00 10.00 |
| ATOM | 296 | CG | GLU | 47 | 54.388 | 58.924 | 9.011 | 1.00 10.00 |
| ATOM | 297 | CD | GLU | 47 | 55.219 | 57.665 | 8.782 | 1.00 10.00 |
| ATOM | 298 | OE1 | GLU | 47 | 56.247 | 57.768 | 8.072 | 1.00 10.00 |
| ATOM | 299 | OE2 | GLU | 47 | 54.698 | 56.645 | 9.262 | 1.00 10.00 |
| ATOM | 300 | N | GLY | 48 | 55.467 | 56.776 | 11.869 | 1.00 10.00 |
| ATOM | 301 | CA | GLY | 48 | 56.437 | 55.673 | 11.834 | 1.00 10.00 |
| ATOM | 302 | C | GLY | 48 | 57.262 | 55.612 | 10.537 | 1.00 10.00 |
| ATOM | 303 | O | GLY | 48 | 56.751 | 55.337 | 9.441 | 1.00 10.00 |
| ATOM | 304 | N | VAL | 49 | 58.557 | 55.536 | 10.664 | 1.00 10.00 |
| ATOM | 305 | CA | VAL | 49 | 59.436 | 55.575 | 9.472 | 1.00 10.00 |
| ATOM | 306 | C | VAL | 49 | 59.846 | 54.160 | 9.053 | 1.00 10.00 |
| ATOM | 307 | O | VAL | 49 | 59.669 | 53.745 | 7.907 | 1.00 10.00 |
| ATOM | 308 | CB | VAL | 49 | 60.647 | 56.482 | 9.725 | 1.00 10.00 |
| ATOM | 309 | CG1 | VAL | 49 | 61.608 | 56.533 | 8.531 | 1.00 10.00 |
| ATOM | 310 | CG2 | VAL | 49 | 60.176 | 57.904 | 10.019 | 1.00 10.00 |
| ATOM | 311 | N | ALA | 50 | 60.398 | 53.448 | 10.024 | 1.00 10.00 |

FIG. 12F

| ATOM | 312 | CA  | ALA | 50 | 60.986 | 52.118 | 9.810  | 1.00 | 10.00 |
| ATOM | 313 | C   | ALA | 50 | 61.139 | 51.410 | 11.152 | 1.00 | 10.00 |
| ATOM | 314 | O   | ALA | 50 | 61.271 | 52.059 | 12.185 | 1.00 | 10.00 |
| ATOM | 315 | CB  | ALA | 50 | 62.368 | 52.261 | 9.174  | 1.00 | 10.00 |
| ATOM | 316 | N   | ALA | 51 | 60.958 | 50.103 | 11.099 | 1.00 | 10.00 |
| ATOM | 317 | CA  | ALA | 51 | 61.074 | 49.212 | 12.265 | 1.00 | 10.00 |
| ATOM | 318 | C   | ALA | 51 | 61.749 | 47.907 | 11.837 | 1.00 | 10.00 |
| ATOM | 319 | O   | ALA | 51 | 61.771 | 47.567 | 10.651 | 1.00 | 10.00 |
| ATOM | 320 | CB  | ALA | 51 | 59.687 | 48.925 | 12.849 | 1.00 | 10.00 |
| ATOM | 321 | N   | ILE | 52 | 62.328 | 47.238 | 12.820 | 1.00 | 10.00 |
| ATOM | 322 | CA  | ILE | 52 | 63.017 | 45.954 | 12.620 | 1.00 | 10.00 |
| ATOM | 323 | C   | ILE | 52 | 62.717 | 45.037 | 13.812 | 1.00 | 10.00 |
| ATOM | 324 | O   | ILE | 52 | 62.761 | 45.458 | 14.972 | 1.00 | 10.00 |
| ATOM | 325 | CB  | ILE | 52 | 64.531 | 46.186 | 12.418 | 1.00 | 10.00 |
| ATOM | 326 | CG1 | ILE | 52 | 65.212 | 44.884 | 11.960 | 1.00 | 10.00 |
| ATOM | 327 | CG2 | ILE | 52 | 65.203 | 46.809 | 13.658 | 1.00 | 10.00 |
| ATOM | 328 | CD1 | ILE | 52 | 66.690 | 45.032 | 11.572 | 1.00 | 10.00 |
| ATOM | 329 | N   | ASN | 53 | 62.392 | 43.798 | 13.481 | 1.00 | 10.00 |
| ATOM | 330 | CA  | ASN | 53 | 62.243 | 42.744 | 14.496 | 1.00 | 10.00 |
| ATOM | 331 | C   | ASN | 53 | 63.627 | 42.339 | 15.000 | 1.00 | 10.00 |
| ATOM | 332 | O   | ASN | 53 | 64.392 | 41.709 | 14.267 | 1.00 | 10.00 |
| ATOM | 333 | CB  | ASN | 53 | 61.504 | 41.535 | 13.921 | 1.00 | 10.00 |
| ATOM | 334 | CG  | ASN | 53 | 60.070 | 41.885 | 13.526 | 1.00 | 10.00 |
| ATOM | 335 | OD1 | ASN | 53 | 59.724 | 42.092 | 12.370 | 1.00 | 10.00 |
| ATOM | 336 | ND2 | ASN | 53 | 59.228 | 42.001 | 14.520 | 1.00 | 10.00 |
| ATOM | 337 | N   | ALA | 54 | 63.973 | 42.804 | 16.198 | 1.00 | 10.00 |
| ATOM | 338 | CA  | ALA | 54 | 65.242 | 42.408 | 16.833 | 1.00 | 10.00 |
| ATOM | 339 | C   | ALA | 54 | 65.286 | 40.874 | 16.933 | 1.00 | 10.00 |
| ATOM | 340 | O   | ALA | 54 | 64.292 | 40.243 | 17.293 | 1.00 | 10.00 |
| ATOM | 341 | CB  | ALA | 54 | 65.357 | 43.020 | 18.224 | 1.00 | 50.00 |
| ATOM | 342 | N   | GLY | 55 | 66.307 | 40.327 | 16.270 | 1.00 | 10.00 |
| ATOM | 343 | CA  | GLY | 55 | 66.450 | 38.862 | 16.152 | 1.00 | 10.00 |
| ATOM | 344 | C   | GLY | 55 | 66.135 | 38.400 | 14.726 | 1.00 | 10.00 |
| ATOM | 345 | O   | GLY | 55 | 67.050 | 38.243 | 13.923 | 1.00 | 10.00 |
| ATOM | 346 | N   | ALA | 56 | 64.838 | 38.334 | 14.417 | 1.00 | 10.00 |
| ATOM | 347 | CA  | ALA | 56 | 64.342 | 37.897 | 13.092 | 1.00 | 10.00 |
| ATOM | 348 | C   | ALA | 56 | 64.953 | 38.689 | 11.927 | 1.00 | 10.00 |
| ATOM | 349 | O   | ALA | 56 | 65.124 | 38.142 | 10.841 | 1.00 | 10.00 |
| ATOM | 350 | CB  | ALA | 56 | 62.815 | 38.005 | 13.031 | 1.00 | 50.00 |
| ATOM | 351 | N   | ALA | 57 | 65.283 | 39.960 | 12.191 | 1.00 | 10.00 |
| ATOM | 352 | CA  | ALA | 57 | 65.875 | 40.919 | 11.232 | 1.00 | 10.00 |
| ATOM | 353 | C   | ALA | 57 | 64.898 | 41.387 | 10.140 | 1.00 | 10.00 |
| ATOM | 354 | O   | ALA | 57 | 65.274 | 42.166 | 9.262  | 1.00 | 10.00 |
| ATOM | 355 | CB  | ALA | 57 | 67.162 | 40.364 | 10.596 | 1.00 | 50.00 |
| ATOM | 356 | N   | GLY | 58 | 63.612 | 41.023 | 10.291 | 1.00 | 10.00 |
| ATOM | 357 | CA  | GLY | 58 | 62.542 | 41.472 | 9.382  | 1.00 | 10.00 |
| ATOM | 358 | C   | GLY | 58 | 62.402 | 42.997 | 9.492  | 1.00 | 10.00 |
| ATOM | 359 | O   | GLY | 58 | 62.437 | 43.544 | 10.595 | 1.00 | 10.00 |
| ATOM | 360 | N   | THR | 59 | 62.246 | 43.642 | 8.344  | 1.00 | 10.00 |
| ATOM | 361 | CA  | THR | 59 | 62.196 | 45.119 | 8.278  | 1.00 | 10.00 |
| ATOM | 362 | C   | THR | 59 | 60.856 | 45.596 | 7.712  | 1.00 | 10.00 |
| ATOM | 363 | O   | THR | 59 | 60.164 | 44.890 | 6.977  | 1.00 | 10.00 |
| ATOM | 364 | CB  | THR | 59 | 63.331 | 45.691 | 7.417  | 1.00 | 10.00 |
| ATOM | 365 | OG1 | THR | 59 | 63.154 | 45.275 | 6.059  | 1.00 | 10.00 |
| ATOM | 366 | CG2 | THR | 59 | 64.717 | 45.292 | 7.935  | 1.00 | 10.00 |
| ATOM | 367 | N   | SER | 60 | 60.448 | 46.758 | 8.192  | 1.00 | 10.00 |
| ATOM | 368 | CA  | SER | 60 | 59.205 | 47.419 | 7.750  | 1.00 | 10.00 |

FIG. 12G

| | | | | | | | | | |
|---|---|---|---|---|---|---|---|---|---|
| ATOM | 369 | C | SER | 60 | 59.485 | 48.902 | 7.521 | 1.00 | 10.00 |
| ATOM | 370 | O | SER | 60 | 60.288 | 49.494 | 8.244 | 1.00 | 10.00 |
| ATOM | 371 | CB | SER | 60 | 58.119 | 47.266 | 8.817 | 1.00 | 10.00 |
| ATOM | 372 | OG | SER | 60 | 57.883 | 45.875 | 9.062 | 1.00 | 10.00 |
| ATOM | 373 | N | TYR | 61 | 58.846 | 49.451 | 6.496 | 1.00 | 10.00 |
| ATOM | 374 | CA | TYR | 61 | 59.027 | 50.871 | 6.139 | 1.00 | 10.00 |
| ATOM | 375 | C | TYR | 61 | 57.691 | 51.526 | 5.804 | 1.00 | 10.00 |
| ATOM | 376 | O | TYR | 61 | 56.804 | 50.890 | 5.236 | 1.00 | 10.00 |
| ATOM | 377 | CB | TYR | 61 | 59.964 | 50.997 | 4.935 | 1.00 | 10.00 |
| ATOM | 378 | CG | TYR | 61 | 61.375 | 50.514 | 5.270 | 1.00 | 10.00 |
| ATOM | 379 | CD1 | TYR | 61 | 62.270 | 51.392 | 5.862 | 1.00 | 10.00 |
| ATOM | 380 | CD2 | TYR | 61 | 61.735 | 49.200 | 5.000 | 1.00 | 10.00 |
| ATOM | 381 | CE1 | TYR | 61 | 63.546 | 50.955 | 6.188 | 1.00 | 10.00 |
| ATOM | 382 | CE2 | TYR | 61 | 63.005 | 48.759 | 5.325 | 1.00 | 10.00 |
| ATOM | 383 | CZ | TYR | 61 | 63.899 | 49.636 | 5.908 | 1.00 | 10.00 |
| ATOM | 384 | OH | TYR | 61 | 65.152 | 49.180 | 6.091 | 1.00 | 10.00 |
| ATOM | 385 | N | ALA | 62 | 57.560 | 52.786 | 6.200 | 1.00 | 10.00 |
| ATOM | 386 | CA | ALA | 62 | 56.440 | 53.624 | 5.734 | 1.00 | 10.00 |
| ATOM | 387 | C | ALA | 62 | 56.543 | 53.743 | 4.206 | 1.00 | 10.00 |
| ATOM | 388 | O | ALA | 62 | 57.636 | 53.792 | 3.640 | 1.00 | 10.00 |
| ATOM | 389 | CB | ALA | 62 | 56.527 | 55.015 | 6.361 | 1.00 | 10.00 |
| ATOM | 390 | N | ASP | 63 | 55.397 | 53.844 | 3.545 | 1.00 | 10.00 |
| ATOM | 391 | CA | ASP | 63 | 55.363 | 53.934 | 2.069 | 1.00 | 10.00 |
| ATOM | 392 | C | ASP | 63 | 56.151 | 55.133 | 1.521 | 1.00 | 10.00 |
| ATOM | 393 | O | ASP | 63 | 56.869 | 55.004 | 0.535 | 1.00 | 10.00 |
| ATOM | 394 | CB | ASP | 63 | 53.927 | 54.004 | 1.552 | 1.00 | 10.00 |
| ATOM | 395 | CG | ASP | 63 | 53.181 | 52.688 | 1.771 | 1.00 | 10.00 |
| ATOM | 396 | OD1 | ASP | 63 | 53.685 | 51.652 | 1.299 | 1.00 | 10.00 |
| ATOM | 397 | OD2 | ASP | 63 | 52.131 | 52.757 | 2.445 | 1.00 | 10.00 |
| ATOM | 398 | N | SER | 64 | 56.127 | 56.219 | 2.291 | 1.00 | 10.00 |
| ATOM | 399 | CA | SER | 64 | 56.830 | 57.475 | 1.960 | 1.00 | 10.00 |
| ATOM | 400 | C | SER | 64 | 58.362 | 57.343 | 1.923 | 1.00 | 10.00 |
| ATOM | 401 | O | SER | 64 | 59.038 | 58.198 | 1.360 | 1.00 | 10.00 |
| ATOM | 402 | CB | SER | 64 | 56.458 | 58.576 | 2.958 | 1.00 | 10.00 |
| ATOM | 403 | OG | SER | 64 | 56.811 | 58.177 | 4.287 | 1.00 | 10.00 |
| ATOM | 404 | N | VAL | 65 | 58.872 | 56.297 | 2.565 | 1.00 | 10.00 |
| ATOM | 405 | CA | VAL | 65 | 60.318 | 56.104 | 2.771 | 1.00 | 10.00 |
| ATOM | 406 | C | VAL | 65 | 60.901 | 54.864 | 2.069 | 1.00 | 10.00 |
| ATOM | 407 | O | VAL | 65 | 62.122 | 54.702 | 1.991 | 1.00 | 10.00 |
| ATOM | 408 | CB | VAL | 65 | 60.646 | 56.112 | 4.278 | 1.00 | 10.00 |
| ATOM | 409 | CG1 | VAL | 65 | 60.279 | 57.447 | 4.936 | 1.00 | 10.00 |
| ATOM | 410 | CG2 | VAL | 65 | 60.060 | 54.933 | 5.051 | 1.00 | 10.00 |
| ATOM | 411 | N | LYS | 66 | 60.019 | 53.955 | 1.651 | 1.00 | 10.00 |
| ATOM | 412 | CA | LYS | 66 | 60.411 | 52.699 | 0.985 | 1.00 | 10.00 |
| ATOM | 413 | C | LYS | 66 | 61.312 | 52.970 | -0.226 | 1.00 | 10.00 |
| ATOM | 414 | O | LYS | 66 | 61.077 | 53.902 | -0.993 | 1.00 | 10.00 |
| ATOM | 415 | CB | LYS | 66 | 59.182 | 51.932 | 0.496 | 1.00 | 10.00 |
| ATOM | 416 | CG | LYS | 66 | 58.327 | 51.430 | 1.656 | 1.00 | 10.00 |
| ATOM | 417 | CD | LYS | 66 | 57.151 | 50.611 | 1.134 | 1.00 | 10.00 |
| ATOM | 418 | CE | LYS | 66 | 56.336 | 50.064 | 2.302 | 1.00 | 10.00 |
| ATOM | 419 | NZ | LYS | 66 | 55.216 | 49.250 | 1.817 | 1.00 | 10.00 |
| ATOM | 420 | N | GLY | 67 | 62.434 | 52.247 | -0.229 | 1.00 | 10.00 |
| ATOM | 421 | CA | GLY | 67 | 63.433 | 52.353 | -1.313 | 1.00 | 10.00 |
| ATOM | 422 | C | GLY | 67 | 64.533 | 53.383 | -1.016 | 1.00 | 10.00 |
| ATOM | 423 | O | GLY | 67 | 65.668 | 53.227 | -1.455 | 1.00 | 10.00 |
| ATOM | 424 | N | ARG | 68 | 64.193 | 54.367 | -0.196 | 1.00 | 10.00 |

FIG. 12H

```
ATOM    425  CA   ARG   68      65.107  55.459   0.134  1.00 10.00
ATOM    426  C    ARG   68      65.879  55.212   1.449  1.00 10.00
ATOM    427  O    ARG   68      67.096  55.396   1.524  1.00 10.00
ATOM    428  CB   ARG   68      64.221  56.701   0.161  1.00 10.00
ATOM    429  CG   ARG   68      65.146  57.846   0.480  1.00 10.00
ATOM    430  CD   ARG   68      64.576  59.244   0.351  1.00 10.00
ATOM    431  NE   ARG   68      63.613  59.478   1.408  1.00 10.00
ATOM    432  CZ   ARG   68      62.484  60.145   1.236  1.00 10.00
ATOM    433  NH1  ARG   68      62.234  60.741   0.081  1.00 10.00
ATOM    434  NH2  ARG   68      61.516  60.117   2.124  1.00 10.00
ATOM    435  N    PHE   69      65.134  54.794   2.462  1.00 10.00
ATOM    436  CA   PHE   69      65.690  54.500   3.793  1.00 10.00
ATOM    437  C    PHE   69      65.895  53.001   3.979  1.00 10.00
ATOM    438  O    PHE   69      65.214  52.169   3.377  1.00 10.00
ATOM    439  CB   PHE   69      64.751  55.000   4.890  1.00 10.00
ATOM    440  CG   PHE   69      64.585  56.508   4.787  1.00 10.00
ATOM    441  CD1  PHE   69      63.604  57.052   4.001  1.00 10.00
ATOM    442  CD2  PHE   69      65.411  57.373   5.473  1.00 10.00
ATOM    443  CE1  PHE   69      63.421  58.415   3.944  1.00 10.00
ATOM    444  CE2  PHE   69      65.226  58.745   5.346  1.00 10.00
ATOM    445  CZ   PHE   69      64.234  59.300   4.601  1.00 10.00
ATOM    446  N    THR   70      66.920  52.701   4.761  1.00 10.00
ATOM    447  CA   THR   70      67.280  51.326   5.135  1.00 10.00
ATOM    448  C    THR   70      67.646  51.319   6.631  1.00 10.00
ATOM    449  O    THR   70      68.503  52.067   7.074  1.00 10.00
ATOM    450  CB   THR   70      68.455  50.823   4.282  1.00 10.00
ATOM    451  OG1  THR   70      68.116  50.917   2.892  1.00 10.00
ATOM    452  CG2  THR   70      68.850  49.377   4.610  1.00 10.00
ATOM    453  N    ILE   71      66.971  50.455   7.361  1.00 10.00
ATOM    454  CA   ILE   71      67.180  50.137   8.766  1.00 10.00
ATOM    455  C    ILE   71      67.963  48.813   8.835  1.00 10.00
ATOM    456  O    ILE   71      67.735  47.884   8.059  1.00 10.00
ATOM    457  CB   ILE   71      65.836  50.060   9.531  1.00 10.00
ATOM    458  CG1  ILE   71      66.097  50.071  11.044  1.00 10.00
ATOM    459  CG2  ILE   71      64.953  48.863   9.125  1.00 10.00
ATOM    460  CD1  ILE   71      64.837  50.174  11.915  1.00 10.00
ATOM    461  N    SER   72      68.815  48.754   9.836  1.00 10.00
ATOM    462  CA   SER   72      69.662  47.579  10.092  1.00 10.00
ATOM    463  C    SER   72      70.073  47.563  11.562  1.00 10.00
ATOM    464  O    SER   72      70.028  48.582  12.249  1.00 10.00
ATOM    465  CB   SER   72      70.914  47.614   9.208  1.00 10.00
ATOM    466  OG   SER   72      71.722  48.749   9.534  1.00 10.00
ATOM    467  N    GLN   73      70.402  46.373  12.028  1.00 10.00
ATOM    468  CA   GLN   73      70.854  46.191  13.412  1.00 10.00
ATOM    469  C    GLN   73      72.350  45.841  13.430  1.00 10.00
ATOM    470  O    GLN   73      72.945  45.352  12.474  1.00 10.00
ATOM    471  CB   GLN   73      69.922  45.158  14.081  1.00 10.00
ATOM    472  CG   GLN   73      70.532  43.902  14.723  1.00 10.00
ATOM    473  CD   GLN   73      71.429  43.092  13.757  1.00 10.00
ATOM    474  OE1  GLN   73      71.349  43.198  12.547  1.00 10.00
ATOM    475  NE2  GLN   73      72.378  42.355  14.276  1.00 10.00
ATOM    476  N    LEU   74      72.895  45.999  14.618  1.00 10.00
ATOM    477  CA   LEU   74      74.228  45.475  14.930  1.00 10.00
ATOM    478  C    LEU   74      74.088  44.738  16.265  1.00 10.00
ATOM    479  O    LEU   74      74.687  45.156  17.249  1.00 10.00
ATOM    480  CB   LEU   74      75.149  46.703  14.945  1.00 10.00
```

FIG. 12I

| | | | | | | | | |
|---|---|---|---|---|---|---|---|---|
| ATOM | 481 | CG | LEU | 74 | 76.669 | 46.508 | 14.928 | 1.00 10.00 |
| ATOM | 482 | CD1 | LEU | 74 | 77.304 | 47.895 | 14.872 | 1.00 10.00 |
| ATOM | 483 | CD2 | LEU | 74 | 77.269 | 45.765 | 16.127 | 1.00 10.00 |
| ATOM | 484 | N | ALA | 75 | 73.241 | 43.717 | 16.315 | 1.00 12.50 |
| ATOM | 485 | CA | ALA | 75 | 72.768 | 42.927 | 17.477 | 1.00 12.50 |
| ATOM | 486 | C | ALA | 75 | 73.569 | 43.042 | 18.795 | 1.00 12.50 |
| ATOM | 487 | O | ALA | 75 | 72.981 | 43.375 | 19.813 | 1.00 12.50 |
| ATOM | 488 | CB | ALA | 75 | 72.638 | 41.431 | 17.177 | 1.00 50.00 |
| ATOM | 489 | N | GLY | 76 | 74.895 | 43.048 | 18.621 | 1.00 10.00 |
| ATOM | 490 | CA | GLY | 76 | 75.893 | 43.254 | 19.683 | 1.00 10.00 |
| ATOM | 491 | C | GLY | 76 | 75.479 | 44.348 | 20.676 | 1.00 10.00 |
| ATOM | 492 | O | GLY | 76 | 74.997 | 44.019 | 21.759 | 1.00 10.00 |
| ATOM | 493 | N | ALA | 77 | 75.494 | 45.611 | 20.245 | 1.00 12.50 |
| ATOM | 494 | CA | ALA | 77 | 75.162 | 46.739 | 21.135 | 1.00 12.50 |
| ATOM | 495 | C | ALA | 77 | 73.664 | 47.082 | 21.193 | 1.00 12.50 |
| ATOM | 496 | O | ALA | 77 | 73.293 | 48.197 | 21.571 | 1.00 12.50 |
| ATOM | 497 | CB | ALA | 77 | 75.987 | 47.956 | 20.692 | 1.00 50.00 |
| ATOM | 498 | N | ALA | 78 | 72.793 | 46.143 | 20.784 | 1.00 10.00 |
| ATOM | 499 | CA | ALA | 78 | 71.333 | 46.383 | 20.693 | 1.00 10.00 |
| ATOM | 500 | C | ALA | 78 | 71.032 | 47.735 | 19.999 | 1.00 10.00 |
| ATOM | 501 | O | ALA | 78 | 70.313 | 48.611 | 20.474 | 1.00 10.00 |
| ATOM | 502 | CB | ALA | 78 | 70.717 | 46.295 | 22.098 | 1.00 50.00 |
| ATOM | 503 | N | ASN | 79 | 71.843 | 47.965 | 18.981 | 1.00 10.00 |
| ATOM | 504 | CA | ASN | 79 | 71.921 | 49.233 | 18.230 | 1.00 10.00 |
| ATOM | 505 | C | ASN | 79 | 71.427 | 49.022 | 16.795 | 1.00 10.00 |
| ATOM | 506 | O | ASN | 79 | 71.587 | 47.958 | 16.188 | 1.00 10.00 |
| ATOM | 507 | CB | ASN | 79 | 73.367 | 49.774 | 18.230 | 1.00 50.00 |
| ATOM | 508 | CG | ASN | 79 | 74.377 | 48.807 | 17.594 | 1.00 50.00 |
| ATOM | 509 | OD1 | ASN | 79 | 75.472 | 49.116 | 17.155 | 1.00 50.00 |
| ATOM | 510 | ND2 | ASN | 79 | 73.940 | 47.589 | 17.489 | 1.00 50.00 |
| ATOM | 511 | N | VAL | 80 | 70.709 | 50.022 | 16.351 | 1.00 10.00 |
| ATOM | 512 | CA | VAL | 80 | 70.106 | 50.033 | 15.010 | 1.00 10.00 |
| ATOM | 513 | C | VAL | 80 | 70.570 | 51.287 | 14.262 | 1.00 10.00 |
| ATOM | 514 | O | VAL | 80 | 70.834 | 52.319 | 14.879 | 1.00 10.00 |
| ATOM | 515 | CB | VAL | 80 | 68.571 | 49.945 | 15.104 | 1.00 10.00 |
| ATOM | 516 | CG1 | VAL | 80 | 68.142 | 48.629 | 15.764 | 1.00 10.00 |
| ATOM | 517 | CG2 | VAL | 80 | 67.942 | 51.140 | 15.837 | 1.00 10.00 |
| ATOM | 518 | N | TYR | 81 | 70.638 | 51.161 | 12.951 | 1.00 10.00 |
| ATOM | 519 | CA | TYR | 81 | 71.002 | 52.279 | 12.070 | 1.00 10.00 |
| ATOM | 520 | C | TYR | 81 | 69.907 | 52.532 | 11.039 | 1.00 10.00 |
| ATOM | 521 | O | TYR | 81 | 69.210 | 51.611 | 10.612 | 1.00 10.00 |
| ATOM | 522 | CB | TYR | 81 | 72.328 | 51.994 | 11.363 | 1.00 10.00 |
| ATOM | 523 | CG | TYR | 81 | 73.475 | 51.913 | 12.370 | 1.00 10.00 |
| ATOM | 524 | CD1 | TYR | 81 | 74.118 | 53.073 | 12.771 | 1.00 10.00 |
| ATOM | 525 | CD2 | TYR | 81 | 73.865 | 50.685 | 12.889 | 1.00 10.00 |
| ATOM | 526 | CE1 | TYR | 81 | 75.156 | 53.003 | 13.691 | 1.00 10.00 |
| ATOM | 527 | CE2 | TYR | 81 | 74.895 | 50.619 | 13.817 | 1.00 10.00 |
| ATOM | 528 | CZ | TYR | 81 | 75.539 | 51.781 | 14.221 | 1.00 10.00 |
| ATOM | 529 | OH | TYR | 81 | 76.543 | 51.733 | 15.132 | 1.00 10.00 |
| ATOM | 530 | N | LEU | 82 | 69.739 | 53.810 | 10.739 | 1.00 10.00 |
| ATOM | 531 | CA | LEU | 82 | 68.798 | 54.265 | 9.715 | 1.00 10.00 |
| ATOM | 532 | C | LEU | 82 | 69.542 | 55.084 | 8.659 | 1.00 10.00 |
| ATOM | 533 | O | LEU | 82 | 69.954 | 56.219 | 8.906 | 1.00 10.00 |
| ATOM | 534 | CB | LEU | 82 | 67.666 | 55.075 | 10.355 | 1.00 10.00 |
| ATOM | 535 | CG | LEU | 82 | 66.458 | 55.168 | 9.417 | 1.00 10.00 |
| ATOM | 536 | CD1 | LEU | 82 | 65.833 | 53.790 | 9.184 | 1.00 10.00 |

FIG. 12J

| | | | | | | | | | |
|---|---|---|---|---|---|---|---|---|---|
| ATOM | 537 | CD2 | LEU | 82 | 65.420 | 56.133 | 9.987 | 1.00 | 10.00 |
| ATOM | 538 | N | LEU | 83 | 69.864 | 54.396 | 7.572 | 1.00 | 10.00 |
| ATOM | 539 | CA | LEU | 83 | 70.549 | 55.008 | 6.429 | 1.00 | 10.00 |
| ATOM | 540 | C | LEU | 83 | 69.513 | 55.695 | 5.531 | 1.00 | 10.00 |
| ATOM | 541 | O | LEU | 83 | 68.582 | 55.061 | 5.039 | 1.00 | 10.00 |
| ATOM | 542 | CB | LEU | 83 | 71.325 | 53.944 | 5.647 | 1.00 | 10.00 |
| ATOM | 543 | CG | LEU | 83 | 72.346 | 54.574 | 4.692 | 1.00 | 10.00 |
| ATOM | 544 | CD1 | LEU | 83 | 73.449 | 55.309 | 5.453 | 1.00 | 10.00 |
| ATOM | 545 | CD2 | LEU | 83 | 72.973 | 53.500 | 3.807 | 1.00 | 10.00 |
| ATOM | 546 | N | MET | 84 | 69.677 | 56.999 | 5.417 | 1.00 | 10.00 |
| ATOM | 547 | CA | MET | 84 | 68.711 | 57.870 | 4.730 | 1.00 | 10.00 |
| ATOM | 548 | C | MET | 84 | 69.351 | 58.431 | 3.440 | 1.00 | 10.00 |
| ATOM | 549 | O | MET | 84 | 70.221 | 59.288 | 3.537 | 1.00 | 10.00 |
| ATOM | 550 | CB | MET | 84 | 68.376 | 59.000 | 5.707 | 1.00 | 10.00 |
| ATOM | 551 | CG | MET | 84 | 67.921 | 58.554 | 7.122 | 1.00 | 10.00 |
| ATOM | 552 | SD | MET | 84 | 66.667 | 59.581 | 7.984 | 1.00 | 10.00 |
| ATOM | 553 | CE | MET | 84 | 67.511 | 61.142 | 7.939 | 1.00 | 10.00 |
| ATOM | 554 | N | ASN | 85 | 68.993 | 57.857 | 2.298 | 1.00 | 10.00 |
| ATOM | 555 | CA | ASN | 85 | 69.506 | 58.308 | 0.975 | 1.00 | 10.00 |
| ATOM | 556 | C | ASN | 85 | 68.459 | 59.162 | 0.261 | 1.00 | 10.00 |
| ATOM | 557 | O | ASN | 85 | 67.414 | 59.346 | 0.873 | 1.00 | 10.00 |
| ATOM | 558 | CB | ASN | 85 | 69.852 | 57.111 | 0.093 | 1.00 | 10.00 |
| ATOM | 559 | CG | ASN | 85 | 71.054 | 56.383 | 0.679 | 1.00 | 10.00 |
| ATOM | 560 | OD1 | ASN | 85 | 72.189 | 56.844 | 0.634 | 1.00 | 10.00 |
| ATOM | 561 | ND2 | ASN | 85 | 70.785 | 55.256 | 1.302 | 1.00 | 10.00 |
| ATOM | 562 | N | SER | 86 | 68.801 | 59.953 | -0.743 | 1.00 | 10.00 |
| ATOM | 563 | CA | SER | 86 | 67.824 | 60.760 | -1.518 | 1.00 | 10.00 |
| ATOM | 564 | C | SER | 86 | 66.896 | 61.628 | -0.640 | 1.00 | 10.00 |
| ATOM | 565 | O | SER | 86 | 65.686 | 61.740 | -0.855 | 1.00 | 10.00 |
| ATOM | 566 | CB | SER | 86 | 66.965 | 59.875 | -2.439 | 1.00 | 10.00 |
| ATOM | 567 | OG | SER | 86 | 67.780 | 59.221 | -3.409 | 1.00 | 10.00 |
| ATOM | 568 | N | LEU | 87 | 67.500 | 62.266 | 0.360 | 1.00 | 10.00 |
| ATOM | 569 | CA | LEU | 87 | 66.742 | 63.100 | 1.298 | 1.00 | 10.00 |
| ATOM | 570 | C | LEU | 87 | 66.099 | 64.271 | 0.592 | 1.00 | 10.00 |
| ATOM | 571 | O | LEU | 87 | 66.721 | 65.037 | -0.131 | 1.00 | 10.00 |
| ATOM | 572 | CB | LEU | 87 | 67.593 | 63.611 | 2.461 | 1.00 | 10.00 |
| ATOM | 573 | CG | LEU | 87 | 68.039 | 62.477 | 3.388 | 1.00 | 10.00 |
| ATOM | 574 | CD1 | LEU | 87 | 68.721 | 63.063 | 4.620 | 1.00 | 10.00 |
| ATOM | 575 | CD2 | LEU | 87 | 66.865 | 61.597 | 3.825 | 1.00 | 10.00 |
| ATOM | 576 | N | GLU | 88 | 64.817 | 64.377 | 0.819 | 1.00 | 10.00 |
| ATOM | 577 | CA | GLU | 88 | 64.025 | 65.430 | 0.223 | 1.00 | 10.00 |
| ATOM | 578 | C | GLU | 88 | 63.580 | 66.390 | 1.358 | 1.00 | 10.00 |
| ATOM | 579 | O | GLU | 88 | 63.465 | 65.955 | 2.505 | 1.00 | 10.00 |
| ATOM | 580 | CB | GLU | 88 | 62.937 | 64.629 | -0.524 | 1.00 | 10.00 |
| ATOM | 581 | CG | GLU | 88 | 63.251 | 63.876 | -1.808 | 1.00 | 10.00 |
| ATOM | 582 | CD | GLU | 88 | 63.792 | 64.848 | -2.853 | 1.00 | 10.00 |
| ATOM | 583 | OE1 | GLU | 88 | 65.006 | 65.114 | -2.761 | 1.00 | 10.00 |
| ATOM | 584 | OE2 | GLU | 88 | 62.970 | 65.365 | -3.640 | 1.00 | 10.00 |
| ATOM | 585 | N | PRO | 89 | 63.260 | 67.670 | 1.077 | 1.00 | 10.00 |
| ATOM | 586 | CA | PRO | 89 | 62.864 | 68.702 | 2.062 | 1.00 | 10.00 |
| ATOM | 587 | C | PRO | 89 | 61.757 | 68.294 | 3.067 | 1.00 | 10.00 |
| ATOM | 588 | O | PRO | 89 | 61.806 | 68.594 | 4.257 | 1.00 | 10.00 |
| ATOM | 589 | CB | PRO | 89 | 62.333 | 69.860 | 1.221 | 1.00 | 10.00 |
| ATOM | 590 | CG | PRO | 89 | 63.059 | 69.709 | -0.114 | 1.00 | 10.00 |
| ATOM | 591 | CD | PRO | 89 | 63.167 | 68.202 | -0.301 | 1.00 | 10.00 |
| ATOM | 592 | N | GLU | 90 | 60.765 | 67.562 | 2.620 | 1.00 | 10.00 |

FIG. 12K

| ATOM | 593 | CA | GLU | 90 | 59.667 | 66.922 | 3.319 | 1.00 | 10.00 |
| ATOM | 594 | C | GLU | 90 | 60.149 | 65.914 | 4.393 | 1.00 | 10.00 |
| ATOM | 595 | O | GLU | 90 | 59.399 | 65.583 | 5.298 | 1.00 | 10.00 |
| ATOM | 596 | CB | GLU | 90 | 58.647 | 66.207 | 2.394 | 1.00 | 10.00 |
| ATOM | 597 | CG | GLU | 90 | 59.133 | 65.060 | 1.490 | 1.00 | 10.00 |
| ATOM | 598 | CD | GLU | 90 | 59.942 | 65.609 | 0.318 | 1.00 | 10.00 |
| ATOM | 599 | OE1 | GLU | 90 | 61.029 | 66.044 | 0.633 | 1.00 | 10.00 |
| ATOM | 600 | OE2 | GLU | 90 | 59.434 | 65.823 | -0.800 | 1.00 | 10.00 |
| ATOM | 601 | N | ASP | 91 | 61.355 | 65.394 | 4.197 | 1.00 | 10.00 |
| ATOM | 602 | CA | ASP | 91 | 62.022 | 64.546 | 5.203 | 1.00 | 10.00 |
| ATOM | 603 | C | ASP | 91 | 62.442 | 65.354 | 6.440 | 1.00 | 10.00 |
| ATOM | 604 | O | ASP | 91 | 62.687 | 64.768 | 7.481 | 1.00 | 10.00 |
| ATOM | 605 | CB | ASP | 91 | 63.224 | 63.810 | 4.608 | 1.00 | 10.00 |
| ATOM | 606 | CG | ASP | 91 | 62.733 | 62.803 | 3.575 | 1.00 | 10.00 |
| ATOM | 607 | OD1 | ASP | 91 | 61.785 | 62.084 | 3.947 | 1.00 | 10.00 |
| ATOM | 608 | OD2 | ASP | 91 | 63.190 | 62.899 | 2.416 | 1.00 | 10.00 |
| ATOM | 609 | N | THR | 92 | 62.423 | 66.673 | 6.369 | 1.00 | 10.00 |
| ATOM | 610 | CA | THR | 92 | 62.754 | 67.515 | 7.533 | 1.00 | 10.00 |
| ATOM | 611 | C | THR | 92 | 61.753 | 67.219 | 8.662 | 1.00 | 10.00 |
| ATOM | 612 | O | THR | 92 | 60.544 | 67.323 | 8.459 | 1.00 | 10.00 |
| ATOM | 613 | CB | THR | 92 | 62.699 | 68.997 | 7.157 | 1.00 | 10.00 |
| ATOM | 614 | OG1 | THR | 92 | 63.678 | 69.249 | 6.145 | 1.00 | 10.00 |
| ATOM | 615 | CG2 | THR | 92 | 62.988 | 69.930 | 8.336 | 1.00 | 10.00 |
| ATOM | 616 | N | ALA | 93 | 62.300 | 66.907 | 9.832 | 1.00 | 10.00 |
| ATOM | 617 | CA | ALA | 93 | 61.523 | 66.528 | 11.030 | 1.00 | 10.00 |
| ATOM | 618 | C | ALA | 93 | 62.452 | 66.098 | 12.168 | 1.00 | 10.00 |
| ATOM | 619 | O | ALA | 93 | 63.660 | 65.932 | 11.996 | 1.00 | 10.00 |
| ATOM | 620 | CB | ALA | 93 | 60.572 | 65.353 | 10.743 | 1.00 | 10.00 |
| ATOM | 621 | N | ILE | 94 | 61.857 | 66.023 | 13.351 | 1.00 | 10.00 |
| ATOM | 622 | CA | ILE | 94 | 62.530 | 65.440 | 14.521 | 1.00 | 10.00 |
| ATOM | 623 | C | ILE | 94 | 62.345 | 63.915 | 14.433 | 1.00 | 10.00 |
| ATOM | 624 | O | ILE | 94 | 61.215 | 63.431 | 14.385 | 1.00 | 10.00 |
| ATOM | 625 | CB | ILE | 94 | 61.933 | 66.011 | 15.816 | 1.00 | 10.00 |
| ATOM | 626 | CG1 | ILE | 94 | 62.039 | 67.546 | 15.842 | 1.00 | 10.00 |
| ATOM | 627 | CG2 | ILE | 94 | 62.693 | 65.416 | 17.006 | 1.00 | 10.00 |
| ATOM | 628 | CD1 | ILE | 94 | 61.310 | 68.217 | 17.015 | 1.00 | 10.00 |
| ATOM | 629 | N | TYR | 95 | 63.460 | 63.207 | 14.523 | 1.00 | 10.00 |
| ATOM | 630 | CA | TYR | 95 | 63.464 | 61.737 | 14.454 | 1.00 | 10.00 |
| ATOM | 631 | C | TYR | 95 | 63.686 | 61.162 | 15.848 | 1.00 | 10.00 |
| ATOM | 632 | O | TYR | 95 | 64.612 | 61.543 | 16.562 | 1.00 | 10.00 |
| ATOM | 633 | CB | TYR | 95 | 64.576 | 61.241 | 13.533 | 1.00 | 10.00 |
| ATOM | 634 | CG | TYR | 95 | 64.332 | 61.703 | 12.097 | 1.00 | 10.00 |
| ATOM | 635 | CD1 | TYR | 95 | 64.765 | 62.953 | 11.703 | 1.00 | 10.00 |
| ATOM | 636 | CD2 | TYR | 95 | 63.632 | 60.892 | 11.215 | 1.00 | 10.00 |
| ATOM | 637 | CE1 | TYR | 95 | 64.491 | 63.375 | 10.405 | 1.00 | 10.00 |
| ATOM | 638 | CE2 | TYR | 95 | 63.391 | 61.314 | 9.916 | 1.00 | 10.00 |
| ATOM | 639 | CZ | TYR | 95 | 63.858 | 62.546 | 9.505 | 1.00 | 10.00 |
| ATOM | 640 | OH | TYR | 95 | 64.048 | 62.698 | 8.183 | 1.00 | 10.00 |
| ATOM | 641 | N | TYR | 96 | 62.774 | 60.285 | 16.212 | 1.00 | 10.00 |
| ATOM | 642 | CA | TYR | 96 | 62.793 | 59.592 | 17.501 | 1.00 | 10.00 |
| ATOM | 643 | C | TYR | 96 | 63.057 | 58.103 | 17.293 | 1.00 | 10.00 |
| ATOM | 644 | O | TYR | 96 | 62.471 | 57.459 | 16.422 | 1.00 | 10.00 |
| ATOM | 645 | CB | TYR | 96 | 61.452 | 59.776 | 18.210 | 1.00 | 10.00 |
| ATOM | 646 | CG | TYR | 96 | 61.209 | 61.238 | 18.576 | 1.00 | 10.00 |
| ATOM | 647 | CD1 | TYR | 96 | 61.742 | 61.738 | 19.754 | 1.00 | 10.00 |
| ATOM | 648 | CD2 | TYR | 96 | 60.461 | 62.059 | 17.739 | 1.00 | 10.00 |

FIG. 12L

| | | | | | | | | |
|---|---|---|---|---|---|---|---|---|
| ATOM | 649 | CE1 | TYR | 96 | 61.528 | 63.065 | 20.098 | 1.00 10.00 |
| ATOM | 650 | CE2 | TYR | 96 | 60.253 | 63.387 | 18.081 | 1.00 10.00 |
| ATOM | 651 | CZ | TYR | 96 | 60.792 | 63.889 | 19.261 | 1.00 10.00 |
| ATOM | 652 | OH | TYR | 96 | 60.672 | 65.207 | 19.565 | 1.00 10.00 |
| ATOM | 653 | N | CYS | 97 | 63.959 | 57.613 | 18.125 | 1.00 10.00 |
| ATOM | 654 | CA | CYS | 97 | 64.226 | 56.171 | 18.226 | 1.00 10.00 |
| ATOM | 655 | C | CYS | 97 | 63.300 | 55.617 | 19.311 | 1.00 10.00 |
| ATOM | 656 | O | CYS | 97 | 63.093 | 56.247 | 20.350 | 1.00 10.00 |
| ATOM | 657 | CB | CYS | 97 | 65.682 | 55.930 | 18.616 | 1.00 10.00 |
| ATOM | 658 | SG | CYS | 97 | 66.065 | 54.148 | 18.775 | 1.00 10.00 |
| ATOM | 659 | N | ALA | 98 | 62.774 | 54.435 | 19.036 | 1.00 10.00 |
| ATOM | 660 | CA | ALA | 98 | 61.833 | 53.769 | 19.949 | 1.00 10.00 |
| ATOM | 661 | C | ALA | 98 | 62.019 | 52.254 | 19.901 | 1.00 10.00 |
| ATOM | 662 | O | ALA | 98 | 62.403 | 51.691 | 18.873 | 1.00 10.00 |
| ATOM | 663 | CB | ALA | 98 | 60.396 | 54.135 | 19.577 | 1.00 10.00 |
| ATOM | 664 | N | ALA | 99 | 61.812 | 51.643 | 21.055 | 1.00 10.00 |
| ATOM | 665 | CA | ALA | 99 | 61.915 | 50.183 | 21.195 | 1.00 10.00 |
| ATOM | 666 | C | ALA | 99 | 60.636 | 49.587 | 21.818 | 1.00 10.00 |
| ATOM | 667 | O | ALA | 99 | 59.750 | 50.310 | 22.250 | 1.00 10.00 |
| ATOM | 668 | CB | ALA | 99 | 63.186 | 49.833 | 21.976 | 1.00 10.00 |
| ATOM | 669 | N | GLY | 100 | 60.418 | 48.306 | 21.562 | 1.00 10.00 |
| ATOM | 670 | CA | GLY | 100 | 59.305 | 47.548 | 22.158 | 1.00 10.00 |
| ATOM | 671 | C | GLY | 100 | 59.903 | 46.495 | 23.088 | 1.00 10.00 |
| ATOM | 672 | O | GLY | 100 | 60.522 | 45.544 | 22.610 | 1.00 10.00 |
| ATOM | 673 | N | HIS | 101 | 59.829 | 46.765 | 24.389 | 1.00 10.00 |
| ATOM | 674 | CA | HIS | 101 | 60.436 | 45.888 | 25.416 | 1.00 10.00 |
| ATOM | 675 | C | HIS | 101 | 59.796 | 44.505 | 25.555 | 1.00 10.00 |
| ATOM | 676 | O | HIS | 101 | 60.442 | 43.576 | 26.034 | 1.00 10.00 |
| ATOM | 677 | CB | HIS | 101 | 60.425 | 46.528 | 26.800 | 1.00 10.00 |
| ATOM | 678 | CG | HIS | 101 | 61.346 | 47.734 | 26.847 | 1.00 10.00 |
| ATOM | 679 | ND1 | HIS | 101 | 62.675 | 47.726 | 26.881 | 1.00 50.00 |
| ATOM | 680 | CD2 | HIS | 101 | 60.919 | 48.968 | 27.002 | 1.00 50.00 |
| ATOM | 681 | CE1 | HIS | 101 | 63.056 | 48.984 | 27.002 | 1.00 50.00 |
| ATOM | 682 | NE2 | HIS | 101 | 61.985 | 49.749 | 27.104 | 1.00 50.00 |
| ATOM | 683 | N | ALA | 102 | 58.518 | 44.411 | 25.193 | 1.00 10.00 |
| ATOM | 684 | CA | ALA | 102 | 57.742 | 43.168 | 25.339 | 1.00 10.00 |
| ATOM | 685 | C | ALA | 102 | 58.327 | 42.027 | 24.494 | 1.00 10.00 |
| ATOM | 686 | O | ALA | 102 | 58.488 | 42.156 | 23.282 | 1.00 10.00 |
| ATOM | 687 | CB | ALA | 102 | 56.286 | 43.421 | 24.941 | 1.00 50.00 |
| ATOM | 688 | N | GLY | 103 | 58.620 | 40.925 | 25.189 | 1.00 10.00 |
| ATOM | 689 | CA | GLY | 103 | 59.085 | 39.680 | 24.548 | 1.00 10.00 |
| ATOM | 690 | C | GLY | 103 | 57.860 | 38.807 | 24.261 | 1.00 10.00 |
| ATOM | 691 | O | GLY | 103 | 57.401 | 38.072 | 25.132 | 1.00 10.00 |
| ATOM | 692 | N | ALA | 104 | 57.285 | 39.020 | 23.080 | 1.00 10.00 |
| ATOM | 693 | CA | ALA | 104 | 56.029 | 38.365 | 22.664 | 1.00 10.00 |
| ATOM | 694 | C | ALA | 104 | 56.130 | 36.831 | 22.697 | 1.00 10.00 |
| ATOM | 695 | O | ALA | 104 | 57.163 | 36.255 | 22.365 | 1.00 10.00 |
| ATOM | 696 | CB | ALA | 104 | 55.657 | 38.832 | 21.256 | 1.00 50.00 |
| ATOM | 697 | N | ALA | 105 | 55.031 | 36.218 | 23.127 | 1.00 10.00 |
| ATOM | 698 | CA | ALA | 105 | 54.902 | 34.745 | 23.197 | 1.00 10.00 |
| ATOM | 699 | C | ALA | 105 | 54.747 | 34.129 | 21.797 | 1.00 10.00 |
| ATOM | 700 | O | ALA | 105 | 55.408 | 33.154 | 21.451 | 1.00 10.00 |
| ATOM | 701 | CB | ALA | 105 | 53.701 | 34.380 | 24.074 | 1.00 10.00 |
| ATOM | 702 | N | GLY | 106 | 53.872 | 34.767 | 21.008 | 1.00 10.00 |
| ATOM | 703 | CA | GLY | 106 | 53.636 | 34.408 | 19.600 | 1.00 10.00 |
| ATOM | 704 | C | GLY | 106 | 54.370 | 35.411 | 18.705 | 1.00 10.00 |

FIG. 12M

| | | | | | | | | | |
|---|---|---|---|---|---|---|---|---|---|
| ATOM | 705 | O | GLY | 106 | 54.727 | 36.507 | 19.143 | 1.00 | 10.00 |
| ATOM | 706 | N | ALA | 107 | 54.584 | 35.014 | 17.454 | 1.00 | 10.00 |
| ATOM | 707 | CA | ALA | 107 | 55.246 | 35.876 | 16.456 | 1.00 | 10.00 |
| ATOM | 708 | C | ALA | 107 | 54.521 | 37.228 | 16.346 | 1.00 | 10.00 |
| ATOM | 709 | O | ALA | 107 | 53.295 | 37.288 | 16.258 | 1.00 | 10.00 |
| ATOM | 710 | CB | ALA | 107 | 55.253 | 35.185 | 15.091 | 1.00 | 50.00 |
| ATOM | 711 | N | ALA | 108 | 55.303 | 38.286 | 16.508 | 1.00 | 10.00 |
| ATOM | 712 | CA | ALA | 108 | 54.794 | 39.666 | 16.425 | 1.00 | 10.00 |
| ATOM | 713 | C | ALA | 108 | 55.609 | 40.448 | 15.395 | 1.00 | 10.00 |
| ATOM | 714 | O | ALA | 108 | 56.839 | 40.413 | 15.392 | 1.00 | 10.00 |
| ATOM | 715 | CB | ALA | 108 | 54.888 | 40.345 | 17.793 | 1.00 | 50.00 |
| ATOM | 716 | N | THR | 109 | 54.892 | 41.193 | 14.569 | 1.00 | 10.00 |
| ATOM | 717 | CA | THR | 109 | 55.511 | 42.008 | 13.506 | 1.00 | 10.00 |
| ATOM | 718 | C | THR | 109 | 55.684 | 43.442 | 14.024 | 1.00 | 10.00 |
| ATOM | 719 | O | THR | 109 | 54.722 | 44.157 | 14.302 | 1.00 | 10.00 |
| ATOM | 720 | CB | THR | 109 | 54.669 | 41.972 | 12.217 | 1.00 | 50.00 |
| ATOM | 721 | OG1 | THR | 109 | 53.384 | 42.555 | 12.454 | 1.00 | 50.00 |
| ATOM | 722 | CG2 | THR | 109 | 54.505 | 40.544 | 11.681 | 1.00 | 50.00 |
| ATOM | 723 | N | CYS | 110 | 56.943 | 43.859 | 14.147 | 1.00 | 10.00 |
| ATOM | 724 | CA | CYS | 110 | 57.302 | 45.209 | 14.644 | 1.00 | 10.00 |
| ATOM | 725 | C | CYS | 110 | 56.676 | 46.347 | 13.824 | 1.00 | 10.00 |
| ATOM | 726 | O | CYS | 110 | 56.390 | 47.421 | 14.354 | 1.00 | 10.00 |
| ATOM | 727 | CB | CYS | 110 | 58.817 | 45.418 | 14.638 | 1.00 | 10.00 |
| ATOM | 728 | SG | CYS | 110 | 59.746 | 44.433 | 15.867 | 1.00 | 10.00 |
| ATOM | 729 | N | GLY | 111 | 56.382 | 46.037 | 12.550 | 1.00 | 10.00 |
| ATOM | 730 | CA | GLY | 111 | 55.743 | 46.980 | 11.614 | 1.00 | 10.00 |
| ATOM | 731 | C | GLY | 111 | 54.332 | 47.391 | 12.056 | 1.00 | 10.00 |
| ATOM | 732 | O | GLY | 111 | 53.910 | 48.524 | 11.826 | 1.00 | 10.00 |
| ATOM | 733 | N | HIS | 112 | 53.683 | 46.505 | 12.815 | 1.00 | 10.00 |
| ATOM | 734 | CA | HIS | 112 | 52.306 | 46.703 | 13.297 | 1.00 | 10.00 |
| ATOM | 735 | C | HIS | 112 | 52.176 | 47.953 | 14.183 | 1.00 | 10.00 |
| ATOM | 736 | O | HIS | 112 | 51.438 | 48.875 | 13.837 | 1.00 | 10.00 |
| ATOM | 737 | CB | HIS | 112 | 51.852 | 45.459 | 14.065 | 1.00 | 10.00 |
| ATOM | 738 | CG | HIS | 112 | 50.389 | 45.580 | 14.491 | 1.00 | 10.00 |
| ATOM | 739 | ND1 | HIS | 112 | 49.346 | 45.283 | 13.727 | 1.00 | 10.00 |
| ATOM | 740 | CD2 | HIS | 112 | 49.940 | 45.976 | 15.680 | 1.00 | 10.00 |
| ATOM | 741 | CE1 | HIS | 112 | 48.246 | 45.486 | 14.444 | 1.00 | 10.00 |
| ATOM | 742 | NE2 | HIS | 112 | 48.614 | 45.910 | 15.650 | 1.00 | 10.00 |
| ATOM | 743 | N | GLY | 113 | 53.044 | 48.016 | 15.204 | 1.00 | 10.00 |
| ATOM | 744 | CA | GLY | 113 | 53.073 | 49.142 | 16.156 | 1.00 | 10.00 |
| ATOM | 745 | C | GLY | 113 | 53.468 | 50.448 | 15.461 | 1.00 | 10.00 |
| ATOM | 746 | O | GLY | 113 | 52.800 | 51.469 | 15.628 | 1.00 | 10.00 |
| ATOM | 747 | N | LEU | 114 | 54.368 | 50.305 | 14.485 | 1.00 | 10.00 |
| ATOM | 748 | CA | LEU | 114 | 54.908 | 51.425 | 13.701 | 1.00 | 10.00 |
| ATOM | 749 | C | LEU | 114 | 53.814 | 52.190 | 12.935 | 1.00 | 10.00 |
| ATOM | 750 | O | LEU | 114 | 53.702 | 53.407 | 13.064 | 1.00 | 10.00 |
| ATOM | 751 | CB | LEU | 114 | 55.952 | 50.890 | 12.716 | 1.00 | 10.00 |
| ATOM | 752 | CG | LEU | 114 | 56.788 | 52.012 | 12.093 | 1.00 | 10.00 |
| ATOM | 753 | CD1 | LEU | 114 | 57.747 | 52.611 | 13.119 | 1.00 | 10.00 |
| ATOM | 754 | CD2 | LEU | 114 | 57.593 | 51.480 | 10.914 | 1.00 | 10.00 |
| ATOM | 755 | N | SER | 115 | 52.940 | 51.428 | 12.284 | 1.00 | 10.00 |
| ATOM | 756 | CA | SER | 115 | 51.828 | 51.982 | 11.485 | 1.00 | 10.00 |
| ATOM | 757 | C | SER | 115 | 50.638 | 52.478 | 12.322 | 1.00 | 10.00 |
| ATOM | 758 | O | SER | 115 | 49.831 | 53.273 | 11.853 | 1.00 | 10.00 |
| ATOM | 759 | CB | SER | 115 | 51.328 | 50.951 | 10.471 | 1.00 | 10.00 |
| ATOM | 760 | OG | SER | 115 | 50.846 | 49.779 | 11.137 | 1.00 | 10.00 |

FIG. 12N

| ATOM | 761 | N   | THR | 116 | 50.561 | 52.009 | 13.564 | 1.00 | 10.00 |
| ATOM | 762 | CA  | THR | 116 | 49.386 | 52.253 | 14.430 | 1.00 | 10.00 |
| ATOM | 763 | C   | THR | 116 | 49.662 | 53.276 | 15.541 | 1.00 | 10.00 |
| ATOM | 764 | O   | THR | 116 | 49.294 | 53.068 | 16.697 | 1.00 | 10.00 |
| ATOM | 765 | CB  | THR | 116 | 48.886 | 50.937 | 15.049 | 1.00 | 10.00 |
| ATOM | 766 | OG1 | THR | 116 | 49.915 | 50.381 | 15.876 | 1.00 | 10.00 |
| ATOM | 767 | CG2 | THR | 116 | 48.427 | 49.934 | 13.985 | 1.00 | 10.00 |
| ATOM | 768 | N   | ALA | 117 | 50.438 | 54.314 | 15.215 | 1.00 | 10.00 |
| ATOM | 769 | CA  | ALA | 117 | 50.791 | 55.399 | 16.159 | 1.00 | 10.00 |
| ATOM | 770 | C   | ALA | 117 | 51.700 | 54.908 | 17.308 | 1.00 | 10.00 |
| ATOM | 771 | O   | ALA | 117 | 51.492 | 55.205 | 18.483 | 1.00 | 10.00 |
| ATOM | 772 | CB  | ALA | 117 | 49.521 | 56.100 | 16.685 | 1.00 | 50.00 |
| ATOM | 773 | N   | GLY | 118 | 52.605 | 53.988 | 16.947 | 1.00 | 10.00 |
| ATOM | 774 | CA  | GLY | 118 | 53.675 | 53.504 | 17.844 | 1.00 | 10.00 |
| ATOM | 775 | C   | GLY | 118 | 53.177 | 52.716 | 19.065 | 1.00 | 10.00 |
| ATOM | 776 | O   | GLY | 118 | 53.881 | 52.638 | 20.072 | 1.00 | 10.00 |
| ATOM | 777 | N   | ALA | 119 | 52.022 | 52.058 | 18.934 | 1.00 | 10.00 |
| ATOM | 778 | CA  | ALA | 119 | 51.491 | 51.162 | 19.983 | 1.00 | 10.00 |
| ATOM | 779 | C   | ALA | 119 | 52.502 | 50.038 | 20.221 | 1.00 | 10.00 |
| ATOM | 780 | O   | ALA | 119 | 53.096 | 49.551 | 19.258 | 1.00 | 10.00 |
| ATOM | 781 | CB  | ALA | 119 | 50.169 | 50.547 | 19.517 | 1.00 | 50.00 |
| ATOM | 782 | N   | ALA | 120 | 52.798 | 49.780 | 21.500 | 1.00 | 10.00 |
| ATOM | 783 | CA  | ALA | 120 | 53.773 | 48.774 | 21.998 | 1.00 | 10.00 |
| ATOM | 784 | C   | ALA | 120 | 55.175 | 49.348 | 22.258 | 1.00 | 10.00 |
| ATOM | 785 | O   | ALA | 120 | 55.908 | 48.819 | 23.099 | 1.00 | 10.00 |
| ATOM | 786 | CB  | ALA | 120 | 53.916 | 47.501 | 21.141 | 1.00 | 50.00 |
| ATOM | 787 | N   | GLY | 121 | 55.537 | 50.394 | 21.497 | 1.00 | 10.00 |
| ATOM | 788 | CA  | GLY | 121 | 56.808 | 51.121 | 21.668 | 1.00 | 10.00 |
| ATOM | 789 | C   | GLY | 121 | 56.806 | 51.917 | 22.984 | 1.00 | 10.00 |
| ATOM | 790 | O   | GLY | 121 | 56.332 | 53.047 | 23.030 | 1.00 | 10.00 |
| ATOM | 791 | N   | ALA | 122 | 57.274 | 51.270 | 24.044 | 1.00 | 10.00 |
| ATOM | 792 | CA  | ALA | 122 | 57.277 | 51.841 | 25.413 | 1.00 | 10.00 |
| ATOM | 793 | C   | ALA | 122 | 58.456 | 52.794 | 25.734 | 1.00 | 10.00 |
| ATOM | 794 | O   | ALA | 122 | 58.252 | 53.752 | 26.483 | 1.00 | 10.00 |
| ATOM | 795 | CB  | ALA | 122 | 57.163 | 50.713 | 26.450 | 1.00 | 50.00 |
| ATOM | 796 | N   | PRO | 123 | 59.680 | 52.514 | 25.256 | 1.00 | 10.00 |
| ATOM | 797 | CA  | PRO | 123 | 60.855 | 53.392 | 25.427 | 1.00 | 10.00 |
| ATOM | 798 | C   | PRO | 123 | 61.074 | 54.255 | 24.186 | 1.00 | 10.00 |
| ATOM | 799 | O   | PRO | 123 | 61.140 | 53.783 | 23.048 | 1.00 | 10.00 |
| ATOM | 800 | CB  | PRO | 123 | 62.037 | 52.440 | 25.564 | 1.00 | 50.00 |
| ATOM | 801 | CG  | PRO | 123 | 61.647 | 51.337 | 24.590 | 1.00 | 50.00 |
| ATOM | 802 | CD  | PRO | 123 | 60.153 | 51.194 | 24.854 | 1.00 | 50.00 |
| ATOM | 803 | N   | TRP | 124 | 61.352 | 55.498 | 24.505 | 1.00 | 10.00 |
| ATOM | 804 | CA  | TRP | 124 | 61.660 | 56.519 | 23.495 | 1.00 | 10.00 |
| ATOM | 805 | C   | TRP | 124 | 62.959 | 57.230 | 23.867 | 1.00 | 10.00 |
| ATOM | 806 | O   | TRP | 124 | 63.240 | 57.461 | 25.044 | 1.00 | 10.00 |
| ATOM | 807 | CB  | TRP | 124 | 60.512 | 57.527 | 23.434 | 1.00 | 10.00 |
| ATOM | 808 | CG  | TRP | 124 | 59.242 | 56.924 | 22.829 | 1.00 | 10.00 |
| ATOM | 809 | CD1 | TRP | 124 | 58.300 | 56.230 | 23.466 | 1.00 | 10.00 |
| ATOM | 810 | CD2 | TRP | 124 | 58.855 | 57.032 | 21.505 | 1.00 | 10.00 |
| ATOM | 811 | NE1 | TRP | 124 | 57.337 | 55.897 | 22.606 | 1.00 | 10.00 |
| ATOM | 812 | CE2 | TRP | 124 | 57.644 | 56.368 | 21.401 | 1.00 | 10.00 |
| ATOM | 813 | CE3 | TRP | 124 | 59.425 | 57.649 | 20.400 | 1.00 | 10.00 |
| ATOM | 814 | CZ2 | TRP | 124 | 56.995 | 56.312 | 20.176 | 1.00 | 10.00 |
| ATOM | 815 | CZ3 | TRP | 124 | 58.775 | 57.591 | 19.174 | 1.00 | 10.00 |
| ATOM | 816 | CH2 | TRP | 124 | 57.564 | 56.922 | 19.065 | 1.00 | 10.00 |
| ATOM | 817 | N   | GLY | 125 | 63.750 | 57.485 | 22.825 | 1.00 | 10.00 |

FIG. 12O

| ATOM | 818 | CA | GLY | 125 | 64.974 | 58.296 | 22.943 | 1.00 | 10.00 |
| ATOM | 819 | C | GLY | 125 | 64.629 | 59.777 | 22.747 | 1.00 | 10.00 |
| ATOM | 820 | O | GLY | 125 | 63.516 | 60.138 | 22.361 | 1.00 | 10.00 |
| ATOM | 821 | N | GLN | 126 | 65.601 | 60.620 | 23.065 | 1.00 | 10.00 |
| ATOM | 822 | CA | GLN | 126 | 65.503 | 62.064 | 22.784 | 1.00 | 10.00 |
| ATOM | 823 | C | GLN | 126 | 65.501 | 62.281 | 21.268 | 1.00 | 10.00 |
| ATOM | 824 | O | GLN | 126 | 66.223 | 61.600 | 20.537 | 1.00 | 10.00 |
| ATOM | 825 | CB | GLN | 126 | 66.692 | 62.801 | 23.407 | 1.00 | 10.00 |
| ATOM | 826 | CG | GLN | 126 | 66.729 | 62.672 | 24.936 | 1.00 | 10.00 |
| ATOM | 827 | CD | GLN | 126 | 65.507 | 63.273 | 25.645 | 1.00 | 10.00 |
| ATOM | 828 | OE1 | GLN | 126 | 64.630 | 63.914 | 25.083 | 1.00 | 10.00 |
| ATOM | 829 | NE2 | GLN | 126 | 65.447 | 63.061 | 26.941 | 1.00 | 10.00 |
| ATOM | 830 | N | GLY | 127 | 64.646 | 63.207 | 20.826 | 1.00 | 10.00 |
| ATOM | 831 | CA | GLY | 127 | 64.544 | 63.539 | 19.393 | 1.00 | 10.00 |
| ATOM | 832 | C | GLY | 127 | 65.854 | 64.073 | 18.823 | 1.00 | 10.00 |
| ATOM | 833 | O | GLY | 127 | 66.654 | 64.694 | 19.521 | 1.00 | 10.00 |
| ATOM | 834 | N | THR | 128 | 66.071 | 63.740 | 17.562 | 1.00 | 10.00 |
| ATOM | 835 | CA | THR | 128 | 67.243 | 64.211 | 16.805 | 1.00 | 10.00 |
| ATOM | 836 | C | THR | 128 | 66.724 | 64.925 | 15.560 | 1.00 | 10.00 |
| ATOM | 837 | O | THR | 128 | 66.026 | 64.331 | 14.738 | 1.00 | 10.00 |
| ATOM | 838 | CB | THR | 128 | 68.158 | 63.041 | 16.415 | 1.00 | 10.00 |
| ATOM | 839 | OG1 | THR | 128 | 68.550 | 62.337 | 17.597 | 1.00 | 10.00 |
| ATOM | 840 | CG2 | THR | 128 | 69.407 | 63.512 | 15.660 | 1.00 | 10.00 |
| ATOM | 841 | N | GLN | 129 | 67.000 | 66.220 | 15.501 | 1.00 | 10.00 |
| ATOM | 842 | CA | GLN | 129 | 66.539 | 67.039 | 14.373 | 1.00 | 10.00 |
| ATOM | 843 | C | GLN | 129 | 67.318 | 66.667 | 13.089 | 1.00 | 10.00 |
| ATOM | 844 | O | GLN | 129 | 68.543 | 66.555 | 13.100 | 1.00 | 10.00 |
| ATOM | 845 | CB | GLN | 129 | 66.727 | 68.517 | 14.734 | 1.00 | 10.00 |
| ATOM | 846 | CG | GLN | 129 | 65.692 | 69.438 | 14.070 | 1.00 | 10.00 |
| ATOM | 847 | CD | GLN | 129 | 65.730 | 69.422 | 12.546 | 1.00 | 10.00 |
| ATOM | 848 | OE1 | GLN | 129 | 66.771 | 69.153 | 11.948 | 1.00 | 10.00 |
| ATOM | 849 | NE2 | GLN | 129 | 64.705 | 69.876 | 11.889 | 1.00 | 10.00 |
| ATOM | 850 | N | VAL | 130 | 66.560 | 66.466 | 12.022 | 1.00 | 10.00 |
| ATOM | 851 | CA | VAL | 130 | 67.131 | 66.407 | 10.651 | 1.00 | 10.00 |
| ATOM | 852 | C | VAL | 130 | 66.458 | 67.476 | 9.763 | 1.00 | 10.00 |
| ATOM | 853 | O | VAL | 130 | 65.232 | 67.548 | 9.656 | 1.00 | 10.00 |
| ATOM | 854 | CB | VAL | 130 | 66.996 | 64.993 | 10.083 | 1.00 | 10.00 |
| ATOM | 855 | CG1 | VAL | 130 | 67.250 | 64.860 | 8.575 | 1.00 | 10.00 |
| ATOM | 856 | CG2 | VAL | 130 | 67.807 | 63.968 | 10.882 | 1.00 | 10.00 |
| ATOM | 857 | N | THR | 131 | 67.310 | 68.275 | 9.132 | 1.00 | 10.00 |
| ATOM | 858 | CA | THR | 131 | 66.897 | 69.379 | 8.247 | 1.00 | 10.00 |
| ATOM | 859 | C | THR | 131 | 67.455 | 69.129 | 6.844 | 1.00 | 10.00 |
| ATOM | 860 | O | THR | 131 | 68.666 | 69.068 | 6.634 | 1.00 | 10.00 |
| ATOM | 861 | CB | THR | 131 | 67.381 | 70.745 | 8.774 | 1.00 | 10.00 |
| ATOM | 862 | OG1 | THR | 131 | 66.826 | 70.967 | 10.064 | 1.00 | 10.00 |
| ATOM | 863 | CG2 | THR | 131 | 66.902 | 71.917 | 7.913 | 1.00 | 10.00 |
| ATOM | 864 | N | VAL | 132 | 66.531 | 69.113 | 5.898 | 1.00 | 10.00 |
| ATOM | 865 | CA | VAL | 132 | 66.866 | 68.956 | 4.473 | 1.00 | 10.00 |
| ATOM | 866 | C | VAL | 132 | 66.521 | 70.272 | 3.762 | 1.00 | 10.00 |
| ATOM | 867 | O | VAL | 132 | 65.366 | 70.696 | 3.726 | 1.00 | 10.00 |
| ATOM | 868 | CB | VAL | 132 | 66.108 | 67.772 | 3.851 | 1.00 | 10.00 |
| ATOM | 869 | CG1 | VAL | 132 | 66.513 | 67.584 | 2.387 | 1.00 | 10.00 |
| ATOM | 870 | CG2 | VAL | 132 | 66.372 | 66.463 | 4.603 | 1.00 | 10.00 |
| ATOM | 871 | N | SER | 133 | 67.563 | 70.875 | 3.212 | 1.00 | 10.00 |
| ATOM | 872 | CA | SER | 133 | 67.446 | 72.145 | 2.471 | 1.00 | 10.00 |
| ATOM | 873 | C | SER | 133 | 67.110 | 71.875 | 1.002 | 1.00 | 10.00 |

FIG. 12P

| | | | | | | | | | |
|---|---|---|---|---|---|---|---|---|---|
| ATOM | 874 | O | SER | 133 | 67.506 | 70.863 | 0.433 | 1.00 | 10.00 |
| ATOM | 875 | CB | SER | 133 | 68.748 | 72.941 | 2.582 | 1.00 | 10.00 |
| ATOM | 876 | OG | SER | 133 | 68.990 | 73.237 | 3.961 | 1.00 | 10.00 |
| ATOM | 877 | N | SER | 134 | 66.405 | 72.821 | 0.400 | 1.00 | 10.00 |
| ATOM | 878 | CA | SER | 134 | 65.975 | 72.726 | -1.015 | 1.00 | 10.00 |
| ATOM | 879 | C | SER | 134 | 66.807 | 73.626 | -1.949 | 1.00 | 10.00 |
| ATOM | 880 | O | SER | 134 | 67.468 | 74.544 | -1.422 | 1.00 | 10.00 |
| ATOM | 881 | CB | SER | 134 | 64.492 | 73.090 | -1.124 | 1.00 | 10.00 |
| ATOM | 882 | OG | SER | 134 | 64.101 | 73.153 | -2.497 | 1.00 | 10.00 |
| ATOM | 883 | OXT | SER | 134 | 66.636 | 73.469 | -3.183 | 1.00 | 99.99 |
| TERM | | | | | | | | | |
| END | | | | | | | | | |

FIG. 12Q

# TARGET RECOGNIZING BINDING AGENTS

RELATED APPLICATION

This application is a Divisional under 37 C.F.R. 1.53(b) of U.S. patent application Ser. No. 10/335,181 filed Dec. 30, 2002, which has issued as U.S. Pat. No. 6,974,860, which is incorporated by reference herein.

FIELD OF THE INVENTION

The present invention relates generally to the field of antibody-like binding agents that can specifically recognize and bind to a target.

BACKGROUND OF THE INVENTION

A standard antibody is a tetrameric structure consisting of two identical immunoglobulin heavy chains and two identical light chains. The heavy and light chains of an antibody consist of different domains. Each light chain has one variable domain and one constant domain, while each heavy chain has one variable domain and three or four constant domains. Alzari, P. N., Lascombe, M.-B. & Poljak, R. J. (1988). Three-dimensional structure of antibodies. Ann. Rev. Immunol. 6, 555-580. Each domain consists of about 110 amino acid residues. Each domain is also folded into a characteristic β-sandwich structure formed from two β-sheets packed against each other (the immunoglobulin fold). The variable heavy and variable light domains each have three complementarity determining regions (CDR1-3) that connect the β-strands at one end of the domains. The variable regions of both the light and heavy chains generally contribute to antigen specificity, although the contribution of the individual chains to specificity is not always equal. Hence, antibody molecules are large and complex.

Antibody molecules have evolved to bind to a large number of molecules by using six randomized loops (CDRs). However, the size and the existence of six different loops on separate polypeptides constitute a hurdle to molecular manipulations that might otherwise be used to improve the structure, stability and binding properties of antibodies. Moreover, while antibodies are widely used in medical research, industrial processes and in diagnostics, they are expensive and difficult to obtain. They also lack suitable stability for long shelf life.

What would be useful is a smaller, more stable binding agent that can easily be manipulated by standard cloning procedures and that could be produced in cultured host cells, rather than in animals. Such new types of binding agents would ideally have the positive features of antibodies (e.g., high specificity and affinity for binding a distinct target) but few of the negative aspects of antibodies (e.g., instability and difficulty of production). Moreover, new procedures are also needed for large-scale preparation of such binding agents in cultured cells that would avoid the time and expense of using animals.

SUMMARY OF THE INVENTION

The invention relates to polypeptides and methods of making binding agents that can specifically recognize any desired target molecule (protein, peptide, nucleic acid, small molecule, etc.). The binding agents overcome many of the inherent limitations of monoclonal or polyclonal antibodies. For example, no animals need to be used to make the binding agents. Instead, such binding agents can readily be produced in a variety of host cells, including bacteria. These new binding agents can then be purified, studied, modified, and used in assays, commercial diagnostic devices or as therapeutic agents in place of antibodies.

Hence, the invention is directed to an isolated binding agent including a polypeptide comprising SEQ ID NO:2 or SEQ ID NO:4 or SEQ ID NO:37. The polypeptide can have a number of binding loops (e.g. five) where each loop comprises Xaa amino acids. Such Xaa amino acids can be genetically encoded L-amino acids, naturally occurring non-genetically encoded L-amino acids, synthetic L-amino acids or D-enantiomers thereof. Each Xaa amino acid of such isolated binding agent can be exchanged for a specific amino acid so that the polypeptide can bind to a selected target molecule.

The invention is also directed to isolated nucleic acids that encode a polypeptide comprising SEQ ID NO:2 or SEQ ID NO:4. Examples of such isolated nucleic acids comprise nucleic acids having SEQ ID NO:1 or SEQ ID NO:3. The nucleic acid can be within a replicable vector or a replicable plasmid.

The invention is also directed to oligonucleotides comprising random loop sequences. For example, such an oligonucleotide can have SEQ ID NO:25, SEQ ID NO:26, SEQ ID NO:27, SEQ ID NO:28 or SEQ ID NO:29.

The invention is further directed to an expression vector comprising a promoter and a nucleic acid encoding a binding agent of the invention. For example, the expression vector can encode a binding agent polypeptide comprising SEQ ID NO:2 or SEQ ID NO:4 or SEQ ID NO:37. The nucleic acid can, for example, comprise SEQ ID NO:1 or SEQ ID NO:3.

The invention is also directed to a library of binding agents wherein each binding agent in the library comprises a polypeptide comprising SEQ ID NO:2 or SEQ ID NO:37.

The invention also relates to methods for making the binding agents. In one method, nucleic acids and vectors encoding a parental binding agent are provided where the binding loops of the parental binding agent can easily be modified to generate a library of binding agents. Such a library can then be screened for agents that bind a particular target. In another embodiment, the invention is directed to a computer-assisted method for sequentially fitting the structural coordinates of a target molecule onto different binding agents and determining the sequence of binding loops that have a good fit.

Hence, the invention is directed to a method of making a library of binding agent nucleic acids comprising: generating a collection of random oligonucleotides, each random oligonucleotide comprising a random sequence about 6 to about 30 n nucleotides, wherein n is A, C, G or T; and substituting each random oligonucleotide into a nucleic acid comprising SEQ ID NO:1 to generate a library of binding agent nucleic acids. At least one of the collection of random oligonucleotides can comprise SEQ ID NO:25, SEQ ID NO:26, SEQ ID NO:27, SEQ ID NO:28 or SEQ ID NO:29. The method can further comprise placing the library of binding agent nucleic acids into a population of host cells to generate a library of host cells.

The invention is also directed to a method of making a library of replicable vectors that encode binding agent polypeptides comprising: generating a collection of random oligonucleotides, each random oligonucleotide comprising a random sequence about 6 to about 30 n nucleotides, wherein n is A, C, G or T; and substituting each random oligonucleotide into a replicable vector comprising SEQ ID NO:1 to generate a library of replicable vectors that encode binding agent polypeptides. At least one of the collection of random oligonucleotides can comprise SEQ ID NO:25, SEQ ID NO:26, SEQ ID NO:27, SEQ ID NO:28 or SEQ ID NO:29.

The method can further comprise placing the library of binding agent vectors into a population of host cells to generate a library of host cells.

The invention is further directed to a method of making a library of binding agent polypeptides comprising: generating a collection of random oligonucleotides, each random oligonucleotide comprising a random sequence about 6 to about 30 n nucleotides, wherein n is A, C, G or T; substituting each random oligonucleotide into an expression vector comprising SEQ ID NO:1 to generate a library of expression vectors that encode binding agent polypeptides; and placing the library of expression vectors into a population of host cells to generate a library of host cells that express a library of binding agent polypeptides. At least one of the collection of random oligonucleotides can comprise SEQ ID NO:25, SEQ ID NO:26, SEQ ID NO:27, SEQ ID NO:28 or SEQ ID NO:29.

The invention is also directed to a method of making a library of binding agent nucleic acids comprising: generating a collection of random oligonucleotides, each random oligonucleotide comprising a random sequence about 6 to about 30 n nucleotides, wherein n is A, C, G or T; and substituting each random oligonucleotide into a nucleic acid comprising SEQ ID NO:37 to generate a library of binding agent nucleic acids. At least one of the collection of random oligonucleotides can comprise SEQ ID NO:25, SEQ ID NO:26, SEQ ID NO:27, SEQ ID NO:28 or SEQ ID NO:29.

The invention is further directed to a method of making a library of replicable vectors that encode binding agent polypeptides comprising: generating a collection of random oligonucleotides, each random oligonucleotide comprising a random sequence about 6 to about 30 n nucleotides, wherein n is A, C, G or T; and substituting each random oligonucleotide into a replicable vector comprising SEQ ID NO:37 to generate a library of replicable vectors that encode binding agent polypeptides. At least one of the collection of random oligonucleotides can comprise SEQ ID NO:25, SEQ ID NO:26, SEQ ID NO:27, SEQ ID NO:28 or SEQ ID NO:29. The method can further comprise placing the library of binding agent vectors into a population of host cells to generate a library of host cells.

The invention is also directed to a method of making a library of binding agent polypeptides comprising: generating a collection of random oligonucleotides, each random oligonucleotide comprising a random sequence about 6 to about 30 n nucleotides, wherein n is A, C, G or T; substituting each random oligonucleotide into an expression vector comprising SEQ ID NO:37 to generate a library of expression vectors that encode binding agent polypeptides; and placing the library of expression vectors into a population of host cells to generate a library of host cells that express a library of binding agent polypeptides. At least one of the collection of random oligonucleotides can comprise SEQ ID NO:25, SEQ ID NO:26, SEQ ID NO:27, SEQ ID NO:28 or SEQ ID NO:29.

The invention is further directed to a computer implemented method of making a library of binding agents comprising: defining a search zone comprising a site of interaction on a target molecule to which a binding agent with at least one binding loop can interact; defining number of binding loops to search and a size for each binding loop; defining a class of amino acids for each position in each binding loop amino acid sequence; substituting members of a defined class of amino acids into positions of each binding loop amino acid sequence to generate a plurality of output binding loop sequences; fitting each of the plurality of output binding loop sequences to the search zone and to create a target molecule-binding loop sequence fit score; and ranking the plurality of output binding loop sequences by target molecule-binding loop sequence fit score; wherein the binding agent comprises SEQ ID NO:2 or SEQ ID NO:37. The search zone can comprise x-, y- and z-coordinates of each non-hydrogen atom in the target molecule. The method can further comprise entering x-, y- and z-coordinates of each non-hydrogen atom in the binding agent comprising SEQ ID NO: or SEQ ID NO:37.

The method can further comprise receiving an input percentage selection to limit the output binding loop sequences to a certain percentage; wherein the input percentage selection is capable of limiting an output library file size and a library complexity. In general, the output binding loop sequences with higher target molecule-binding loop sequence fit scores can bind with higher affinity to the target molecule. The target molecule can, for example, be bovine trypsin and one of the output binding loop sequence can, for example, be SEQ ID NO:35.

The invention is also directed to a system for generating peptide sequences, comprising: a processor; a memory coupled to the processor; a display coupled to the processor; a make loop peptide sequence component capable of executing on the processor to generate output loop peptide sequences; a molecular docking component capable of fitting a plurality of output loop peptide sequences to a search zone on a target molecule and generating a target molecule-binding loop sequence fit score; an output loop sequence component capable of executing on the processor to display loop peptide sequences; and an output binding agent sequence component capable of executing on the processor to display binding agent sequences.

The invention is further directed to a machine-accessible medium having associated content capable of directing the machine to perform a method, the method comprising: defining a search zone comprising a site of interaction on a target molecule to which a binding agent with at least one binding loop can interact; defining number of binding loops to search and a size for each binding loop; defining a class of amino acids for each position in each binding loop amino acid sequence; substituting members of a defined class of amino acids into positions of each binding loop amino acid sequence to generate a plurality of output binding loop sequences; fitting each of the plurality of output binding loop sequences to the search zone and to create a target molecule-binding loop sequence fit score; and ranking the plurality of output binding loop sequences by target molecule-binding loop sequence fit score; wherein the binding agent comprises SEQ ID NO:2 or SEQ ID NO:37. The machine-accessible medium can further comprise a file of x-, y- and z-coordinates for each non-hydrogen atom in the binding agent comprising SEQ ID NO:2, SEQ ID NO:37 or SEQ ID NO:38. For example, the x-, y- and z-coordinates of SEQ ID NO:2, SEQ ID NO:37 or SEQ ID NO:38 can be used by the molecular docking program to align each binding loop sequence with the target molecule.

DESCRIPTION OF THE FIGURES

FIG. 2 provides a DNA sequence of a binding reagent of the invention (SEQ ID NO:1). Underlined sequences denote the 5' Nde I site and the 3' Eco RV sequence that have been incorporated into the DNA sequence in order to facilitate cloning. The n's denote the positions of random nucleotides (e.g., A, C, G or T) that correspond to the loop portions of the binding reagent. The initiation and termination codons are in bold.

FIG. 3 shows an amino acid sequence of a parental binding agent of the invention (SEQ ID NO:2). One letter amino acid nomenclature is employed and the X's are random amino acids that correspond to the five loop regions (i to v).

FIG. 4 shows a DNA sequence of a generic binding reagent (SEQ ID NO:3). Underlined sequences denote the 5' Nde I site and the 3' Eco RV sequence that have been incorporated into the DNA sequence in order to facilitate cloning. The loop portions of the binding reagent DNA sequence in FIG. 1 have been replaced by codons coding for alanine and glycine. In this way the generic binding reagent could be purified and stability studied prior to building the combinatorial library. The initiation and termination codons are in bold.

FIG. 5 provides the amino acid sequence of a generic binding reagent (SEQ ID NO:4). One letter amino acid nomenclature is employed. The loop regions (i to v) have been replaced with alanine and glycine.

FIGS. 12A-Q provide a listing of the structural coordinates for a generic polypeptide having SEQ ID NO:38. The SEQ ID NO:38 polypeptide is a generic binding agent like the SEQ ID NO:4, except that SEQ ID NO:38 does not have the N-terminal Met-Asp amino acids found in SEQ ID NO:4.

DETAILED DESCRIPTION OF THE INVENTION

Figure 1A:
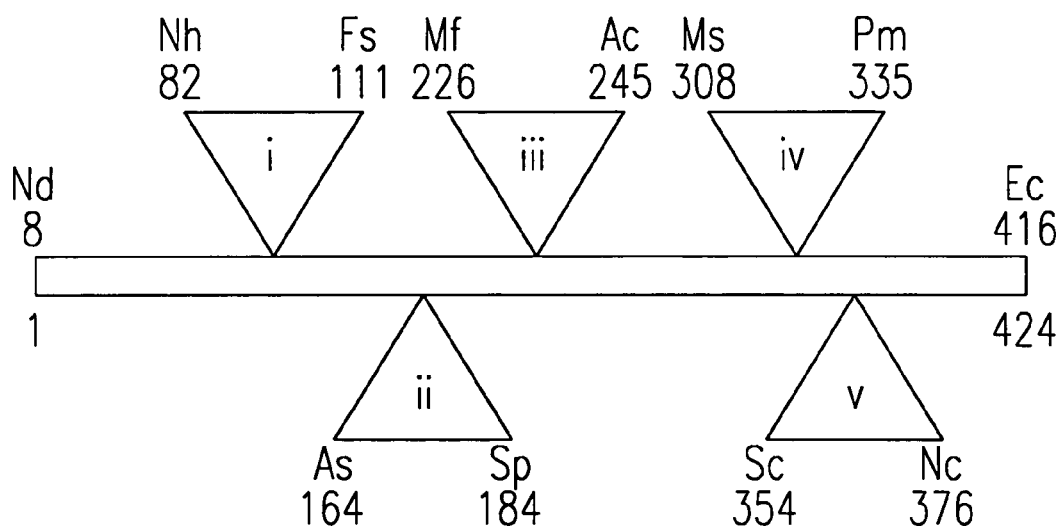
FIG. 1A is a schematic diagram of a nucleic acid encoding a binding agent of the invention. The unique restriction sites that were engineered into the sequence are shown; Nd, Nde I; Nh, Nhe I; Fs, Fsp I; As, Ase I; Sp, Spe I; Mf, Mfe I, Ac, Acl I; Ms, Msc I; Pm, Pml I; Sc, Sca I; Nc, Nco I; and Ec, Eco RV. Numbers refer to the position of the restriction sites and to the gene length, all in nucleotides. The positions of the five corresponding loop regions (i to v) are also shown.

The invention is directed to binding agents that comprise a polypeptide having "structure-determining" and "function-controlling" amino acids, wherein the structure-determining amino acids promote formation of a stable, anti-parallel, beta barrel conformation and the "function-controlling" amino acids promote specificity of binding to a distinct molecular entity such as a distinct protein, polysaccharide, peptide, or a similar molecule. Examples of binding agents of the invention include polypeptides having SEQ ID NO:2, SEQ ID NO:4 or SEQ ID NO:38.

Binding Agent Properties

A stable binding agent polypeptide of the invention has several desirable properties. Some of these desirable properties are described below.

First, the residues that control stability and global conformation of desirable binding agent polypeptides are distinct and distinguishable from those that control function. After identification, the function-controlling amino acid residues can be manipulated without altering the stability and global conformation of desirable binding agent polypeptides. The invention is therefore directed to a parental backbone polypeptide, in which all function-controlling amino acid residues have been identified, and engineered so that they may be easily modified. The function that is of interest in this case is binding to a selected target.

Second, the number of allowed function-controlling amino acid residues in the binding agent polypeptide is sufficient to permit generation of a diverse population of polypeptides with varying degrees of functionality. No exact number of function-controlling amino acids need be incorporated into the binding agent polypeptides of the invention. However, using too few function-controlling amino acids will not generate a diverse population of binding agents, whereas using a large number of function-controlling amino acids means that a large number of sites may need to be manipulated to generate an optimal binding agent. For example, if only two residues were used to control function, then systematic substitution of the 20 naturally occurring amino acids at both sites generates only a rather small array of binding agents with only $20^2$ members. However, if 40 residues are used to control function, then an array with $20^{40}$ members can be generated.

The number of function-controlling amino acids for the present binding agents can generally vary between about 15 to about 50 amino acids, or from about 20 to about 40 amino acids. In some embodiments, the binding agent polypeptide was designed to have about thirty target recognition (i.e. function controlling) amino acids dispersed in five different loops. When 30 residues are used to control function, then an array with $20^{30}$ ($10^{39}$) different binding agents can be generated.

Third, the function-controlling residues are localized within the three-dimensional structure of the binding agent so as to form at least one well-defined binding surface. Hence, the function-controlling amino acids are not all clustered within a single region of the amino acid sequence of the polypeptide. Instead, the function-controlling amino acids are dispersed through several regions of the binding agent so that, upon folding, the polypeptide presents or provides a functional domain that is effectively lined with the function-controlling amino acids. One exemplary embodiment of the invention is a polypeptide with five loops (i-v) that form a target binding surface. In certain embodiments, the target binding surface of the present polypeptides is predominately comprised of loops (i) and (iv), although the other three loops add diversity (and therefore utility) to the binding agent.

Fourth, the function-controlling amino acids are clustered within distinct regions of the binding agent that can readily be exchanged so that different function-controlling amino acids can be placed in those regions.

Fifth, desirable binding agents are made up of a single subunit that is formed by a single polypeptide chain and this polypeptide chain is able to properly fold in a selected host cell, such as an *E. coli* host cell. Furthermore the polypeptide is highly stable, so that it is resistant to heat and chemical denaturation and has a long shelf life.

While several of the foregoing factors may apply to natural antibodies, several do not. For example, the antigen-binding site of a Fab fragment is composed of the hypervariable regions of both the heavy and light chains. Traditionally, antibodies are difficult to produce using recombinant techniques and they have limited stability.

Binding Agent Structures

The invention is directed to binding agents that comprise a polypeptide having "structure-determining" and "function-controlling" amino acids, wherein the structure-determining amino acids promote formation of a stable, anti-parallel, beta barrel conformation and the "function-controlling" amino acids promote specific binding to a distinct molecular entities such as distinct proteins, polysaccharides, peptides, and the like.

Desirable polypeptide inhibitors of the invention have an anti-parallel, beta barrel conformation. As used herein a beta barrel conformation means that the core of the polypeptide comprises beta strand secondary structures that fold into a barrel-like tertiary structure. The beta strand secondary structures can be arranged in an anti-parallel manner. Moreover, the beta barrel is stabilized by intra-strand hydrogen bonding and internal hydrophobic packing interactions. In the present invention, the fundamental beta barrel conformation is further stabilized by at least one disulfide bond that helps maintain the overall topology of the fold. A beta barrel is a recognized tertiary structure known to those skilled in the art of protein structure and function.

Amino acids involved in binding to target molecules (function-determining amino acids) are displayed on the surface of the barrel-like structure.

The design and use of the binding agents of the invention overcomes several important obstacles to the wide-spread use of conventional antibodies in advanced diagnostics, for example, their large size, their lack of shelf-life, their poor engineering potential, their multiple chain composition, their poor solubility, and their cost.

The starting point for the design of the binding agents of the invention was the structure of antibodies found in the sera of Camelidae. Camels as well as a number of related species (e.g. lamas) have of IgG-like antibody molecules that are only composed of heavy-chain dimers. See Hamers-Casterman et al., Naturally occurring antibodies devoid of light chains. Nature 363 (Jun. 3, 1993) 446-448; WO 97/49805. Although these "heavy-chain" antibodies are devoid of light chains, they nevertheless have antigen-binding properties.

One example of a binding agent of the invention has SEQ ID NO:2, provided below.

```
 1 Met Asp Val Gln Leu Gln Ala Ser Gly Gly

11 Gly Ser Val Gln Ala Gly Gly Ser Leu Arg
```

-continued
```
21 Leu Ser Cys Ala Ala Ser Xaa Xaa Xaa Xaa

31 Xaa Xaa Xaa Cys Ala Gly Trp Phe Arg Asn

41 Ala Pro Gly Lys Glu Arg Glu Gly Val Ala

51 Ala Ile Asn Xaa Xaa Xaa Xaa Xaa Tyr Ser

61 Tyr Ala Asp Ser Val Lys Gly Arg Phe Thr

71 Ile Ser Gln Leu Xaa Xaa Xaa Xaa Asn Val

81 Tyr Leu Leu Met Asn Ser Leu Glu Pro Glu

91 Asp Thr Ala Ile Tyr Tyr Cys Ala Ala Gly

101 His Xaa Xaa Xaa Xaa Xaa Xaa Xaa Xaa Cys

111 Gly His Gly Leu Ser Thr Xaa Xaa Xaa Xaa

121 Xaa Xaa Pro Trp Gly Gln Gly Thr Gln Val

131 Thr Val Ser Ser
``` wherein Xaa is any natural or synthetic amino acid available to one of skill in the art.

This binding agent (SEQ ID NO:2) is called the parental binding agent because, while the structure-determining amino acids are largely determined, the function-determining amino acids (Xaa residues) are not. The function-determining amino acids can easily be altered or modified as desired by one of skill in the art, for example, by using the methods of the invention. The function-determining amino acids within SEQ ID NO:2 polypeptides are clustered within five separate loops (i to v). The first loop (i) of a SEQ ID NO:2 polypeptide is at positions 27 to 33; the second loop (ii) is at positions 54 to 58; the third loop (iii) is at positions 75 to 78; the fourth loop (iv) is at positions 102 to 109; and the fifth loop (v) is at positions 117 to 122.

Generic binding agents have been made that have the same structure-determining amino acids as the parental binding agent but with only glycine and alanine residues in the loop domains. These generic binding agents were made to permit analysis of the physicochemical properties (e.g. stability) of a generic construct prior to making a library of binding agents with different loop sequences. Moreover, the generic binding agents can be used for comparison with specific binding agent constructs that are isolated by the methods of the invention. One example of an amino acid sequence for a generic binding agent is provided below (SEQ ID NO:4).

```
  1 MDVQLQASGG GSVQAGGSLR LSCAASAGAA GAACAGWFRQ

41 APGKEREGVA AINAGAAGTS YADSVKGRFT ISQLAGAANV

81 YLLMNSLEPE DTAIYYCAAG HAGAAGAATC GHGLSTAGAA

121 GAPWGQGTQV TVSS
```

The SEQ ID NO:38 polypeptide is a generic binding agent like the SEQ ID NO:4, except that SEQ ID NO:38 does not have the N-terminal Met-Asp amino acids found in SEQ ID NO:4. The sequence of the SEQ ID NO:38 generic binding agent is provided below.

```
  1    VQLQASGG GSVQAGGSLR LSCAASAGAA GAACAGWFRQ

41 APGKEREGVA AINAGAAGTS YADSVKGRFT ISQLAGAANV
```

-continued

```
 81 YLLMNSLEPE DTAIYYCAAG HAGAAGAATC GHGLSTAGAA

121 GAPWGQGTQV TVSS
```

Amino acid residues within the binding agents of the invention can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | Bala |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | Hcys |
| Homoserine | | Hser |
| ε-Amino hexanoic acid | | Aha |
| δ-Amino valeric acid | | Ava |
| 2,3-Diaminobutyric acid | | Dab |

Any such amino acid, or any other amino acid known to one of skill in the art, can be utilized as a function-controlling amino acid (Xaa) in the binding agents of the invention.

Moreover, binding agents that are encompassed within the scope of the invention can have one or more structure-determining amino acids substituted with an amino acid of similar chemical and/or physical properties, so long as these variant or derivative binding agent polypeptides can retain a stable, anti-parallel, beta barrel conformation.

Amino acids that are substitutable for each other generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a polypeptide.

Certain commonly encountered amino acids that are not genetically encoded and that can be present, or substituted for an amino acid, in the polypeptides and polypeptide analogues of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the binding agent polypeptides described herein. Other amino acid residues that are useful for making the binding agent polypeptides of the invention can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Binding agent polypeptides of the invention can have any structure-determining amino acid substituted by any similarly classified amino acid to create a variant or derivative binding agent polypeptide, so long as the binding agent polypeptide variant or derivative retains an ability to form a stable, anti-parallel, beta barrel conformation.

The binding agents of the invention can therefore be made even more stable by modulation of the structure-determining amino acids through substitution of one or more amino acids within SEQ ID NO:2. Stability enhancement or design selection procedures that are available to one of skill in the art can be utilized for this purpose. For example, one of skill in the art can systematically change each one of the structure-determining amino acids in SEQ ID NO:2 to any available natural or synthetic amino acid, observe whether the modified polypeptide structure is further resistant to thermal or chemical denaturation and utilize only those amino acid substitutions that improve the stability of the polypeptide.

Moreover, the binding properties of the binding agents of the invention can be modulated by systematically altering each of the function-controlling amino acids (Xaa) of a binding agent such as SEQ ID NO:2.

In one embodiment, at least one of structure-determining amino acids of the parental binding agent (SEQ ID NO:2) is changed to an amino acid of the same class. In other embodiments, several of the structure-determining determining amino acids of the parental binding agent (SEQ ID NO:2) are changed to amino acids of the same class. Hence the invention is directed to a variant parental binding agent with the following sequence (SEQ ID NO:37):

1 $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$

11 $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$

21 $Xaa_{21}$ $Xaa_{22}$ $Xaa_{23}$ $Xaa_{24}$ $Xaa_{25}$ $Xaa_{26}$ Xaa Xaa Xaa Xaa

31 Xaa Xaa Xaa $Xaa_{34}$ $Xaa_{35}$ $Xaa_{36}$ $Xaa_{37}$ $Xaa_{38}$ $Xaa_{39}$ $Xaa_{40}$

41 $Xaa_{41}$ $Xaa_{42}$ $Xaa_{43}$ $Xaa_{44}$ $Xaa_{45}$ $Xaa_{46}$ $Xaa_{47}$ $Xaa_{48}$ $Xaa_{49}$ $Xaa_{50}$

51 $Xaa_{51}$ $Xaa_{52}$ $Xaa_{53}$ Xaa Xaa Xaa Xaa Xaa $Xaa_{59}$ $Xaa_{60}$

-continued

61 Xaa₆₁ Xaa₆₂ Xaa₆₃ Xaa₆₄ Xaa₆₅ Xaa₆₆ Xaa₆₇ Xaa₆₈ Xaa₆₉ Xaa₇₀

71 Xaa₇₁ Xaa₇₂ Xaa₇₃ Xaa₇₄ Xaa Xaa Xaa Xaa Xaa₇₉ Xaa₈₀

81 Xaa₈₁ Xaa₈₂ Xaa₈₃ Xaa₈₄ Xaa₈₅ Xaa₈₆ Xaa₈₇ Xaa₈₈ Xaa₈₉ Xaa₉₀

91 Xaa₉₁ Xaa₉₂ Xaa₉₃ Xaa₉₄ Xaa₉₅ Xaa₉₆ Xaa₉₇ Xaa₉₈ Xaa₉₉ Xaa₁₀₀

101 Xaa₁₀₁ Xaa Xaa Xaa Xaa Xaa Xaa Xaa Xaa Xaa₁₁₀

111 Xaa₁₁₁ Xaa₁₁₂ Xaa₁₁₃ Xaa₁₁₄ Xaa₁₁₅ Xaa Xaa Xaa Xaa

121 Xaa Xaa Xaa₁₂₃ Xaa₁₂₄ Xaa₁₂₅ Xaa₁₂₆ Xaa₁₂₇ Xaa₁₂₈ Xaa₁₂₉ Xaa₁₃₀

131 Xaa₁₃₁ Xaa₁₃₂ Xaa₁₃₃ Xaa₁₃₄ wherein:

Xaa is any natural or synthetic amino acid available to one of skill in the art;

Xaa₁, Xaa₉, Xaa₁₀, Xaa₁₁, Xaa₁₆, Xaa₁₇, Xaa₃₆, Xaa₄₂, Xaa₄₃, Xaa₄₈, Xaa₆₇, Xaa₈₄, Xaa₈₉, Xaa₉₇, Xaa₁₀₀, Xaa₁₁₁, Xaa₁₁₃, Xaa₁₂₃, Xaa₁₂₅, and Xaa₁₂₇ are separately each apolar amino acids;

Xaa₂, Xaa₄₅, Xaa₄₇, Xaa₆₃, Xaa₈₈, Xaa₉₀, and Xaa₉₁ are separately each acidic amino acids;

Xaa₃, Xaa₅, Xaa₇, Xaa₁₃, Xaa₁₅, Xaa₁₉, Xaa₂₁, Xaa₂₄, Xaa₂₅, Xaa₃₅, Xaa₄₁, Xaa₄₉, Xaa₅₀, Xaa₅₁, Xaa₅₂, Xaa₆₂, Xaa₆₅, Xaa₇₁, Xaa₇₄, Xaa₈₀, Xaa₈₂, Xaa₈₃, Xaa₈₇, Xaa₉₃, Xaa₉₄, Xaa₉₈, Xaa₉₉, Xaa₁₁₄, Xaa₁₃₀, and Xaa₁₃₂ are separately each aliphatic amino acids;

Xaa₄, Xaa₆, Xaa₈, Xaa₁₂, Xaa₁₄, Xaa₁₈, Xaa₂₂, Xaa₂₆, Xaa₄₀, Xaa₅₃, Xaa₅₉, Xaa₆₀, Xaa₆₁, Xaa₆₄, Xaa₇₀, Xaa₇₂, Xaa₇₃, Xaa₇₉, Xaa₈₁, Xaa₈₅, Xaa₈₆, Xaa₉₂, Xaa₉₅, Xaa₉₆, Xaa₁₁₅, Xaa₁₁₆, Xaa₁₂₆, Xaa₁₂₈, Xaa₁₂₉, Xaa₁₃₁, Xaa₁₃₃, and Xaa₁₃₄ are separately each polar amino acids;

Xaa₂₃, Xaa₃₄, Xaa₉₇, and Xaa₁₁₀ are separately each cysteine-like amino acids;

Xaa₃₇, Xaa₃₈, Xaa₆₉, and Xaa₁₂₄ are separately each aromatic amino acids; and

Xaa₂₀, Xaa₃₉, Xaa₄₄, Xaa₄₆, Xaa₆₆, Xaa₆₈, Xaa₁₀₁, and Xaa₁₁₂ are separately each basic amino acids.

Any procedure available to one of skill in art can be used to alter the structure-determining or the function-controlling amino acids of the present binding agents. For example, at least two general methods can be used to modify the binding agents of the invention.

The first method is by design. One of skill in the art can examine the structural and binding domains of known natural antibody-antigen complexes (especially those that have been solved by x-ray crystallography) to identify specific structural interactions that may stabilize the conformation of the binding agent. Similarly, one of skill in the art may examine the structures of antibody-antigen or enzyme-inhibitor complexes to identify specific binding interactions that may increase the affinity of the binding agent for its target.

The second, more general method, is to generate a vast array of binding agents ("artificial antibodies"). A selected target molecule ("antigen") can be used to select binding agents from the array that have the desired binding properties. This brute-force (but effective) combinatorial approach is made possible by simple, easily manipulated structure of the binding agents, which can be encoded by a single, comparatively small nucleic acid.

One such nucleic acid, which encodes a polypeptide having SEQ ID NO:2, is a nucleic acid having SEQ ID NO:1 provided below.

```
  1 ACACACCATA TGGACGTTCA GCTGCAGGCT TCTGCTGGTG
 41 GTTCTGTTCA GGCTGGTGGT TCTCTGCGTC TGTCTTGCGC
 81 TGCTAGCnnn nnnnnnnnnn nnnnnnnnTG CGCAGGTTGG
121 TTCCGTCAGG CTCCGGGTAA AGAACGTGAA GGTGTTGCTC
161 CTATTAATnn nnnnnnnnnn nnnACTAGTT ACGCTGACTC
201 TGTTAAACGT CGTTTCACGA TCTCTCAATT Gnnnnnnnnn
241 nnnAACGTTT ACCTGCTGAT GAACTCTCTG GAACCGGAAG
281 ACACCGCTAT CTACTACTGC GCTGCTGGCC ACnnnnnnnn
321 nnnnnnnnnn nnCACGTGCG GTCACGGTCT GAGTACTnnn
361 nnnnnnnnnn nnnnnCCATG GGGTCAGGGT ACCCAGGTTA
401 CCGTTTCTTC TTAGATATCA CAC
``` wherein n can be any nucleotide (e.g. A, C, G or T).

According to the invention, the SEQ ID NO:1 has nucleotide sequences can be quickly and easily replaced by standard molecular biological procedures to generate a large number of binding agents, each with different binding properties. Hence, a combinatorial library can readily be constructed with randomized binding contact loop domains. Such a library of binding agents can be screened to identify specific binding agents that recognize distinct target molecules, for example, by phage display or biopanning procedures.

Combinatorial Libraries

The present invention also relates to binding agent libraries and methods for generating and screening those libraries to identify binding agents that bind to target molecules of interest. The binding agent polypeptides are produced from libraries of expression vectors that encode a polypeptide having SEQ ID NO:2 or SEQ ID NO:37, wherein the Xaa amino acids are any amino acid. The library of polypeptide binding agents is screened using a selected target molecule to identify polypeptides that can bind to the selected target molecule. The binding agent can then be synthesized in bulk by conventional means.

Exemplary screening methods of the invention comprise the steps of (a) generating oligonucleotides with randomized sequences that are of the approximate length of the loop regions of the SEQ ID NO:2 or the SEQ ID NO:37 binding agent; (b) inserting the randomized oligonucleotides into an expression vector (e.g., comprising the SEQ ID NO:1 nucleic acid) to generate a library of binding agents where the function-determining amino acids (e.g., the n nucleotides of SEQ ID NO:1) that correspond to loops i-v are replaced by the randomized oligonucleotides; (c) expressing the library of binding agents; and (d) identifying which binding agent(s) bind a selected target molecule.

Hence, the construction of a combinatorial library of polypeptide binding agents starts with a vector that encodes a parental or generic agent, for example, a vector that encodes SEQ ID NO:1.

A nucleic acid having SEQ ID NO:1 is provided below.

```
  1 ACACACCATA TGGACGTTCA GCTGCAGGCT TCTGGTGGTG
 41 GTTCTGTTCA CGCTGCTGCT TCTCTCCGTC TGTCTTGCGC
 81 TGCTACCnnn nnnnnnnnnn nnnnnnnnTG CGCAGGTTGG
121 TTCCGTCAGG CTCCGGGTAA AGAACGTGAA GGTGTTGCTG
161 CTATTAATnn nnnnnnnnnn nnnACTAGTT ACGCTGACTC
201 TGTTAAAGGT CGTTTCACCA TCTCTCAATT Gnnnnnnnnn
241 nnnAACGTTT ACCTGCTGAT GAACTCTCTC GAACCGGAAG
281 ACACCCCTAT CTACTACTGC GCTCCTGGCC ACnnnnnnnn
321 nnnnnnnnnn nnCACGTCCG GTCACGGTCT GAGTACTnnn
361 nnnnnnnnnn nnnnnCCATG GGGTCAGGGT ACCCAGGTTA
401 CCGTTTCTTC TTAGATATCA CAC
``` wherein n can be any nucleotide (e.g. A, C, G or T).

The nucleotide positions having undefined n nucleotides correspond to regions that are loops in the encoded polypeptide. Hence, in one embodiment, loop i corresponds to nucleotide positions 88-108 of SEQ ID NO:1; loop ii corresponds to nucleotide positions 169-183 of SEQ ID NO:1; loop iii corresponds to nucleotide positions 232-243 of SEQ ID NO:1; loop iv corresponds to nucleotide positions 313-332 of SEQ ID NO:1; and loop v corresponds to nucleotide positions 358-375 of SEQ ID NO:1. It should be noted that the length of the loops, and the corresponding nucleic acid that encodes those loops, can vary. Hence, while the nucleic acids encoding the loops have defined lengths in SEQ ID NO:1, those loop-encoding regions can easily be removed and replaced with oligonucleotides of different lengths.

A vector is used to facilitate manipulation, replication and expression of a parental or generic binding agent (for example, the SEQ ID NO:1 nucleic acid). The vector can be any convenient vector that will express a binding agent comprising SEQ ID NO:2 or SEQ ID NO:37 from a nucleic acid encoding such a binding agent. Once a vector is constructed to encode the SEQ ID NO:2 or 37 generic binding agent, one of skill in the art need only clone loop peptide coding sequences in frame with the SEQ ID NO:2 or 37 coding sequence to obtain a random binding agent polypeptide library of the invention.

Randomized oligonucleotides that correspond to the loop regions of the binding agents can be synthesized using standard solid phase chemistry. While the randomized oligonucleotides can have any convenient flanking sequences, added flanking sequences that provide restriction sites can be used to facilitate insertion of the random oligonucleotides into the nucleic acid that encodes the structure-determining amino acids of the binding agent.

For example, sequences of randomized oligonucleotides can be as provided in Table 3 below.

TABLE 3

Randomized loop oligonucleotide sequences

| Loop No. | Sequence | Restriction Sites | SEQ ID NO: |
|---|---|---|---|
| i | GCTAGCnnnn nnnnnnnnnn nnnnnnnTGC GCA | Nhe I Fsp I | 25 |
| ii | ATTAATnnnn nnnnnnnnnn NACTACT | Ase I Spe I | 26 |
| iii | CAATTGnnnn nnnnnnAACG TT | Mfe I Acl I | 27 |
| iv | TGGCCAnnnn nnnnnnnnnn nnnnnnnCAC GTG | Msc I Pml I | 28 |
| v | AGTACTnnnn nnnnnnnnnn NnnnCCATGG | Sca I Nco I | 29 |

The loop regions (i to v) correspond to the loop regions of the present binding regions. Table 3 therefore provides the sequence of oligonucleotides that can be used for generating combinatorial libraries of binding agents, as well as the incorporated unique restriction sites that flank the random nucleotides (n) and facilitate cloning. The position and number of random nucleotides (n) are indicated. Hence, loop i has 21 random nucleotides, loop ii has 15 random nucleotides, loop iii has 12 random nucleotides, loop iv has 21 random nucleotides, and loop v has 18 random nucleotides. For example the oligonucleotide for loop i is a 33 nucleotide sequence with 21 central random bases with a Nhe I site at the 5' end and a Fsp I site at the 3' end.

The variable loop sequences provided by the randomized oligonucleotide provide a key feature of the library: the binding domains of the binding agents of the invention. The size of the library will vary according to the number of variable codons, and hence the size of the loops, that are desired. Generally, the library will be at least 106 to 108 or more members, although smaller libraries may be quite useful in some circumstances.

The collection of randomized oligonucleotides that encode the loop sequences need not be completely random. For example, codon usage can be optimized for expression in a particular organism. However, it may be simpler and less expensive to utilize random oligonucleotides and then optimize codon usage for expression later. The expression of peptides from randomly generated mixtures of oligonucleotides in recombinant vectors is discussed in Oliphant et al., 1986, Gene 44:177-183, incorporated herein by reference.

For example, to prepare oligonucleotides for insertion into the vector encoding the parental binding agent, each of the random (e.g., SEQ ID NO:25-29) oligonucleotides can be hybridized with their complimentary binding partners. The vector is then digested with selected pairs of restriction enzymes, for example, Nhe I and Fsp I if loop i random oligonucleotides are to be ligated into the vector. This linear plasmid is isolated. The loop i oligonucleotides are digested with the same restriction enzymes. Digested oligonucleotides and plasmid are mixed and ligated together, for example, by using T4 DNA ligase. The random oligonucleotides that correspond to loop regions ii to v are similarly inserted into the vector.

The finally ligated vector product can then be introduced into an appropriate host cell type, for example, a bacterial cell type, a yeast cell type, an insect cell type or a mammalian cell type. The cells can then be plated and screened for expression of a binding agent polypeptide that can bind a selected target molecule.

Any vector that can replicate in a selected host cell can be utilized in the invention. In general, the vector is an expression vector that provides the nucleic acid segments needed for expression of the binding agent polypeptides. Various vectors are publicly available. The vector may, for example, be in the form of a plasmid, cosmid, viral particle, or phage. Vector components generally include, but are not limited to, one or more of a signal sequence, an origin of replication, one or more marker genes, an enhancer element, a promoter, and a transcription termination sequence.

The binding agent and random oligonucleotide loop nucleic acid sequences may be inserted into the vector by a variety of procedures. In general, DNA is inserted into an appropriate restriction endonuclease site(s) using techniques known in the art. See generally, Sambrook et al., 1989, Molecular Cloning, A Laboratory Manual, 2d ed., Cold Spring Harbor Laboratory Press, Cold Spring Harbor, N.Y.; Sambrook and Russell, Molecular Cloning: A Laboratory Manual, 3rd edition (Jan. 15, 2001) Cold Spring Harbor Laboratory Press, ISBN: 0879695765; Ausubel et al., *Current Protocols in Molecular Biology*, Green Publishing Associates and Wiley Interscience, NY (1989)). Construction of suitable expression vectors containing a generic binding agent and one or more random loop oligonucleotides employs standard ligation techniques that are known to the skilled artisan.

The invention therefor provides an expression cassette capable of directing the expression of a binding agent polypeptide. Such an expression cassette can be placed within a vector to generate an expression vector.

The expression cassette of the invention includes a promoter. Any promoter able to direct transcription of the expression cassette may be used. Accordingly, many promoters may be included within the expression cassette of the invention. Some useful promoters include, constitutive promoters, inducible promoters, regulated promoters, cell specific promoters, viral promoters, and synthetic promoters. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

For expression of a polypeptide in a bacterium, an expression cassette having a bacterial promoter is used. A bacterial promoter is any DNA sequence capable of binding bacterial RNA polymerase and initiating the downstream (3') transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature*, 198:1056 (1977)), and maltose. Additional examples include promoter sequences derived from biosynthetic enzymes such as tryptophan (trp) (Goeddel et al., *N.A.R.*, 8: 4057 (1980); Yelverton et al., *N.A.R.*, 9: 731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689, 406) promoter systems also provide useful promoter sequences. Another promoter is the *Chlorella* virus promoter (U.S. Pat. No. 6,316,224).

Synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter that is regulated by the lac repressor and that is comprised of both the trp promoter and the lac operon sequences (Amann et al., *Gene*, 25:167 (1983); de Boer et al., *Proc. Natl. Acad. Sci. USA*, 80: 21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189: 113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267.851).

An expression cassette having an insect promoter such as a baculovirus promoter can be used for expression of a polypeptide in an insect cell. A baculovirus promoter is any DNA sequence capable of binding a baculovirus RNA polymerase and initiating transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein (Friesen et al., "The Regulation of Baculovirus Gene Expression", in: The Molecular Biology of Baculoviruses (ed. Walter Doerfler), 1986; and EPO Publ. Nos. 127 839 and 155 476) and the gene encoding the baculoviral p10 protein (Vlak et al., *J. Gen. Virol.*, 69: 765 (1988)).

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression can be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PHO5 gene, encoding acid phosphatase, also provides useful promoter sequences. (Myanohara et al., *Proc. Natl. Acad. Sci. USA*, 80:1 (1983)).

Synthetic promoters that do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters that consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters are known in the art. (Cohen et al., *Proc. Natl. Acad. Sci. USA*, 77: 1078 (1980); Henikoff et al., *Nature*, 283:835 (1981); Hollenberg et al., *Curr. Topics Microbiol. Immunol.*, 96: 119 (1981); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979; Mercerau-Puigalon et al., *Gene*, 11:163 (1980); Panthier et al., *Curr. Genet.*, 2:109 (1980)).

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science*, 236:1237 (1987); Alberts et al., Molecular Biology of the Cell, 2nd ed., 1989)). Enhancer elements derived from viruses are often times useful, because they usually have a broad host range. Examples include the SV40 early gene enhancer (Dijkema et al., *EMBO J.*, 4:761 (1985) and the enhancer/promoters derived from the long terminal repeat (LTR) of the Rous Sarcoma Virus (Gorman et al., *Proc. Natl. Acad. Sci. USA*, 79:6777 (1982b)) and from human cytomegalovirus (Boshart et al., *Cell*, 41: 521 (1985)). Additionally, some enhancers are regulatable and become active only in the presence of an inducer, such as a hormone or metal ion (Sassone-Corsi and Borelli, *Trends Genet.*, 2:215 (1986); Maniatis et al., *Science*, 236:1237 (1987)).

It is understood that many promoters and associated regulatory elements may be used within the expression cassette of the invention to transcribe an encoded polypeptide. The promoters described above are provided merely as examples and are not to be considered as a complete list of promoters that are included within the scope of the invention.

The expression cassette of the invention may contain a nucleic acid sequence for increasing the translation efficiency of an mRNA encoding a binding agent of the invention. Such increased translation serves to increase production of the binding agent. The presence of an efficient ribosome binding site is useful for gene expression in prokaryotes. In bacterial mRNA a conserved stretch of six nucleotides, the Shine-Dalgarno sequence, is usually found upstream of the initiating AUG codon. (Shine et al., *Nature*, 254: 34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or an operable derivative thereof, is included within the expression cassette of the invention.

A translation initiation sequence can be derived from any expressed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well known. (Ausubel et al., *Current Protocols in Molecular Biology*, Green Publishing Associates and Wiley Interscience, NY. (1989); Beaucage and Caruthers, *Tetra. Letts.*, 22:1859 (1981); VanDevanter et al., *Nucleic Acids Res.*, 12:6159 (1984). Alternatively, translational start sequences can be obtained from numerous commercial vendors. (Operon Technologies; Life Technologies Inc, Gaithersburg, Md.). In a preferred embodiment, the T7 leader sequence is used. The T7tag leader sequence is derived from the highly expressed T7 Gene 10 cistron. Other examples of translation initiation sequences include, but are not limited to, the maltose-binding protein (Mal E gene) start sequence (Guan et al., *Gene*, 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Current Protocols in Molecular Biology*, Chapter 16, Green Publishing Associates and Wiley Interscience, NY).

Eucaryotic mRNA does not contain a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a polypeptide encoded by the expression cassette of the invention. Such nucleic acid sequences are within the scope of the invention.

Termination sequences can also be included in the vectors of the invention. Usually, transcription termination sequences recognized by bacteria are regulatory regions located 3' to the translation stop codon, and thus together with the promoter flank the coding sequence. These sequences direct the transcription of an mRNA that can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., *Cell*, 41:349 (1985); Proudfoot and Whitelaw, "Termination and 3' end processing of eukaryotic RNA", in: Transcription and Splicing (eds. B. D. Hames and D. M. Glover) 1988; Proudfoot, *Trends Biochem. Sci.*, 14:105 (1989)). These sequences direct the transcription of an mRNA that can be translated into the polypeptide encoded by the DNA. Examples of transcription terminator/polyadenylation signals include those derived from SV40 (Sambrook et al., "Expression of cloned genes in cultured mammalian cells", in: Molecular Cloning: A Laboratory Manual, 1989).

Transcription termination sequences recognized by yeast are regulatory regions that are usually located 3' to the translation stop codon. Examples of transcription terminator sequences that may be used as termination sequences in yeast and insect expression systems are well known. (Lopez-Ferber et al., *Methods Mol. Biol.*, 39:25 (1995); King and Possee, The baculovirus expression system. A laboratory guide. Chapman and Hall, London, England (1992); Gregor and Proudfoot, *EMBO J.*, 17:4771 (1998); O'Reilly et al., Baculovirus expression vectors: a laboratory manual. W.H. Freeman & Company, New York, N.Y. (1992); Richardson, *Crit. Rev. Biochem. Mol. Biol.*, 28:1 (1993); Zhao et al., *Microbiol. Mol. Biol. Rev.*, 63:405 (1999)).

As indicated above, any vector can be utilized to make the libraries of the invention. Vectors that may be used include, but are not limited to, those able to be replicated in prokaryotes and eukaryotes. For example, vectors may be used that are replicated in bacteria, yeast, insect cells, and mammalian cells. Examples of vectors include plasmids, phagemids, bacteriophages, viruses, cosmids, and F-factors.

The invention includes any vector into which the nucleic acid constructs and libraries of the invention may be inserted and replicated in vitro or in vivo. Specific vectors may be used for specific cells types. Additionally, shuttle vectors may be used for cloning and replication in more than one cell type. Such shuttle vectors are known in the art. The nucleic acid constructs or libraries may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolab, Beverly, Mass.; Stratagene, La Jolla, Calif.; Promega, Madison, Wis.; ATCC, Rockville, Md.; CLONTECH, Palo Alto, Calif.; Invitrogen, Carlabad, Calif.; Origene, Rockville, Md.; Sigma, St. Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

A vector for use in a prokaryote host, such as a bacterial cell, includes a replication system allowing it to be maintained in the host for expression or for cloning and amplification. In addition, a vector may be present in the cell in either high or low copy number. Generally, about 5 to about 200, and usually about 10 to about 150 copies of a high copy number vector are present within a host cell. A host cell containing a high copy number vector will preferably contain at least about 10, and more preferably at least about 20 plasmid vectors. Generally, about 1 to 10, and usually about 1 to 4 copies of a low copy number vector will be present in a host cell. The copy number of a vector may be controlled by selection of different origins of replication according to methods known in the art. Sambrook and Russell, Molecular Cloning: A Laboratory Manual, 3rd edition (Jan. 15, 2001) Cold Spring Harbor Laboratory Press, ISBN: 0879695765.

A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrations are thought to result from recombination events between homologous DNA in the vector and the bacterial chromosome. For example, integrating vectors constructed with DNA from various *Bacillus* strains integrate into the *Bacillus* chromosome (EPO Publ. No. 127 328). Integrating vectors may also contain bacteriophage or transposon sequences.

Extrachromosomal and integrating vectors may contain selectable markers to allow for the selection of bacterial strains that have been transformed. Selectable markers can be expressed in the bacterial host and may include genes that render bacteria resistant to drugs such as ampicillin, chloramphenicol, erythromycin, kanamycin (neomycin), and tetracycline (Davies et al., *Ann. Rev. Microbiol.*, 32: 469 (1978)). Selectable markers may also include biosynthetic genes, such as those in the histidine, tryptophan, and leucine biosynthetic pathways.

Numerous vectors, either extra-chromosomal or integrating vectors, have been developed for transformation into many bacteria. For example, vectors have been developed for the following bacteria: *B. subtilis* (Palva et al., *Proc. Natl. Acad. Sci. USA*, 79: 5582 (1982); EPO Publ. Nos. 036 259 and 063 953; PCT Publ. No. WO 84/04541), *E. coli* (Shimatake et al., *Nature*, 292:128 (1981); Amann et al., *Gene*, 40:183 (1985); Studier et al., *J. Mol. Biol.*, 189:113 (1986); EPO Publ. Nos. 036 776, 136 829 and 136 907)), *Streptococcus cremoris* (Powell et al., *Appl. Environ. Microbiol.*, 54: 655 (1988)); *Streptococcus lividans* (Powell et al., *Appl. Environ. Microbiol.*, 54:655 (1988)), and *Streptomyces lividans* (U.S. Pat. No. 4,745,056). Numerous vectors are also commercially available (New England Biolabs, Beverly, Mass.; Stratagene, La Jolla, Calif.).

Many vectors may be used for the expression vectors or libraries of the invention that provide for the selection and expression of binding agents in yeast. Such vectors include, but are not limited to, plasmids and yeast artificial chromosomes. Preferably the vector has two replication systems, thus allowing it to be maintained, for example, in yeast for expression and in a prokaryotic host for cloning and amplification. Examples of such yeast-bacteria shuttle vectors include YEp24 (Botstein, et al., *Gene*, 8:17 (1979)), pCl/1 (Brake et al., *Proc. Natl. Acad. Sci. USA*, 81:4642 (1984)), and YRp17 (Stinchcomb et al., *J. Mol. Biol.*, 158:157 (1982)).

An expression vector may also be integrated into the yeast genome with an integrating vector. Integrating vectors usually contain at least one sequence homologous to a yeast chromosome that allows the vector to integrate, and preferably contain two homologous sequences flanking an expression cassette of the invention. Integrations appear to result from recombination events between homologous DNA in the vector and the yeast chromosome. (Orr-Weaver et al., *Methods in Enzymol.*, 101:228 (1983)). An integrating vector may be directed to a specific locus in yeast by selecting the appropriate homologous sequence for inclusion in the vector. One or more expression cassettes may integrate, which may affect the level of recombinant protein produced. (Rine et al., *Proc. Natl. Acad. Sci. USA*, 80:6750 (1983)). The chromosomal sequences included in the vector can occur either as a single segment in the vector, which results in the integration of the entire vector, or two segments homologous to adjacent segments in the chromosome and flanking an expression cassette included in the vector, which can result in the stable integration of only the expression cassette.

Extrachromosomal and integrating expression vectors may contain selectable markers that allow for selection of yeast strains that have been transformed. Selectable markers may include, but are not limited to, biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a selectable marker may also provide yeast with the ability to grow in the presence of toxic compounds, such as metal. For example, the presence of CUP1 allows yeast to grow in the presence of copper ions. (Butt et al., *Microbiol. Rev.*, 51:351 (1987)).

Many vectors have been developed for transformation into many yeasts. For example, vectors have been developed for the following yeasts: *Candida albicans* (Kurtz et al., *Mol. Cell. Biol.*, 6:142 (1986)), *Candida maltose* (Kunze et al., *J. Basic Microbiol.*, 25:141 (1985)), *Hansenula polymorpha* (Gleeson et al., *J. Gen. Microbiol.*, 132:3459 (1986); Roggenkamp et al., *Mol. Gen. Genet.*, 202:302 (1986), *kluyveromyces fragilis* (Das et al., *J. Bacteriol.*, 158: 1165 (1984)), *Kluyveromyces lactis* (De Louvencourt et al., *J. Bacteriol.*, 154:737 (1983); van den Berg et al., *Bio/Technology*, 8:135 (1990)), *Pichia guillerimondii* (Kunze et al., *J. Basic Microbiol.*, 25:141 (1985)), *Pichia pastoris* (Cregg et al., *Mol. Cell. Biol.*, 5: 3376, 1985; U.S. Pat. Nos. 4,837,148 and 4,929,555), *Saccharomyces cerevisiae* (Hinnen et al., *Proc. Natl. Acad. Sci. USA*, 75:1929 (1978); Ito et al., *J. Bacteriol.*, 153:163 (1983)), *Schizosaccharomyces pombe* (Beach and Nurse, *Nature*, 300:706 (1981)), and *Yarrowia lipolytica* (Davidow et al., *Curr. Genet.*, 10:39 (1985); Gaillardin et al., *Curr. Genet.*, 10:49 (1985)).

Baculovirus vectors have been developed for infection into several insect cells and may be used to produce nucleic acid constructs that encode a binding agent polypeptide of the invention. For example, recombinant baculoviruses have been developed for *Aedes aegypti*, *Autographa californica*, *Bombyx mori*, *Drosophila melanogaster*, *Spodoptera frugiperda*, and *Trichoplusia ni* (PCT Pub. No. WO 89/046699; Carbonell et al., *J. Virol.*, 56:153 (1985); Wright, *Nature*, 321: 718 (1986); Smith et al., *Mol. Cell. Biol.*, 3: 2156 (1983); and see generally, Fraser et al., *In Vitro Cell. Dev. Biol.*, 25:225 (1989)). Such a baculovirus vector may be used to introduce an expression cassette into an insect and provide for the expression of a binding agent polypeptide within the insect cell.

Methods to form an expression cassette of the invention inserted into a baculovirus vector are available in the art. Briefly, an expression cassette of the invention is inserted into a transfer vector, usually a bacterial plasmid that contains a fragment of the baculovirus genome, through use of common recombinant methods. The plasmid may also contain a polyhedrin polyadenylation signal (Miller et al., *Ann. Rev. Microbiol.*, 42:177 (1988)) and a prokaryotic selection marker, such as ampicillin resistance, and an origin of replication for selection and propagation in *Escherichia coli*. A convenient transfer vector for introducing foreign genes into AcNPV is pAc373. Many other vectors, known to those of skill in the art, have been designed. Such a vector is pVL985 (Luckow and Summers, *Virology*, 17:31 (1989)).

A wild-type baculoviral genome and the transfer vector having a nucleic acid construct of the invention are transfected into an insect host cell where the vector and the wild-type viral genome recombine. Methods for introducing a nucleic acid construct into a desired site in a baculovirus virus are available in the art. (Summers and Smith, Texas Agricultural Experiment Station Bulletin No. 1555, 1987. Smith et al., *Mol. Cell. Biol.*, 3:2156 (1983); and Luckow and Summers, *Virology*, 17:31 (1989)). For example, the insertion can be into a gene such as the polyhedrin gene, by homologous double crossover recombination; insertion can also be into a restriction enzyme site engineered into the desired baculovirus gene (Miller et al., *Bioessays*, 4:91 (1989)).

The packaged recombinant virus is expressed and recombinant plaques are identified and purified. Materials and methods for baculovirus and insect cell expression systems are commercially available in kit form. (Invitrogen, San Diego, Calif., USA ("MaxBac" kit)). These techniques are generally known to those skilled in the art and fully described in Summers and Smith, Texas Agricultural Experiment Station Bulletin No. 1555, 1987.

Plasmid-based expression systems have also been developed that may be used to introduce a nucleic acid construct of the invention into an insect cell and produce a binding agent polypeptide. (McCarroll and King, *Curr. Opin. Biotechnol.*, 8:590 (1997)). These plasmids offer an alternative to the production of a recombinant virus for the production of binding agent polypeptides.

A nucleic acid construct, an expression vector or a library of the invention may be inserted into any mammalian vectors that are known in the art or that are commercially available. (CLONTECH, Carlsbad, Calif.; Promega, Madision, Wis.; Invitrogen, Carlsbad, Calif.). Such vectors may contain additional elements such as enhancers and introns having functional splice donor and acceptor sites. Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papovaviruses, such as SV40 (Gluzman, *Cell*, 23:175 (1981)) or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification. Examples of such mammalian-bacteria shuttle vectors include pMT2 (Kaufman et al., *Mol. Cell. Biol.*, 2:946 (1989)) and pHEBO (Shimizu et al., *Mol. Cell. Biol.*, 6:1074 (1986)).

The invention is directed to cells that contain a library of the invention, an expression vector or a nucleic acid of the invention. Such cells may be used for expression of a binding agent polypeptide. Such cells may also be used for the amplification of nucleic acid constructs. Many cells are suitable for amplifying nucleic acid constructs and for expressing binding agent polypeptides. These cells may be prokaryotic or eukaryotic cells.

In many embodiments, bacteria are used as host cells. Examples of bacteria include, but are not limited to, Gram-negative and Gram-positive organisms. *Escherichia coli* is a desirable organism for screening libraries, expressing binding agent polypeptides and amplifying nucleic acid constructs. Many publicly available *E. coli* strains include K-strains such as MM294 (ATCC 31, 466); X1776 (ATCC 31, 537); KS 772 (ATCC 53, 635); JM109; MC1061; HMS174; and the B-strain BL21. Recombination minus strains may be used for nucleic acid construct amplification to avoid recombination events. Such recombination events may remove concatamers of open reading frames as well as cause inactivation of a nucleic acid construct. Furthermore, bacterial strains that do not express a select protease may also be useful for expression of binding agent polypeptides to reduce proteolytic processing of expressed polypeptides. One example of such a strain is Y1090hsdR that is deficient in the lon protease.

Eukaryotic cells may also be used to produce a binding agent polypeptide and for amplifying a nucleic acid construct. Eukaryotic cells are useful for producing a binding agent polypeptide when additional cellular processing is desired. For example, a binding agent polypeptide may be expressed in a eukaryotic cell when glycosylation of the polypeptide is desired. Examples of eukaryotic cell lines that may be used include, but are not limited to: AS52, H187, mouse L cells, NIH-3T3, HeLa, Jurkat, CHO-K1, COS-7, BHK-21, A-431, HEK293, L6, CV-1, HepG2, HCl 1, MDCK, silkworm cells, mosquito cells, and yeast.

Methods for introducing exogenous DNA into bacteria are available in the art, and usually include either the transformation of bacteria treated with $CaCl_2$ or other agents, such as divalent cations and DMSO. DNA can also be introduced into bacterial cells by electroporation, use of a bacteriophage, or ballistic transformation. Transformation procedures usually vary with the bacterial species to be transformed (Masson et al., *FEMS Microbiol. Lett.*, 60:273 (1989); Palva et al., *Proc. Natl. Acad. Sci. USA*, 79:5582 (1982); EPO Publ. Nos. 036 259 and 063 953; PCT Publ. No. WO 84/04541 [*Bacillus*], Miller et al., *Proc. Natl. Acad. Sci. USA*, 8:856 (1988); Wang et al., *J. Bacteriol.*, 172:949 (1990) [*Campylobacter*], Cohen et al., *Proc. Natl. Acad. Sci. USA*, 69:2110 (1973); Dower et al., *Nuc. Acids Res.*, 16:6127 (1988); Kushner, "An improved method for transformation of *Escherichia coli* with ColE1-derived plasmids", in: Genetic Engineering: Proceedings of the International Symposium on Genetic Engineering (eds. H. W. Boyer and S, Nicosia), 1978; Mandel et al., *J. Mol. Biol.*, 53:159 (1970); Taketo, *Biochim. Biophys. Acta*, 949: 318 (1988) [*Escherichia*], Chassy et al., *FEMS Microbiol. Lett.*, 44:173 (1987) [*Lactobacillus*], Fiedler et al., *Anal. Biochem*, 170:38 (1988) [*Pseudomonas*], Augustin et al., *FEMS Microbiol. Lett.*, 66:203 (1990) [*Staphylococcus*], Barany et al., *J. Bacteriol.*, 144:698 (1980); Harlander, "Transformation of *Streptococcus* lactis by electroporation", in: Streptococcal Genetics (ed. J. Ferretti and R. Curtiss III), 1987; Perry et al., *Infec. Immun.*, 32:1295 (1981); Powell et al., *Appl. Environ. Microbiol.*, 54:655 (1988); Somkuti et al., *Proc. 4th Eur. Cong. Biotechnology*, 1:412 (1987) [*Streptococcus*].

Methods for introducing exogenous DNA into yeast hosts are also available in the art, and usually include either the transformation of spheroplasts or of intact yeast cells treated with alkali cations. Transformation procedures usually vary with the yeast species to be transformed (Kurtz et al., *Mol. Cell. Biol.*, 6:142 (1986); Kunze et al., *J. Basic Microbiol.*, 25:141 (1985) [*Candida*], Gleeson et al., *J. Gen. Microbiol.*, 132:3459 (1986); Roggenkamp et al., *Mol. Gen. Genet.*, 202: 302 (1986) [*Hansenula*], Das et al., *J. Bacteriol.*, 158:1165 (1984); De Louvencourt et al., *J. Bacteriol.*, 754:737 (1983); Van den Berg et al., *Bio/Technology*, 8:135 (1990) [*Kluyveromyces*], Cregg et al., *Mol. Cell. Biol.*, 5:3376 (1985); Kunze et al., *J. Basic Microbiol.*, 25:141 (1985); U.S. Pat. Nos. 4,837, 148 and 4,929,555 [*Pichia*], Hinnen et al., *Proc. Natl. Acad. Sci. USA*, 75:1929 (1978); Ito et al., *J. Bacteriol.*, 153:163 (1983) [*Saccharomyces*], Beach and Nurse, *Nature*, 300:706 (1981) [*Schizosaccharomyces*], and Davidow et al., *Curr. Genet.*, 10:39 (1985); Gaillardin et al., *Curr. Genet.*, 10:49 (1985) [*Yarrowia*]).

Exogenous DNA is conveniently introduced into insect cells through use of recombinant viruses, such as the baculoviruses described herein.

Methods for introduction of heterologous polynucleotides into mammalian cells are known in the art and include lipid-mediated transfection, dextran-mediated transfection, calcium phosphate precipitation, polybrene-mediated transfection, protoplast fusion, electroporation, encapsulation of the polynucleotide(s) in liposomes, biollistics, and direct microinjection of the DNA into nuclei. The choice of method depends on the cell being transformed as certain transformation methods are more efficient with one type of cell than another. (Felgner et al., *Proc. Natl. Acad. Sci.*, 84:7413 (1987); Felgner et al., *J. Biol. Chem.*, 269:2550 (1994); Graham and van der Eb, *Virology*, 52:456 (1973); Vaheri and Pagano, *Virology*, 27:434 (1965); Neuman et al., *EMBO J.*, 1:841 (1982); Zimmerman, *Biochem. Biophys. Acta.*, 694: 227 (1982); Sanford et al., *Methods Enzymol.*, 217:483 (1993); Kawai and Nishizawa, *Mol. Cell. Biol.*, 4:1172 (1984); Chaney et al., *Somat. Cell Mol. Genet.*, 12:237 (1986); Aubin et al., *Methods Mol. Biol.*, 62:319 (1997)). In addition, many commercial kits and reagents for transfection of eukaryotic cells are available.

Following transformation or transfection of a nucleic acid into a cell, the cell may be selected for the presence of the nucleic acid through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes that render the recipient host cell resistant to drugs such as actinomycin Cl, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. (Davies et al., *Ann. Rev. Microbiol.*, 32: 469 (1978)). Selectable markers may also include biosynthetic genes, such as those in the histidine, tryptophan, and leucine biosynthetic pathways. Upon transfection or transformation of a host cell, the cell is placed into contact with an appropriate selection agent.

For example, if a bacterium is transformed with a nucleic acid construct that encodes resistance to ampicillin, the transformed bacterium may be placed on an agar plate containing ampicillin. Thereafter, cells into which the nucleic acid construct was not introduced would be prohibited from growing to produce a colony while colonies would be formed by those bacteria that were successfully transformed. An analogous system may be used to select for other types of cells, including both prokaryotic and eukaryotic cells.

Accordingly, the invention is directed to methods for generating and screening a library of binding agent polypeptides through molecular substitution and manipulation of vectors comprising a nucleic acid that encodes a generic binding agent polypeptide.

Computer Design of Binding Agents

The invention also provides methods for identifying binding agent polypeptides by screening a "virtual" library of random binding agents. The developed computer screening method is an alternative (or parallel) route to the actual library construction and screening procedures described above.

The computer screening method generally involves using the known three-dimensional structure of the target (or "antigen") as a starting point, and fitting the target structure, first, into a parental or generic binding agent, and then progressively optimizing the loop contact sequences (i.e. the functional amino acids) in the binding agent in order to maximize favorable binding reactions.

Libraries of binding agent polypeptides can then be generated by the present computer screening methods to provide a multitude of binding agents that can interact with a selected target molecule. Specific sites or sequences within the target molecule (i.e. a search zone) can be targeted for interaction with the binding agent polypeptides provided by the libraries.

Figure 10:
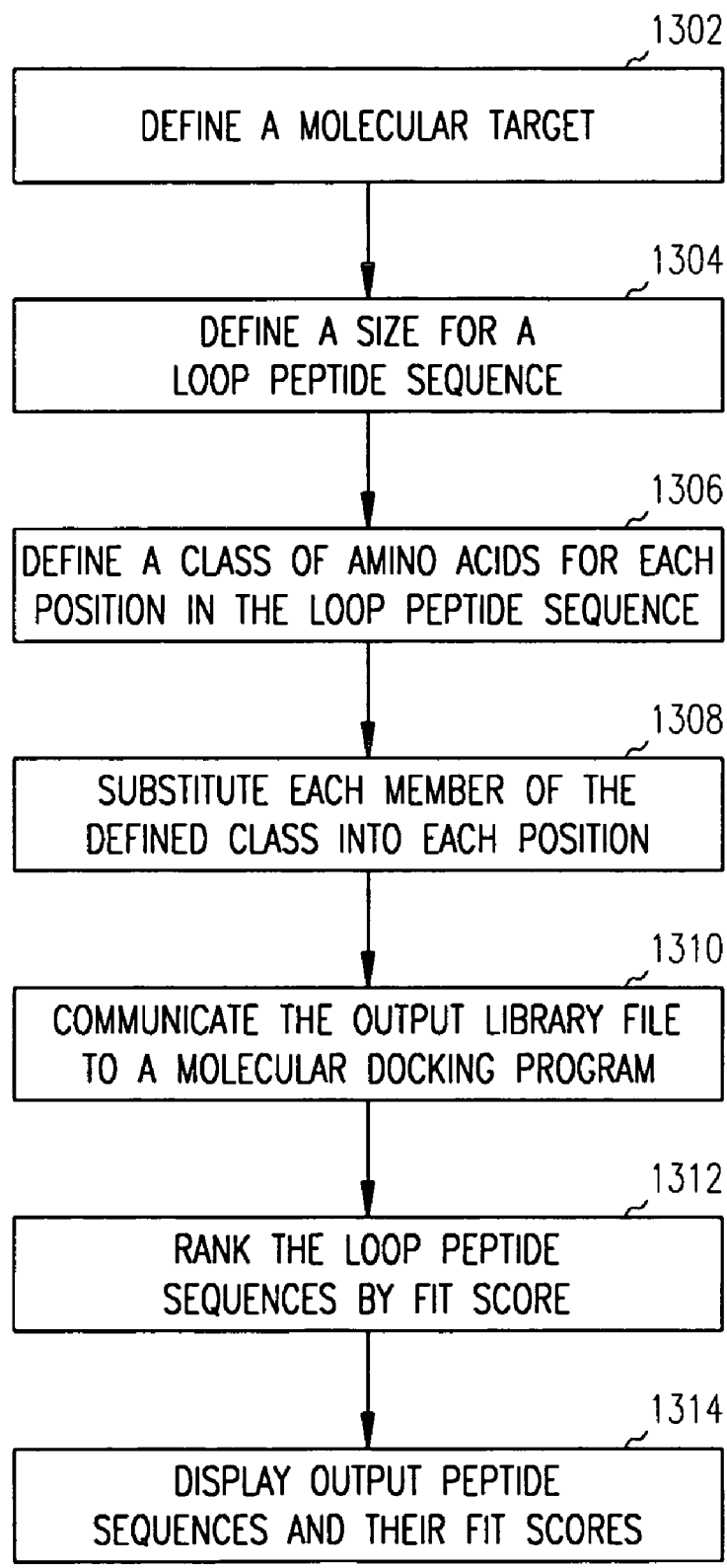
FIG. 10 is a flowchart depicting a program to automatically discover new binding reagents against specific target molecules.

A generalized diagram of the computer screening method of the invention is provided in FIG. 10. A first step in the method is to define a molecular target 1302. Such a molecular target is a target molecule to which a binding agent polypeptide can interact. The interactive loops of the binding agent will bind or interact with the target molecule. Defining the target molecule involves entering data on the three-dimensional structure of the target, for example, the spatial organization and atomic coordinates of each atom within the target molecule that is expected to interact with the binding agent.

One of skill in the art can select any target protein, carbohydrate or nucleic acid of interest. For example, the target protein can be an antigen, an antibody, an enzyme, a hormone, a receptor, a ligand, a DNA-binding protein, a membrane-associated protein, or any structural protein. Examples of input or target nucleic acid sites to which the binding agent polypeptides of the library can bind include promoters, enhancers, polyadenylation sites, introns, splicing signals, termination signals, and translation leader sequences.

Rather than defining the entire structure of the target, a target search zone on the target molecule can be defined. Such a search zone defines the physical and chemical properties of the site to which the binding agent will interact or bind. For example, the search zone can contain the x, y and z coordinates of all atoms in the selected interaction site on the target molecule. Other parameters that may be considered in defining the search zone include the charge, hydrophilicity, hydrophobicity, distance and orientation of atoms within the input or target molecule.

Another step in the computerized methods of the invention includes defining a size for a loop peptide sequence 1304. As described herein, peptide loops can be a variety of lengths. For example, desirable loop peptides in the library can be about 1 to about 40 amino acids in length. In some embodiments, the loop peptides in the library can be about 2 to about 30 amino acids in length. In other embodiments, loop peptides in the library can be about 2 to about 20 amino acids in length. Some loop peptides in the library can be about 2 to about 15 amino acids in length. Desirable peptide loops in the library can also be about 2 to about 10 amino acids in length or about 2 to about 9 amino acids in length. These amino acids encode at least one loop interactive domain that will have binding affinity and specificity for a target molecule. Hence, while a variety of loop lengths can used, the size selected should not adversely affect the stability of the beta barrel core structure, for example, as analyzed by modeling studies, or long range molecular dynamics simulations. In one embodiment, the peptide length is about the length of the loop (i) to (v) sequences, that is, about 4 to about 7 amino acids.

A number of different loop peptide sequences can be screened for interaction with slightly different regions on the target molecule. Such screening can be done simultaneously or sequentially. In some embodiments the screening of different loop sequences is done sequentially by defining an optimized sequence for a first loop sequence, orienting the target molecule and binding agent to permit optimum interaction between the defined loop sequence and the target molecule and then defining the amino acid sequence for another loop. In this manner the interaction of target and binding agent becomes progressively more defined and somewhat fewer docking interactions need to be performed.

Figure 6:
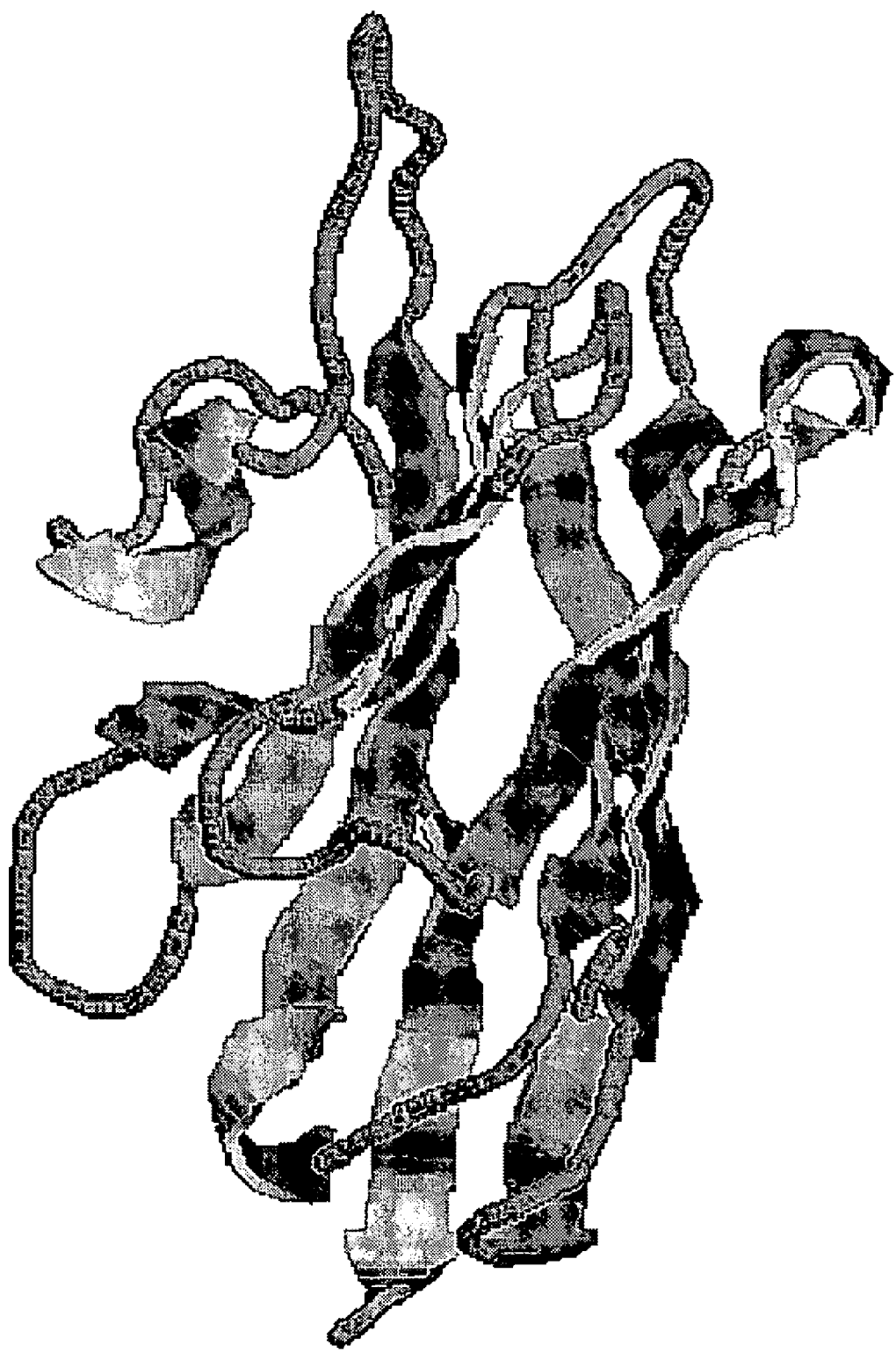
FIG. 6 illustrates the three dimensional structure of the parental binding reagent. The structure is defined by five loops (depicted by thin tubular strands), which are the primary target recognition elements. The overall topology is a beta sandwich (depicted by arrows) stabilized by a central disulfide bond (not shown). The protein sequence ends with a tail that can be used to anchor the molecule on the surface of a bead or other surface for use in diagnostic devices. The target contact region is solely defined by the spatial orientation of these loops.

When considering the target search zone, one of skill in the art may take the three dimensional structure of the generic binding agent into consideration. This is because the positioning of the loop peptide sequences on the target is determined to a large extent by the position of those loops on the parental or generic binding agent (see, e.g., SEQ ID NO:2, SEQ ID NO:37, SEQ ID NO:38 and FIG. 6). The generic or parental binding agent has 134 amino acids, with a total molecular weight of 12.8 kDa. FIG. 6 illustrates the three dimensional structure of the parental binding agent. The overall topology of the binding agents is that of a beta sandwich (depicted by arrows) stabilized by a central disulfide bond (not shown). The five loops that provide the binding site of these agents are shown as thin strands that connect the arrows.

A three dimensional model of the generic binding agent polypeptide was prepared by threading the amino acid sequence (SEQ ID NO:38) onto the three dimensional alpha carbon backbone of a camelid antibody (structure 1jtt.ent in the Protein Databank) using the program SwissModel. The optimal thread result was converted into a three dimensional structure that included amino acid side chain positions using the program ProMod. This initial model was subjected to a round of simulated annealing in order to minimize side chain clashes. Several rounds of a SYBYL® level geometry optimization put all dihedral angles and torsions into proper geometry. A final round of energy minimization using a GROMOS96 parameter set, without a reaction field, was employed. Hence, the amino acid sequence provided for the generic binding agent has been optimized to provide a highly stable beta barrel conformation.

An additional step that may be included in the method is to define a class of amino acids for each position in the amino acid sequence of the loop peptide 1306. In many embodiments, one of skill in the art may select all amino acids, for example, all twenty naturally occurring amino acids. All amino acid residues can then be placed within the allowable Ramachandran space to examine the fit for optimal steric and chemical interactions.

However, one of skill in the art may also choose to utilize distinct chemical and physical classes of amino acids at different positions within the loop peptides. Hence, amino acids having related physical structures, or having specified chemical properties, or having specified solubility properties can form the class of amino acids that is used at specified positions within the loop sequence. One of skill in the art can select how many amino acid substitutions can occur at each position of the loop peptides. Similarly, the user can select any combination of amino acids to place at a given position within the loop peptide(s).

For example, the skilled artisan can select any class or type of amino acid to be placed at a given position. Such a class of amino acids can, for example, be a class of genetically encoded L-amino acids, naturally occurring non-genetically encoded L-amino acids, synthetic L-amino acids, D-enantiomers of genetically encoded amino acids, D-enantiomers of naturally occurring non-genetically encoded amino acids, or synthetic D-amino acids. Other classes of amino acids include hydrophilic amino acids, hydrophobic amino acids, cysteine-like amino acids, acidic amino acids, basic amino acids, polar amino acids, aromatic amino acids, apolar amino acids or aliphatic amino acids. Further examples of types and classes amino acids are provided hereinabove.

In another step, each member of the class of amino acids can be iteratively substituted or placed into the prescribed position of the loop peptide to generate an output library file 1308. Such an output library file contains a plurality of output loop peptide sequences, each with a distinct peptide sequence.

An additional step that can be included in the method is to communicate the output library file to a molecular docking program 1310. Thus, the output library file is used as input to a docking program that fits each loop peptide to the search zone on the target molecule. Amino acids within each loop of the generic binding agent are then fitted to the molecular structure of the target molecule.

The molecular docking program can fit each of the plurality of output loop peptide sequences to the search zone and then to create a binding loop-target molecule fit score. Such a binding loop-target molecule fit score is a measure of how well a given loop peptide sequence will interact with, bind to or fit within the search zone of a target molecule. Peptide loops having a binding loop-target molecule fit score will generally interact, bind or fit well with the chosen site in the target molecule.

In another step of the method, the plurality of output loop peptide sequences can be ranked by binding loop-target molecule fit score 1312. Such a ranking permits ready assessment of which loop peptides will most effectively interact, bind or fit the chosen site in the target molecule.

An additional step that can be included in the method is to display each of the plurality of output loop peptide sequences and the associated binding loop-target molecule fit score 1314. At least a portion of the plurality of output loop peptide sequences can stably interact with the target molecule. Accordingly, one of skill in the art may choose to list all output loop peptide sequences.

Alternatively, rather than listing all possible loop peptide sequences with their associated fit scores, only a percentage of the top-scoring loop peptides can be displayed. Such a percentage is inputted before or during the analysis. Alternatively, the program may randomly pick a certain percentage of all the possible loop peptide sequences to write out to the final structure file. Selection of such a percentage can limit the size of the output library file size and/or the complexity of the final loop sequences.

In one embodiment, a program, called MKBIND, was written in FORTRAN 77 that can be used to automatically identify loop amino acid sequences that bind to specific target molecules. The code was compiled to run under LINUX on a Rocketcalc, LLC Beowulf computing cluster. Parallelization of the code results in a significant speed-up in search time.

Figure 8:
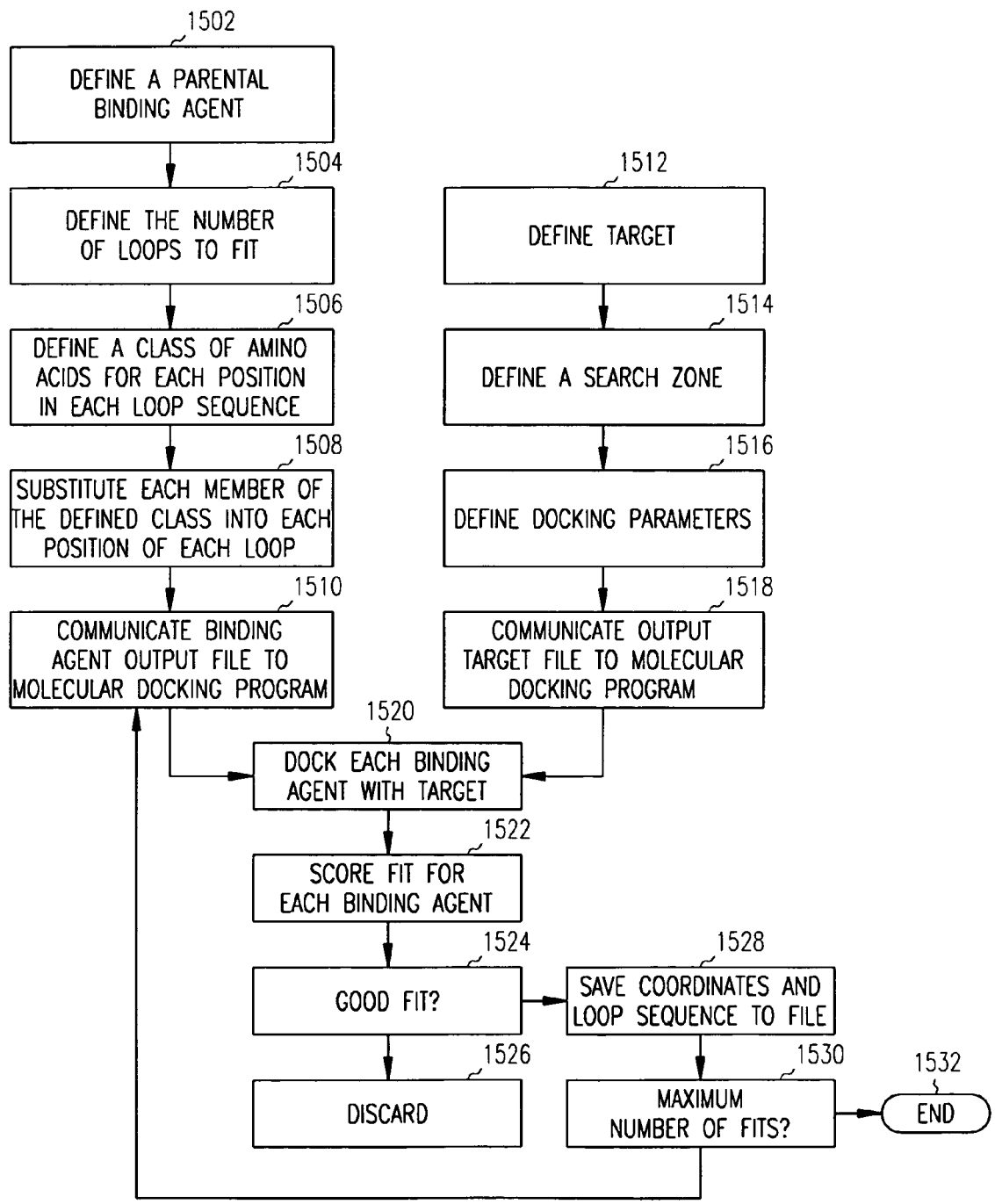
FIG. 8 is a flowchart depicting a program to automatically discover new binding reagents against specific target molecules.

A flowchart for the general program flow of MKBIND is shown in FIG. 8. The MKBIND program flow begins with definition of the parental binding agent 1502 and the target 1512. Information relating to the three-dimensional structures of the parental binding agent and the target molecule is entered as two different data files. Such information includes the atomic coordinates of all atoms in the parental or generic binding agent (e.g. SEQ ID NO:2, SEQ ID NO:4 or SEQ ID NO:38) and in the target molecule.

A specific search zone on the target may be selected and defined 1514. Such a search zone can be used, for example, when a specific site or "epitope" is selected for binding, or when the target is very large so that binding interactions are examined in only selected areas of the target. The search zone for the target search can be defined manually by one of skill in the art. In some embodiments, a portion of the target molecule is selected by picking an identifiable center of gravity (or an identifiable structural area such as a box or triangle or coordinates) that can be centered over a selected atomic coordinate within the target molecule. In some embodiments, the depth of the identifiable center (box or triangle) projects about 1 Å to about 5 Å (or about 3 Å) from the average surface in the center to about the same distance below that level (to get the deeper grooves). A typical search area can be, for example, about 20 Å×20 Å×6 Å.

The docking parameters or other criteria 1516 are then entered, including such variables as a choice of forcefield, electrostatic constraints, grid location, grid spacing, energetic cutoff criteria, and the like. The docking parameters with the target definition and/or search zone constitute an output target file.

The loop structures in the binding agent are initially undefined. The user will also input the number of loops to simultaneously randomize 1504, that is, a user can pick any or all loops for searching. Classes of amino acids or other amino acid constraints 1506 are picked for the loops that are to be searched. All twenty naturally occurring amino acids can be searched at each position, or a subset of amino acids (e.g. hydrophobic amino acids) can be searched at selected positions.

Once the loop amino acids are defined, the program creates an atomic coordinate file of that loop. The program generates all the coordinate files for all loops of the size and type of amino acid defined by the user 1508. For example, if degenerate loops are chosen, the program generates degenerate loops containing all combinations of amino acids along the entire length of the loop(s). The program can also apply a simple coordinate transformation to anchor the new loop into the binding agent structure. The program also defines where the ends of the loops need to be in the parental structure.

Hence, each member of the defined classes of amino acids is substituted into each position of each loop 1508 to generate a binding agent output file which comprises a series of files containing structural coordinates for all possible binding agents with all possible loop sequences.

The binding agent output file and the output target file are then communicated to the docking program 1510, 1518. The binding agent output file 1510 can be a regular atomic coordinate file. The output target file 1518 can be a file that defines the atomic coordinates of the amino acid residues in the grid area, as well as the xyz coordinates of the grid itself. All three-dimensional structures are used by MKBIND as atomic coordinate files. Such three-dimensional structures measure bond distances and energies between the loops (i to v) and the amino acid side chains in the defined grid region.

The molecular docking program docks each binding agent with the target using a flexible docking algorithm 1520. The program rotates and translates the coordinates of the binding agent relative to the fixed coordinates of the target molecule, thereby changing the three-dimensional coordinates of the binding agent as it is rotated about the center of mass of the target agent and translating these coordinates along one axis at a time.

Hence, after the binding loops are generated, the resulting structure is placed in the geometric center of the search grid. Functionally this means that the loop-binding surface of the binding agent is centered within the volume of the coordinate grid of the target molecule. The binding agent is then moved towards the target surface (still within the grid) along one axis in 0.1 A intervals, and a fit score is calculated. The structure is then moved another 0.1 A. If the fit score has improved by such movement, the binding agent is moved further in until the score gets worse. At that point it is moved out by 0.1 A (to the last best score) and is then it is moved up in the same manner, then down, and then left and right. All such movement and resetting of position, results in the "optimal locale for the fit."

A docking score or fit score for each binding agent variant is then computed 1522. The fit score is the negative value of the non-bonded inter-molecular energy between the binder and the target. For example, the fit score can be calculated as described below.

$$\text{Fit score} = -[E_{elect} + E_{vdw} + E_{HB}]$$

where $E_{elect}$ is the electrostatic energy, $E_{vdw}$ is the Van der Waals term and $E_{HB}$ is the hydrogen bond energy. This empirical energy function is a summation of these three individual energy terms:

$$\sum \frac{q_i q_j}{4\pi\varepsilon_0 r} + \sum \left(\frac{A_{ij}}{r_{ij}^{12}} - \frac{B_{ij}}{r_{ij}^{6}}\right) + \sum \left(\left(\frac{A}{r_{AD}^{6}} - \frac{B}{r_{A}^{4}}\right)\right) \cos(\theta_{A-H-D})$$

A good fit score is a positive nonzero number and can, for example, be the highest fit score. If the fit is a high, or top score 1524, the loop sequences and the binding agent variant coordinate file are saved 1528. If the fit is poor, the loop sequences and the binding agent variant coordinate file are discarded 1526. The top N sequences constitute an output that can be further analyzed if the user so chooses. This sequence of operations can thus be repeated until either all of the requested randomizations are complete or a user-defined number of fits is reached 1530 at which point the program ends 1532.

Once the best fit is found the binder coordinate file is written out. The coordinates are transformed to reflect the target atomic coordinates so that the user can pull up the target and the binder on the screen and see (and inspect) the fit. If more than one loop is searched, a second file is listed that provides the amino acid sequence of the different loops and the associated fit score. This allows one of skill in the art to do a primary sequence analysis to see what type of amino acids are favored in certain positions. This information can be used to help constrain the amount of brute force searching performed. Hence, for example, if a cysteine is often found in position 3 of loop (i) one of skill in the art can lock cysteine into position 3 at the start of the MKBIND program.

In order to save disk space, the optimal loop sequences can be generated one at a time so that the optimized loop sequences are inserted into the parental binding agent prior to docking the non-optimized loop sequences. A scoring function that gauges the robustness of the fit can be implemented. Coordinate files can be saved if they were the top scoring fit or a high scoring fit. All high scoring loop sequences can be provided as output for offline analysis (e.g. alignment).

The functions or algorithms described herein are implemented in software or, in one embodiment, a combination of software and human implemented procedures. The software comprises computer executable instructions stored on computer readable media such as memory or other type of storage devices. The term "computer readable media" is also used to represent carrier waves on which the software is transmitted. Further, such functions correspond to modules, which are software, hardware, firmware of any combination thereof. Multiple functions are performed in one or more modules as desired, and the embodiments described are merely examples. The software is executed on a digital signal processor, ASIC, microprocessor, or other type of processor operating on a computer system, such as a personal computer, server or other computer system.

Figure 11:
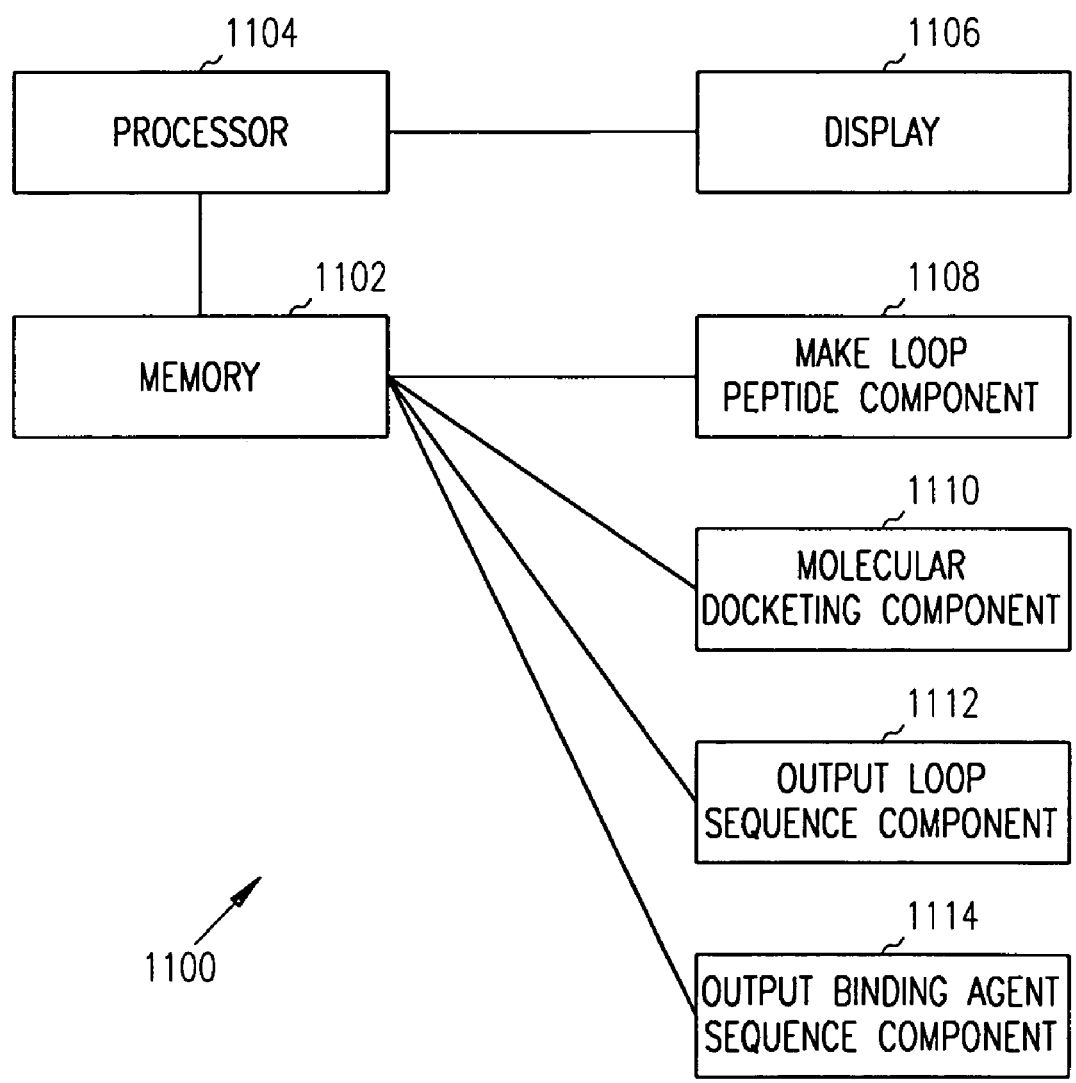
FIG. 11 is a schematic diagram of a system for creating binding agents with different loop peptide sequences.

In another embodiment, the invention also relates to a system (1100) for creating binding agent with different loop peptide sequences (see FIG. 11). Such a system can include processor 1104. A memory 1102 and/or a display 1106 can be coupled to the processor. The system can also include a make loop peptide sequence component 1108 capable of executing on the processor to generate peptide sequences. The system can also include a molecular docking component 1110 capable of executing on the processor to fit binding agent or loop structures together with target structures. The system can also include an output loop peptide sequence component 1112 capable of executing on the processor to display loop peptide sequences. Other components can also be included such as an output binding agent component 1114 capable of executing on the processor to displaying binding agent sequences, particularly top scoring binding agent sequences.

A processor, such as a microprocessor in a Personal Computer (PC) is the logic circuitry that responds to and processes the basic instructions that drive a computing device. Computing devices include PCs, laptops, general purpose computers, and the like. A memory is the electronic holding place for instructions and data accessible to a computing device. During normal operation, memory usually contains an operating system, application programs, and data. Kinds of memory include random access memory (RAM), read-only memory (ROM), programmable memory (PROM), and erasable programmable ROM (EPROM) as well as storage devices such as hard drives and floppy disks. A display is a computer output mechanism that shows text and often graphic images to the computer user. Examples of displays include printers, monitors, and the like.

In another embodiment, the invention is directed to a machine-accessible medium having associated content capable of directing the machine to perform a method. The method can be one of the methods described above, for example, one of the methods illustrated in FIG. 8 or 10 that are further described above.

The MKBIND program described above has been used to construct a novel binding agent that was capable of binding to bovine trypsin. The starting three-dimensional structures of a generic parental binding agent (e.g., SEQ ID NO:38, see FIG. 12) and bovine trypsin (PDB code 1auj.ent) were used as input. The computer screening method identified a top scoring loop variant binding agent having a loop i sequence of ITAVCHK (SEQ ID NO:35). An actual binding agent polypeptide was constructed by inserting this i sequence into the parental binding agent. The binding agent variant was then expressed and purified. This modified binding agent was tested and was found to have affinity for the target molecule (bovine trypsin).

Hence, the camel single domain antibody fragment has been modulated and improved using site directed mutagenesis to create a generic binding agent that can easily be further adapted to generate binding agent with high affinity for specific target molecules. The screening methods of the invention allows workers to increase the affinity, to alter the specificity, or to modify the biophysical characteristics of binding agents that are produced through modern recombinant DNA techniques. The screening methods of the invention also allow quick and efficient target ("antigen") screening to find the best binding agent for a variety of targets, including such toxic targets as anthrax, botulism toxin, ricin, and other agents that are dangerous to handle.

The behavior of binding agents obtained by the molecular manipulation and computer mediated methods can be further evaluated by methods available to one of skill in the art. For example, the binding agents obtained by the methods of the invention can be evaluated for stability, binding affinity and other such properties. The ability of the binding agents to bind one or more selected targets, or not bind components that may be present in a binding assay, can be evaluated by standard tests for binding interactions. For example, binding interactions can be detected and evaluated by non-denaturing gel chromatography, by non-denaturing polyacrylamide gel electrophoresis, by isothermal titration calorimetry (ITC), or by adaptation of any available immunoassay procedure. Such immunoassay procedures are further described below.

Methods of Use

The present invention also relates to diagnostic assays and methods, both quantitative and qualitative for using the binding agents described herein. According to the invention, the binding agents can be used in any assay or procedure that is currently performed using antibodies by employing the present binding agents instead of the antibodies. The binding agents can also be modified to include a reporter molecule or other molecule that can facilitate employment of the binding agents in such assays or procedures.

The binding agents of the invention can be used to bind, detect or identify any target. Such a target is any molecule that can be characterized as an antigen or an antigenic epitope. Hence, targets can be proteins, peptides, carbohydrates, lipoproteins, proteoglycans, enzymes, hormones, mammalian antigens, bacterial antigens, fungal antigens or viral antigens. Bacterial, fungal or viral targets include essentially any single cell organism or parasite that that is of interest to one of skill in the art. Such organisms include bacteria, fungi, yeast strains and other single cell organisms such as, for example, Human Immunodeficiency Virus (HIV) antigens, Hepatitis virus antigens (HCV, HBV, HAV), Ebola virus antigens, influenza virus antigens, *Toxoplasmosis gondii* antigens, Cytomegalovirus antigens, *Helicobacter pylori* antigens, Rubella antigens, and the like.

Targets are generally in solution or can be placed in solution prior to use with the present binding agents. When a specific preparation of binding agents is used, the target need not be in the form of a pure solution. Instead, target can be impure and the binding agent can be used to detect or isolate the target.

The binding agents of the invention can be used to detect or isolate a target in any convenient sample suspected of containing the target. Such samples include clinical samples, biological fluids, tissue samples (that are, for example, homogenized) and the like. Samples can include soil, air, water, and other materials obtained from the environment. Bacterial proteins, viral proteins, plant tissues, animal tissues, animal fluids and the like can also be utilized as samples to be tested or used with the binding agents of the invention. Samples also include biological samples such as cells, blood, plasma, serum, urine, mucus, tissue, cellular or tissue homogenates and the like.

In some embodiments, the sample may be diluted prior to testing or exposure to the binding agent. Dilution can proceed by addition of any fluid compatible with each of the samples to be tested and the binding agents to be used. Serum, when used as the sample, can, for example, be diluted with one or more fluids selected from the group consisting of phosphate-buffered saline, pH 7.0-7.4 (hereinafter, "PBS"), PBS-containing TWEEN 20™ (hereinafter, "PBS T"); PBS T with thimerosal (hereinafter, "PBS TT"), PBS TT with gelatin (hereinafter, "PBS TTG"), and PBS TTG with bovine gamma globulin (hereinafter, "PBS TTGG"). Dilutions may vary as needed, for example, from about 1:10 to about 1:10,000.

The binding agents of the invention can be used in any immunoassay procedure known to one of skill in the. For example, such immunoassays can involve, one, two or even three of the present binding agents. The immunoassays can be performed in solution or on a substrate, for example, where the binding agent or target is bound to a solid surface. Examples of immunoassays that can be adapted for use with the present binding agents include ELISA assays, surface plasmin resonance assays, radioimmunoassays, immunohistochemical assays, and the like.

Appropriate pairs of binding agents for sandwich assays can be selected from among the various binding agent preparations of the invention. Such a binding agent pair comprises a first high affinity binding agent and a second high affinity binding agent. In "sequential" sandwich assays, an immobilized binding agent can be used to bind the target, the unbound portions of test sample are removed, the bound target is used to adsorb a second binding agent, and the bound and unbound material is then separated. The amount of bound second binding agent is directly proportional to the amount of target in the test sample. Binding agents of the invention need not be used only in "sequential" sandwich assays—they can be used advantageously in simultaneous sandwich assays that require fewer steps and little or no washing during the detection procedure. In a "simultaneous" sandwich assay, the test sample is not removed before adding the second binding agent.

In one embodiment, a surface plasmon resonance (SPR)-based sensor system is used. SPR is a useful tool for measuring the interactions between two or more molecules in real time without the use of any detection labels. See McDonnell, J. M. (2001) "Surface plasmon resonance towards an understanding of the mechanisms of biological molecular recognition" *Curr. Opin. Client. Biol.*, 5, 572-577.

SPR technology is based on an optical phenomenon, where the response depends on a change in refractive index in the near vicinity of the sensor chip surface employed and the response is proportional to the mass of analyte bound to the surface. SPR is able to continuously analyze every step of an interaction whereas other methods may not allow analysis of the results until the final step is completed. Continuous flow technology can therefore be utilized with the continuous monitoring system offered by SPR.

In general, SPR is used as follows. A selected binding agent preparation is immobilized on the sensor surface (substrate) and then the immobilized binding agent is contacted with a test solution that may contain a target to which the binding agent can bind. This test solution flows continuously over the sensor surface. The binding reaction between the immobilized binding agent and the target can be detected without addition of any further reagents. A second binding agent that is reactive with the target can be used for detection of a first complex formed between the immobilized binding agent and any target in the test solution. The SPR response or signal increases as more target, binding agent or target-binding agent complexes from the solution bind to the immobilized binding agent on the surface of the sensor. The binding reaction can be detected, for example, with a Biacore SPR instrument.

The SPR angle is sensitive to the composition of the layer at the gold surface of the biosensor chip. A baseline SPR response is therefore first determined by running a buffer over the surface of the binding agent-immobilized chip. The binding of target to one or two binding agents causes an increase in the refractive index at the surface, thereby changing the SPR angle because it is directly proportional to the amount of bound material. The affinities of interest are usually quite strong in biological systems, and targets with molecular weights greater than 200 daltons can usually be detected quite accurately. Generally, the SPR is a sensitive technique that requires smaller sample sizes and less run time than many other techniques.

SPR also allows monitoring of both association and dissociation phases during the binding agent-target interactions (Myszka, 1997; Ohlson et al, 1997). A typical sensorgram consists of a baseline signal (with no change in response units (RU) over time) and an association phase after sample injection, which produces an increase in response units over time. If the reaction rates are fast enough, it is possible to reach a steady state level, where the rates of association and dissociation are equal. Resumed buffer flow causes the complex to dissociate, and the kinetics of dissociation can be recorded. Thus, both association and dissociation kinetics can be measured. At a desired time, a regeneration solution can be injected to remove target molecules that are bound to the surface, and the original response unit value is re-established.

Several candidate binding agent preparations with good to excellent or high affinity for the target are therefore selected for use with the SPR immunoassays. From among the group of these high affinity binding agent preparations, at least one high affinity binding agent preparation is selected for immobilization to a suitable substrate.

The selected binding agent preparations are immobilized on a suitable substrate by any method available to one of skill in the art. The binding agent can be linked directly to a selected functional group on the substrate. Alternatively, the antibodies can be linked indirectly to the substrate via a linker or spacer.

For example, the selected binding agent can be immobilized via linkage to streptavidin (or biotin) and then attachment to the substrate via a biotin (or streptavidin) moiety that is covalently linked to the substrate. Alternatively, a multilayer of thin films of streptavidin/biotin can be used with an appropriate SPR substrate. A thin film of gold can be evaporated onto a substrate, and a layer of biotin can be immobilized onto the film. A monolayer of streptavidin is then immobilized onto the biotinylated gold surface. Streptavidin is a tetravalent protein obtained from *Streptomyces avidinii* that possesses four biotin-binding sites arranged in pairs on opposite faces of the molecule. Once the streptavidin film binds to the biotinylated gold surface, it can be used as a linking molecule to bind to a biotinylated binding agent. See Morgan, H. and D. M. Taylor, "A Surface Plasmon Resonance Immunosensor Based on the Streptavidin-Biotin Complex," Biosens. & Bioelect., 7, (1992), pages 405-410; Taylor, D. M., et al., "Characterization of Chemisorbed Monolayers by Surface Potential Measurements," J. Phys, D: Appl. Phys., 124, (1991), pages 443-450.

Alternatively, a thiol-terminal silane is used for coating of the substrate surface, and a heterobifunctional crosslinker, N-gamma-maleimidobutyryloxy succinimide ester (GMBS) is used for protein attachment. The thiol-terminal silane can be mercaptopropyl trimethoxysilane (MTS). The GMBS reacts at one end with thiol groups present on the silane coating, and at the other end with terminal amino groups of the binding agent. See U.S. Pat. No. 5,077,210. With this method, binding agents can be immobilized at a high density (e.g., 2 ng/mm$^2$). The amount of nonspecific binding to the substrate can be reduced to 2 to 5% of the total binding by addition of blocking agents (BSA, ovalbumin, sugars, dextran, etc.). With this low background, target binding can be measured at levels as low as 150 femtomoles when a target concentration of 3 picomoles/ml is applied. Binding agents immobilized by this method can maintain their bioactivity for significant periods of time.

After immobilization of a selected binding agent onto a suitable substrate, the reactivity of the immobilized binding agent with target can be tested to insure that binding agent-target affinity has not been adversely affected by immobilization of the binding agent on the sensor chip. SPR requires small quantities of materials, and a sensor chip with immobilized binding agent can typically be used for more than 100 analysis cycles. The chip surface can be regenerated with mild acidic or basic solutions. Several gentle cocktail solutions are available for regeneration (Andersson, 1999).

Accordingly, the invention is directed to binding agents that can be used in assays for a selected target. Binding agents can be used in any type of immunoassay where antibodies are commonly employed.

Kits

The present invention is directed to kits for generating binding agents, which are applicable for practicing the methods of the present invention. The kit comprises a nucleic acid that encodes a parental or a generic binding agent, for example, a nucleic acid encoding a SEQ ID NO:2, SEQ ID NO:4 or SEQ ID NO:37 binding agent, or variants and derivatives thereof. Examples of such nucleic acids include nucleic acids comprising SEQ ID NO:1 or SEQ ID NO:3. In another embodiment, the kit can include an expression vector that can encode SEQ ID NO:2, SEQ ID NO:4 or SEQ ID NO:37 binding agents, or variants and derivatives thereof. In other embodiments, the kit can include a library of vectors or oligonucleotides (e.g., at least one of the SEQ ID NO:25-29 oligonucleotides) that have random loop sequences. The kit can further comprise a set of instructions for generating a library of binding agents using the nucleic acids, oligonucleotides or vectors provided.

In another embodiment, a kit of the invention may contain a machine-accessible medium having associated content capable of directing the machine to perform a method. Such a machine-accessible medium can be a diskette, compact disc or other medium that provides a computer program of the invention. The program provided can include one of the methods described above, for example, the MKBIND program or one of the methods illustrated in FIG. 8 or 10 that are further described above. Such a kit can further include a container with a nucleic acid or an expression vector that encodes a parental or a generic binding agent, for example, a nucleic acid or vector encoding SEQ ID NO:2, SEQ ID NO:4 or SEQ ID NO:37, or variants and derivatives thereof. The kit can include useful oligonucleotides (e.g. one or more of the SEQ ID NO:25-29 oligonucleotides) that have random loop sequences. The kit can further include instructions for running the computer program or generating a library.

The invention will be described in more detail with reference to the following Examples. However, it should be understood that the invention is not limited to the specific details set forth in the Examples.

EXAMPLE 1

Binding Agent Construction

Molecular Modeling:

The molecular modeling studies performed utilized two visualization programs, Swiss PDB Viewer (Guex and Peitsch, 1997) and Rasmol (Sayle and Milner-White, 1995). Model work was performed on a PC running Windows 2000, as well as a Silicon Graphics, Inc. Octane UNIX workstation. Additionally, the Cerius2 molecular modeling package from Molecular Simulations, Inc. was utilized on the Octane. Three dimensional structure files were downloaded from the Protein Databank as follows: 1bzq.ent, 1f2x.ent, 1g6v.ent, i3v.ent, 1jto.ent, 1jtt.ent, 1jtp.ent, 1kxq.ent, 1amk.ent, 1am1.ent, 1b9b.ent, and 1hti.ent.

These files were used to analyze the three-dimensional structure of the proteins, and the chemical nature and identification of conserved and variant amino acids in the target contact regions and the amino acids involved in secondary structure maintenance. This information was utilized to design a parental consensus binding agent that could be easily manipulated using genetic engineering techniques and that would (at the DNA level) serve as the basis of the combinatorial library.

The first step was to begin with a full-length amino acid sequence that was designed from of the known camelid sequences. A robust pairwise alignment of these amino acid sequences was calculated using the program CLUSTAL (Higgins et al., 1992). A consensus sequence was then constructed based on this alignment. In addition information from the triose isomerase beta barrel structure was incorporated into the alignment in order to add stability features into the design.

The beta barrel motif is one of the most stable super secondary structural features known in protein structure. It is stabilized by a series of regular inter-strand hydrogen bonds and internal barrel packing interactions. A beta barrel is therefore an ideal starting point for the construction of small monomeric binding agents.

The third step entailed building a homology model of the new polypeptide. The final amino acid sequence of the parental binding agent was threaded onto the alpha carbon trace of 1jtt.ent using the programs ProMod and SwissModel (Peitsch, 1996; Peitsch et al., 1996). This model was then subjected to energy minimization using a GROMOS 96 forcefield, and several rounds of molecular mechanics geometry optimization using the SYBYL® forcefield (Clark et al., 1989). The final minimized/optimized model was then analyzed for bad side chain interactions and torsional geometry. Corrections to the structural model were made as appropriate. Further energy minimization experiments were conducted on a Beowulf cluster computer from Rocketcalc, LLC.

The amino acid sequence of a generic binding agent is provided in FIG. 5 with the five loop regions (i to v) indicated, and is also recited below (SEQ ID NO:4).

```
  1 MDVQLQASGG GSVQAGGSLR LSCAASAGAA GAACAGWFRQ

41 APGKEREGVA AINAGAAGTS YADSVKGRFT ISQLAGAANV

81 YLLMNSLEPE DTAIYYCAAG HAGAAGAATC GHGLSTAGAA

121 GAPWGQGTQV TVSS
```

The loop portions of the parental binding agent (SEQ ID NO:4) have alanine and glycine residues. In this way a generic binding agent could be purified and stability studied prior to building the combinatorial library.

Nucleic Acid Design, Construction, and Cloning:

To generate a nucleic acid that encodes the parental binding agent the SEQ ID NO:4 amino acid sequence was back translated using the standard genetic code. Codon choice was based on *E. coli* codon bias, meaning that final codon selected for a particular amino acid was the most frequently used codon for that amino acid in *E. coli*. Flanking sequences were added in order to facilitate cloning that brought the entire sequence to 423 bp. The full-length structural gene for the parental binding agent was 405 bp (SEQ ID NO:3). This SEQ ID NO:3 sequence is shown in FIG. 4 and is provided below.

```
  1 ACACAC<u>CATA</u> TGGACGTTCA GCTGCAGGCT TCTGGTGGTG

41 GTTCTGTTCA GGCTGGTGGT TCTCTGCGTC TCTCTTGCGC

81 TGCTAGCGCT GGTGCTGCTG GTGCTGCTTG CGCAGGTTGG

121 TTCCGTCAGG CTCCGGGTAA AGAACGTGAA GGTGTTGCTG

161 CTATTAATGC TGGTGCTGCT GGTACTAGTT ACGCTGACTC

201 TGTTAAAGGT CGTTTCACCA TCTCTCAATT GGCTGGTGCT

241 GCTAACGTTT ACCTGCTGAT GAACTCTCTG GAACCGGAAG

281 ACACCGCTAT CTACTACTGC GCTGCTGGCC ACGCTGGTGC

321 TGCTGGTGCT GCCACGTGCG GTCACGGTCT GAGTACTGCT

361 GGTGCTGCTG GTGCTCCATG GGGTCAGGGT ACCCAGGTTA

401 CCGTTTCTTC TTA<u>GATATC</u>A CAC
```

The underlined sequences in SEQ ID NO:3 above denote the 5' Nde I site and the 3' Eco RV sequence that have been incorporated into the DNA sequence in order to facilitate cloning. The initiation and termination codons are in bold. The loop portions of the SEQ ID NO:3 binding agent nucleic acid have been replaced by codons coding for alanine and glycine. In this way the progenitor binding agent could be purified and stability studied prior to building the combinatorial library.

In order to build a nucleic acid having the SEQ ID NO:3 sequence, 18 single stranded oligonucleotides that span the entire SEQ ID NO:4 coding region were synthesized. The oligonucleotides were usually 50 nucleotides in length. Each oligonucleotide was complementary to another oligonucleotide, such that when hybridized with the binding partner, the resulting fragment contained a central duplex region of thirty base pairs and was flanked on each end by a ten nucleotide single-strand region. Oligonucleotide sequences are shown in Table 4. Shorter oligonucleotides were employed for the ends (oligonucleotides 1 and 18 in Table 4).

TABLE 4

DNA oligonucleotides used for the generic binding agent.

| Oligo No | Sequence | SEQ ID NO: |
|---|---|---|
| 1 | ACACACCATATGGACGTTCAGCTGC AGGCTTCTGGTGGTG | 5 |
| 2 | TGAACAGAACCACCACCAGAAGCC TGCAGCTGAACGTCCATATGGTGTGT | 6 |
| 3 | GTTCTGTTCAGGCTGGTGGTTCTCTG CGTCTGTCTTGCGCTGCTAGCGCT | 7 |
| 4 | CAGCAGCACCAGCGCTAGCAGCGCA AGACAGACGCAGAGAACCACCAGCC | 8 |
| 5 | GGTGGTGCTGCTGGTGCTTGCGCAGG TTGGTTCCGTCAGGCTCCGGGTAA | 9 |
| 6 | TTCACGTTCTTTACCCGGAGCCTGAC GGAACCAACCTGCGCAAGCAGCAC | 10 |
| 7 | AGAACGTGAAGGTGTTGCTGCTATTA ATGCTGGTGCTGCTGGTACTAGTT | 11 |
| 8 | GAGTCAGCGTAACTAGTACCAGCAGC ACCAGGATITAATAGCAGCAACACC | 12 |
| 9 | ACGCTGACTCTGTTAAAGGTCGTTTC ACCATCTCTCAATTGGCTGGTGCT | 13 |
| 10 | AAACGTAAGAAGCACCAGCCAATTGA GAGATGGTGAAACGACCITTAACA | 14 |
| 11 | GCTAACGTTTACCTGCTGATGAACTC TCTGGAACCGGAAGACACCGCTAT | 15 |
| 12 | GCAGTAGTAGATAGCGGTGTCTTCC GGTTCCAGAGAGTTGATCAGCAGGT | 16 |
| 13 | CTACTACTGCGCTGCTGGCCACGCT GGTGCTGCTGGTGCTGCCACGTGCG | 17 |
| 14 | AGACCGTTACCGGACGTGGCAGCAC CAGCAGCACCAGCGTGGCCAGCAGC | 18 |
| 15 | GTCACGGTCTGAGTACTGGCTGGTGC TGCTGGTGGTCATG | 19 |
| 16 | ACCCTGACCGCATGAGCACCAGCAGC ACCAGCCAGTACTC | 20 |
| 17 | GGGTCAGGGTAGCCAGGTTACCGTT TCTTCTTAGATATCACAC | 21 |
| 18 | GTGYGATATCTAAGAAGAAACGGTA ACCTGGGT | 22 |
| 19 | ACACACCATATGGACGTTCAGC | 23 |
| 20 | GTGTGATATCTAAGAAACGGT | 24 |

The construction of the gene encompassed three separate steps.

First, 5 µg of each oligonucleotide and its complementary binding partner were mixed together in 10 mM Tris-HCl (pH 7.2), 10 mM NaCl in a final volume of 10 µL. Nine separate hybridization reactions were therefore set up using the following combinations of oligonucleotides:

Oligonucleotides 1 and 2 (SEQ ID NO:5 and 6);
Oligonucleotides 3 and 4 (SEQ ID NO:7 and 8);
Oligonucleotides 5 and 6 (SEQ ID NO:9 and 10);
Oligonucleotides 7 and 8 (SEQ ID NO:11 and 12);
Oligonucleotides 9 and 10 (SEQ ID NO:13 and 14);
Oligonucleotides 11 and 12 (SEQ ID NO:15 and 16);
Oligonucleotides 13 and 14 (SEQ ID NO:17 and 18)
Oligonucleotides 15 and 16 (SEQ ID NO:19 and 20); and
Oligonucleotides 17 and 18 (SEQ ID NO:21 and 22).

The mixtures were each heated in a water bath at 95° C. for 10 minutes. The heat was turned off, and the entire water bath was allowed to cool to room temperature over a period of five hours.

Second, aliquots (10 µL) from each of nine different "slow cool" hybridization reactions were mixed together (final volume 50 µL). The tube was heated at 45° C. for 10 minutes and then was placed into an ice bath. T4 DNA ligase and buffer (New England Biolabs) were added to the tube, and the reaction (final volume 60 µL) was incubated at 16° C. for 20 hours.

Third, the full length structural gene was selected from the mixture of fragments using two PCR primers (Table 3, oligonucleotides 19 and 20 (SEQ ID NO:23 and 24)) that were complimentary to the extreme 5' and 3' ends of the structural gene. This ensured that only full-length gene product would be amplified. In addition the 3' amplification primer contained a Eco RV site in order to facilitate cloning. The 5' amplification primer contained a Nde I site. The PCR reaction was performed using 1 µL of the ligation mixture as follows: 95° C., 1 minute; 49° C., 1 minute; 72° C., 30 seconds. Thirty cycles of this program were performed in a Techne Progene PCR device. A ten minute 72° C. extension incubation was performed after the last PCR cycle. The PCR reaction product was verified by DNA agarose gel electrophoresis.

The PCR reaction product was then purified via a Promega DNA Wizard PCR clean-up kit and was prepared for cloning. First, the DNA fragment was treated with T4 DNA polymerase in the presence of ATP in order to ensure fully duplex ends. This reaction was performed according to the instructions from New England Biolabs, Inc. The DNA was re-purified using the Promega DNA Wizard PCR clean-up kit. Second, the DNA was digested with Nde I and Eco RV and was purified by ethanol precipitation. The final DNA was resuspended in a small volume of 10 mM Tris-HCl (pH 8.0), 1 mM EDTA.

The cloning vector, a modified form of pET29a (Invitrogen) in which the Fsp I, Ase I, and Acl I vector sites were removed, was digested with Nde I and Sma I, and was purified using the Promega DNA clean-up kit. This digest produced a linear vector that was compatible with the DNA fragment insert. This combination ensured directional, in-frame cloning of the fragment. The vector and the insert were mixed in approximately 1:10 molar ratio and were ligated together in the presence of T4 DNA ligase at 16° C. for 20 hours (total reaction volume was 20 µL). Competent JM109 bacteria were transformed with 5 µL of the ligation reaction. After growth on LB/60 µg/mL ampicillin agar plates, single colonies were selected, and plasmid was purified from the colonies by the miniprep procedure using a Promega miniprep DNA isolation kit. Isolated plasmids were evaluated by DNA agarose gel electrophoresis, restriction endonuclease digestion, and finally by DNA sequencing. The plasmid construct was designated pBART2. This construct encoded the base, or parental, binding agent (SEQ ID NO:3).

Randomized oligonucleotides that correspond to the loop regions were synthesized using standard solid phase chemistry. The sequence of these oligonucleotides is shown in Table 5.

TABLE 5

Sequence of degenerate loop oligonucleotides that were used to produce random libraries of binding agents.

| Loop No. | Sequence | Restriction Sites | SEQ ID NO: |
|---|---|---|---|
| i | GCTAGCnnnn nnnnnnnnnn nnnnnnnTGC GCA | Nhe I Fsp I | 25 |
| ii | ATTAATnnnn nnnnnnnnnn NACTACT | Ase I Spe I | 26 |
| iii | CAATTGnnnn nnnnnnnAA CGTT | Mfe I Acl I | 27 |
| iv | TGGCCAnnnn nnnnnnnnnn nnnnnnnCAC GTG | Msc I Pml I | 28 |
| v | AGTACTnnnn nnnnnnnnnn nnnnCCATGG | Sca I Nco I | 29 |

The loop regions (i to v) correspond to the loop regions of the present binding regions. Table 5 provides the sequence of oligonucleotides used for generating combinatorial libraries of binding agents, as well as the incorporated unique restriction sites that flank the random nucleotides (n) and facilitate cloning. The position and number of random nucleotides (n) are indicated. Hence, loop i has 21 random nucleotides, loop ii has 15 random nucleotides, loop iii has 12 random nucleotides, loop iv has 21 random nucleotides, and loop v has 18 random nucleotides. For example the oligonucleotide for loop i is a 33 nucleotide sequence with 21 central random bases with a Nhe I site at the 5' end and a Fsp I site at the 3' end.

To prepare oligonucleotides for insertion into the vector encoding the parental binding agent, each of the SEQ ID NO:25-29 oligonucleotides with their complimentary binding partners were separately heated in a water bath at 95° C. for 10 minutes. The heat was turned off, and the entire water bath was allowed to cool to room temperature over a period of three hours.

To generate the random combinatorial library, the pBART2 vector was first digested with Nhe I and Fsp I. This linear plasmid was isolated by chromatography on Sephadex G-25 that was run in 10 mM Tris-HCl (pH 7.8). Fractions containing linear plasmid were pooled and were concentrated via Centricon (Amicon, Inc.). The loop i oligonucleotides were similarly digested and were purified via native PAGE. Digested oligonucleotides and plasmid were mixed in a 10:1 molar ratio and were ligated overnight at 16° C. in the presence of T4 DNA ligase. The ligation reaction was diluted (to lower the T4 DNA ligase buffer glycerol concentration) with 10 mM Tris-HCl (pH 7.8). The random oligonucleotides that correspond to loop regions ii to v were inserted into pBART2 sequentially following the same procedure. The final ligation product was used to transform JM109 cells.

Library Screening:

The combinatorial library generated was amenable to robotic screening. To prepare for a trial screening reaction, individual colonies were pooled into groups of 10 and aliquoted into 387 well plates that contained LB that was supplemented with ampicillin (60 µg/mL). Cells were incubated at 37° C. for 10 hours followed by the induction of polypeptide expression for 3 hours. Cells were lysed by the addition of BPER extraction agent, followed by neutralization of the supernatant. A 5 µL aliquot from each well was transferred to a fresh plate. The protein content of the aliquot was adsorbed to the sides of the well by evaporating the well solution with a warm stream of air.

As an initial test, the protein trypsin was used as the target to which the binding agent would bind. Oregon Green (Molecular Probes, Inc.) labeled bovine trypsin in Phosphate buffered saline (PBS) was added to the wells and the plates were incubated at 37° C. for 1 hour. The wells were washed three times with PBS. Fluorescence was quantitated using a Dynex-MFX fluorescent microtiter plate reader. The excitation and emission wavelengths were 485 and 500 nm respectively. A total of 38,700 clones were screened in the initial run.

The pooled clones that corresponded to positive wells in the first screen were re-screened separately in order to identify the positive colony in a pure form. Screening was as described above. DNA from positive clones was sequenced. Polypeptide from positive clones was expressed and purified as described above.

Figure 1B:
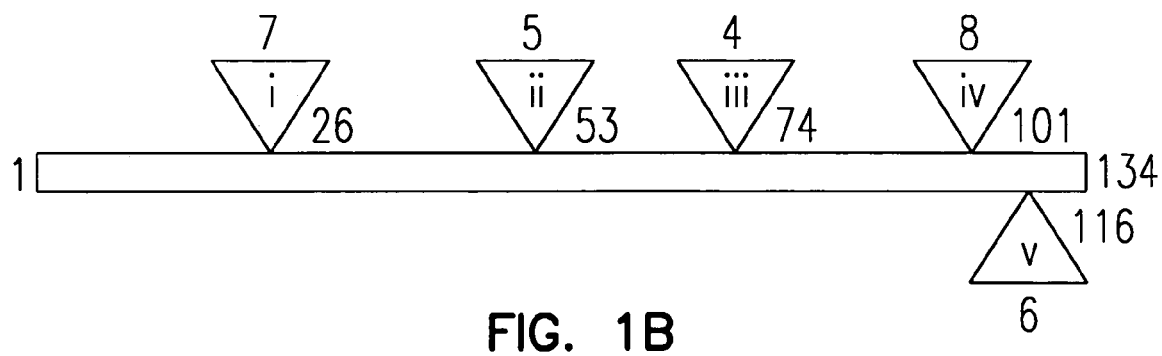
FIG. 1B is a schematic diagram of a binding agent polypeptide of the invention. The location of the five loop regions (i to v) within the binding agent is shown relative to their amino acid position. Numbers above the loops show the number of amino acids in the loop.

Results:

Schematic diagrams of the parental binding agent DNA clone and protein are shown in FIG. 1. The DNA sequence of the generalized parental binding agent is shown in FIG. 2 and the generalized amino acid sequence is shown in FIG. 3. The term generalized means that the loop regions are undefined and can be altered to have any sequence, as denoted by the "n" nucleotides in SEQ ID NO:3 and the "Xaa" amino acids in SEQ ID NO:4.

For the actual construction of the parental binding agent, alternating codons for alanine and glycine were inserted into the areas denoted by the n's. This addition is shown in FIG. 4 for the DNA sequence and in FIG. 5 for the amino acid sequence. The choice of Ala-Gly (GCTGGT) repeats was arbitrary and merely served as a place-holder. Use of Ala-Gly (GCTGGT) repeats also allowed for a trial expression, purification, and testing of a parental binding agent. One of the benefits of the parental binding agent and nucleic acids encoding the parental binding agent, is that the structure determining amino acids (the non-loop areas) have been identified and can be continuously optimized.

The back translation of the parental binding agent amino acid sequence was performed to produce a DNA clone that could be used for the construction of the combinatorial library. Codon biasing towards E. coli was done to ensure maximum protein production. Unique restriction sites were incorporated into the DNA sequence that flanked all five-loop regions. This greatly facilitated the formation of the combinatorial library. Flanking restriction sites were also incorporated into the parental binding agent DNA sequence in order to facilitate cloning into protein expression vectors. Although this system was optimized for bacterial production, one can produce the binding agent polypeptides in any expression system simply by subcloning the structural gene into another vector.

Constriction of the 423 nucleotide SEQ ID NO:3 sequence required a series of short oligonucleotides, because it is beyond current synthetic methodology to construct DNA sequences over 100 bases in length. In addition, it can be difficult to efficiently hybridize longer DNA molecules. Hence construction was carried out using a series of hybridization steps. The individual oligonucleotides, when mixed together in equimolar amounts, were efficiently converted into duplex molecules by a "slow cool" hybridization step.

Slowly reducing the temperature from 95° C. over a period of hours favored the formation of short duplexes. The resulting fragments contained a central double stranded region of 30 base pairs, and were flanked by 10 nucleotide single-stranded termini (except for the extreme terminal oligonucleotides, which were shorter). These "sticky ends" were used to drive the assembly of the full-length SEQ ID NO: 3 sequence, again by hybridization.

Formation of the final SEQ ID NO:3 sequence at this stage was performed by heating an equimolar mixture of the duplex molecules to 45° C. for 10 minutes. This step disrupted any partially formed duplex structures formed by association of the termini, but did not disrupt the fully formed central duplex regions. The heated material was "quick cooled" by placing the reaction tube on ice. This hybridization step favored the hybridization of short regions of DNA (i.e.—the 10 base sticky ends). The phosphodiester backbone of the 423 bp DNA fragment was then formed by the enzyme T4 DNA ligase.

The full-length gene sequence was selected from the resulting mixture of fragments using PCR amplification. This step was far more efficient than purifying the fragment from agarose gels. This step also resulted in a large amount of material for subsequent cloning steps. The ends of the gene were prepared for cloning by blunt ending with T4 DNA polymerase and digestion with Nde I and Eco RV. This resulted in a DNA molecule that could be efficiently and directionally cloned into protein expression vectors. The validity of the final insert was confirmed by DNA sequencing after performing mini-preps of plasmid DNA from several transformed bacterial colonies (data not shown).

Moreover, the cloning procedures employed permitted the loop domains to be easily replaced by combinatorial sets of randomized loop sequences. The oligonucleotides used to produce the loop variants are shown in Table 4 (only the coding strand is shown).

While the method presented here was quite straightforward, it was only one of many different molecular biology routes that could have been used to construct the library. Hence, although the library was cloned into pET29a, it would be straightforward to sub-clone the entire library (by traditional restriction endonuclease digestion or via PCR) into a more suitable biopaning system, for example, a phage system where the binding agent would be displayed on the phage cost. The entire library can be recreated by amplifying the inserts as a whole and cloning them back into another vector of choice.

Construction of the combinatorial library resulted in a library of approximately $6 \times 10^{12}$ independent clones. This initial bacterial library had sufficient diversity to effectively screen for binding agents that can bind a target molecule.

Screening of the library was greatly facilitated by the use of a robotic system. Future libraries will most likely be in a screening system that is even more amenable to faster throughput. Even so, over 38,000 clones were screened more or less automatically in four days. From this first trial screen one positive clone was identified. This clone can bind to bovine trypsin (see below). So the feasibility of using the constructed library to screen for novel loop variants that can bind novel targets is proven. The isolated clone had a loop i DNA sequence of CGTTACCTGCGTTACCCGTCT (SEQ ID NO:30), which corresponds to an amino acid sequence of RYLRYPS (SEQ ID NO:31). In contrast, the parental binding agent the amino acid sequence was AGAAGAA (SEQ ID NO:32).

EXAMPLE 2

Biochemical and Biophysical Studies of Binding Agents

This Example illustrates some of the chemical, biochemical and physical properties of binding agents produced by the methods of the invention.

Purification of the Binding Agent:

The expression strategy utilized a typical T7 RNA polymerase over-expression system. The vector construct added a C-terminal hexa-histidine tag to the binding agent polypeptide in order to facilitate purification. BL21(DE3) cells containing the expression plasmid constructs were grown at 37° C. in Luria broth supplemented with 1% glucose and 60 µg/mL ampicillin from a 1% inoculum. IPTG was added to a final concentration of 0.5 mM when the cells had reached an $A_{595}$ value of 0.8 (in approximately three hours post inoculation). Cell growth continued for five additional hours before harvesting. Typically, 5 g of cells was obtained per liter.

Cells were pelleted by centrifugation at 10,000×g for ten minutes and re-suspended in one volume of 10 mM Tris-HCl, pH 8.0. The cells were respun as above and were frozen for at least 2 hours at −70° C. The frozen pellet was re-suspended in two volumes of BPER E. coli protein extraction buffer (Pierce Scientific). The mixture was incubated at 30° C. for 20 minutes with occasional mixing. The resulting extract was clarified by centrifugation at 12,000×g for 20 minutes, and the supernatant was dialyzed against 2 L of His-Tag loading buffer (all His-Tag buffers and resins are from Novagen, Inc.). The dialyzed material was diluted to a final concentration of 2.5 mg/mL with loading buffer, and was applied to a 5 cm×3.97 cc² His-Tag resin column that had been previously charged with nickel. All chromatography steps were performed at room temperature. The column was washed with five column volumes of His-Tag wash buffer. Protein was eluted from the column with a 100 mM to 500 mM imidazole-HCl gradient. Fractions were collected throughout the gradient, and those fractions containing protein (as assayed by SDS PAGE) were pooled and concentrated to 5 mg/mL via Centricon (Amicon, Inc.). This material was dialyzed extensively versus 10 mM Tris-HCl (pH 8.), 1 mM EDTA, 50 mM NaCl and constituted Fraction I.

Homogeneous binding agent was prepared from Fraction I via hydrophobic interaction chromatography (HIC). Ammonium sulfate (from a 4 M stock solution) was added to the Fraction I pool to a final concentration of 1.5 M. This material was applied to a BioRad Econo-Pac t-Butyl HIC cartridge column (one mL total column volume). A 100 mL reverse concave gradient from 1.5 M $(NH_4)_2SO_4$/3.0 M KCl/Buffer I to Buffer I alone was applied directly after loading the sample. Homogeneous polypeptide eluted from the column during the last third of the gradient. The central 95% of the peak (as measured by absorbance) was pooled. The material was concentrated to a final volume of 2 mL by pressure filtration through a semipermeable membrane (Amicon YM-3) and dialyzed versus 2 L of 10 mM Tris-HCl (pH 7.5), 1 mM EDTA, 25 mM NaCl. The concentrated/dialyzed material was used for all subsequent analyses.

Chemical Denaturation:

Stability measurements of the parental binding agent were performed by measuring protein unfolding in the presence of urea via intrinsic tryptophan fluorescence (Lakowicz, 1983) in a Shimadzu RF5301 fluorometer. The excitation and emission wavelengths were 295 nm and 340 nm respectively. Both excitation and emission monochrometer slits were set at 1.5 nm. Binding agent (20 μM) was mixed with increasing amounts of guanidinium hydrochloride (GdnHCl, in the concentration range of zero to 6.0 M), and the samples were incubated at room temperature for ten hours to ensure that unfolding equilibrium had been achieved. Relative fluorescence was converted into free energy values according to the relation (Pace et al., 1989):

$$\Delta G = -RT\ln\left[\left(\frac{y_f - y_i}{y_i - y_u}\right)\right]$$

where $y_f$ and $y_u$ are the relative fluorescence values for fully folded and fully unfolded parental binding agent respectively, $y_i$ is the relative fluorescence of the unfolding intermediates, T is the absolute temperature, and R is the gas constant. Linear regression and extrapolation of the relationship $\Delta G$ versus [GdnHCl] was employed to determine the free energy value in the absence of denaturant ($\Delta G_{H2O}$). Similarly, the fraction unfolded polypeptide ($F_u$) was calculated from the fluorescence data according to the relation (Pace et al., 1989):

$$F_U = \left(\frac{y_f - y_i}{y_f - y_u}\right)$$

Isothermal Titration Calorimetry.

Isothermal titration calorimetry (ITC) was performed with a VP-ITC instrument from MicroCal, Inc. Titrations were carried out by injecting 5 □L of a binding agent (at concentration ranges from 0.5 mM to 1.0 mM) into the 1.4 mL stirred reaction cell. Bovine trypsin (Sigma Chemical Co.) ranged in concentration from 10 to 30 μM in the cell. Both the inhibitor and the enzyme were in 20 mM sodium cacodylate (pH 6.9), 40 mM NaCl. Titrations were conducted at 20° C. Typical experimental conditions for the titrations were a 10 second injection period followed by a 240 second delay between injections for a total of 40 injections. Blank titrations of binding agent into buffer were performed in order to correct for heats of dilution and mixing.

The independent set of multiple binding sites is the most common model for binding experiment evaluations. The analytical solution for the total heat is determined by (Freire et al., 1990):

$$Q = V\Delta H\left[[L] + \frac{1 + [M] + nK - \sqrt{(1 + [M]nK - [L]K)^2 + 4K[L]}}{2K}\right]$$

where Q is the total heat, V is the cell volume, $\Delta H$ is the enthalpy, M is the macromolecule concentration (the binding partner in the cell), n is the binding stoichiometry, L is the ligand concentration (the binding partner in the syringe), and K is the association constant. Data were fit to this model using Origin version 5 (MicroCal, Inc.).

The purification regime took approximately two days to complete. Purification of parental binding polypeptide from E. coli resulted in approximately 15 mg of polypeptide per liter of induced culture. The polypeptide was overproduced approximately 36-fold in E. coli. Purification scheme was aided by the fact that the polypeptide was isolated from bacteria as a C-terminal His-Tag fusion. Hence, it was straightforward to express and then purify the polypeptide. Preparation of the crude bacterial extract was efficiently achieved by chemical lysis of the bacteria followed by clearing the lysate via centrifugation. It was also possible to disrupt the bacteria after expression via sonication or via a French press. The polypeptide was therefore purified to homogeneity in two steps. Throughout the course of the purification trial, the parental binding agent was visualized solely by SDS PAGE analysis.

The parental binding agent polypeptide unfolds in a highly cooperative manner. Equilibrium unfolding monitored by intrinsic tryptophan fluorescence displays an overall 70 percent decrease in emission fluorescence intensity and a 12 nm shift in the emission peak maximum to longer wavelengths (data not shown). Fluorescence intensity emission spectra were converted into the fraction of unfolded polypeptide as described above.

Figure 7:
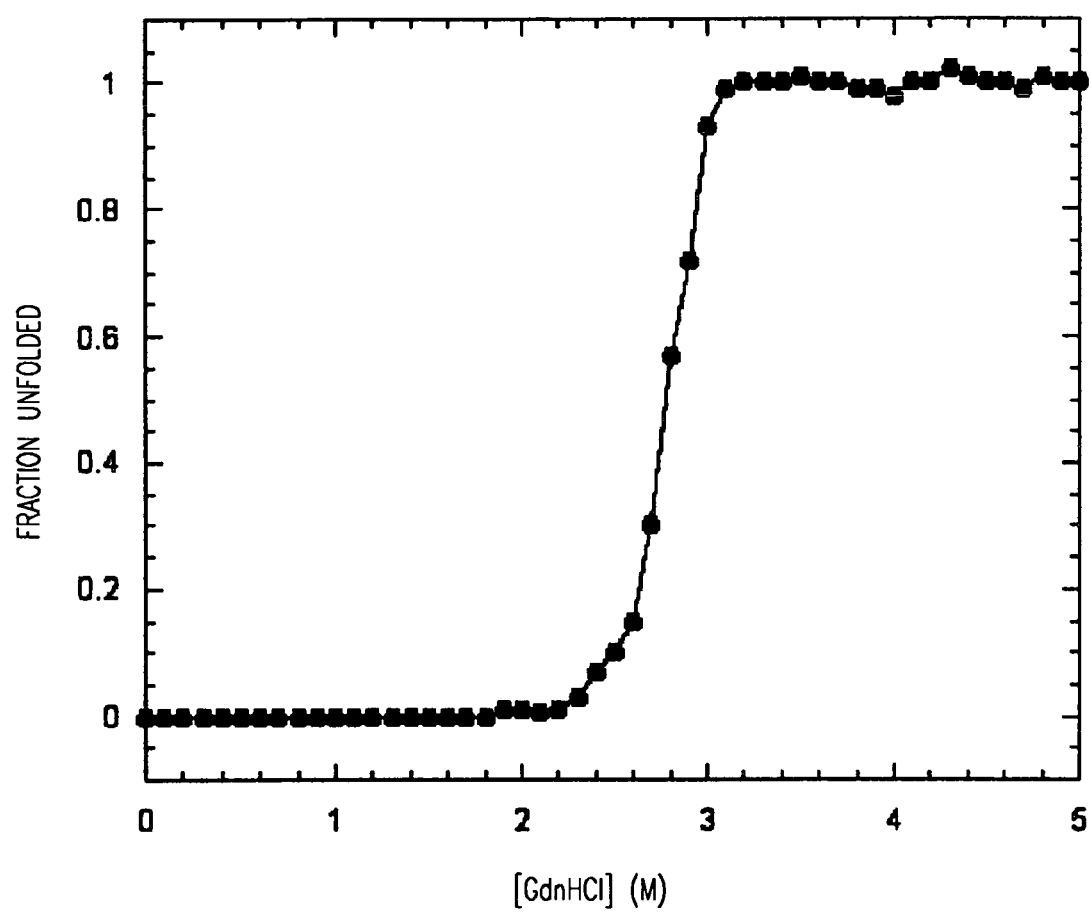
FIG. 7 is a graph illustrating the chemical denaturation of the parental binding reagent. The fraction of unfolded protein is plotted as a function of the denaturant concentration. The unfolding reaction shows a transition midpoint at 2.7 M Gdn-HCl, which corresponds to a free energy $\Delta G$ of 42.7 kJ mol$^{-1}$, (m=16.8 kJ M$^{-1}$ mol$^{-1}$).

FIG. 7 shows that the midpoint in the unfolding curve for the parental binding agent occurred at a concentration of 2.7 M GdnHCl. The unfolding transition began at 2.4 M GdnHCl and was completed at a denaturant concentration of 3.1 M GdnHCl. The existence of a single peak in the first derivative plot of this data (not shown) supports the hypothesis that the polypeptide denatures as a highly cooperative two state process. Conversion of the unfolding curve into a free energy versus the concentration of GdnHCl plot with extrapolation via a linear regression to the free energy in the absence of urea indicated that the polypeptide has a native free energy of 42.7 kJ mol$^{-1}$.

The chromatographic behavior the parental binding agent on the BioSelect 125 gel exclusion column was consistent with the expected monomeric polypeptide. The analytical gel filtration experiment (data not shown) indicated that the polypeptide eluted from the column slightly earlier than a myoglobin standard (12 kDa). The elution profile was consistent with the polypeptide being a monomer with a molecular weight of approximately 13.8 kDa (this includes the His-Tag).

The calculated Stokes radius was 26 Å. This value was in good agreement with the dimensions of the atomic model. The elution profile also indicated that the polypeptide was roughly symmetric in nature, because the frictional coefficient was 1.27. This frictional coefficient did however indicate that the polypeptide has a slight degree of oblate spheroid character, which may indicate that the loop region plays a part in determining the hydrodynamic properties of the polypeptide.

EXAMPLE 3

Computer Generated Binding Agent Sequences

This Example illustrates how binding agents that can bind specific target molecules can be generated using a computer program provided by the invention.

Computer Modeling of the Binding Agent(s)

The parental binding agent polypeptide was 134 amino acids in length and had a total molecular weight of 12.8 kDa. FIG. 6 illustrates the three dimensional structure of the generic binding agent. The overall topology of the binding agents is that of a beta sandwich (depicted by arrows) stabilized by a central disulfide bond (not shown). The binding agents of the invention also have five loops (shown as thin strands that connect the arrows), which are the primary target recognition elements. The polypeptide sequence ends with a tail that can be used to anchor the molecule on the surface of a bead or other surface for use in diagnostic devices. The target contact region is defined by the spatial orientation of these loops.

A three dimensional model of the polypeptide was prepared by threading the amino acid sequence (SEQ ID NO:38) onto the three dimensional alpha carbon backbone of a camelid antibody (structure 1jtt.ent in the Protein Databank) using the program SwissModel. The optimal thread result was converted into a three dimensional structure that included amino acid side chain positions using the program ProMod. This initial model was subjected to a round of simulated annealing in order to minimize negative side chain interactions. Several rounds of a SYBYL® level geometry optimization put all dihedral angles and torsions into proper geometry. A final round of energy minimization using a GROMOS96 parameter set, without a reaction field, was employed. These results are shown in Table 6. The final model has an overall energy of −3581 kJ/mol and is shown in FIG. 6. All amino acid residues are within allowable Ramachandran space (data not shown) and there are no negative steric interactions.

TABLE 6

GROMOS 96 energy minimization results for the homology model (only the major parameters from the forcefield are shown).

| Parameter | Energy (kJ/mol) |
|---|---|
| Bonds | 57 |
| Angles | 422 |
| Torsions | 690 |
| Impropers | 111 |
| Nonbonded | −3082 |
| Electrostatic | −1779 |
| Constraints | 0 |
| Total: | −3581 |

Computer Programming:

A program, MKBIND, was written in FORTRAN 77 that could be used to automatically identify loop amino acid sequences that bound to specific target molecules. The code was compiled to run under LINUX on a Rocketcalc, LLC Beowulf computing cluster. Parallelization of the code resulted in a significant speed-up in search time.

A flowchart for the general program flow of MKBIND is shown in FIG. 8. To begin, information relating to the three-dimensional structures of the parental binding agent and the target molecule was entered as two different data files the parental binding agent 1502 and the target 1512. This information included the atomic coordinates of all atoms in the generic binding agent (SEQ ID NO:38, see FIG. 12) and in the target molecule.

A specific search zone on the target (trypsin) was selected by picking an identifiable center of gravity (or an identifiable structural area such as a box or triangle or coordinates) that could be centered over a selected atomic coordinate within the target molecule. In some experiments, the depth of the identifiable center (box or triangle) projected about 3 Å from the average surface in the center to about the same distance below that level (to get the deeper grooves). The search area selected was about 20 Å×20 Å×6 Å.

The loop (i) length was defined to be seven amino acids. All twenty naturally occurring amino acids were defined as the class of amino acids to substitute into each position of loop (i). The program generated all the coordinate files for the loop (i) applied a simple coordinate transformation to anchor the new loops into the binding agent structure and generated a binding agent output file which comprises a series of files containing structural coordinates for all possible binding agents with all possible loop sequences.

The binding agent output file and the output target file were then communicated to the docking program 1510, 1518. The binding agent output file 1510 was a regular atomic coordinate file. The output target file 1518 was a file that defined the atomic coordinates of the amino acid residues in the target grid area, as well as the xyz coordinates of the grid itself. However, all three-dimensional structures are used by MKBIND as atomic coordinate files. The molecular docking program then docked each binding agent with the target using a flexible docking algorithm 1520. Hence, the loop-binding surface of the binding agent was centered by the MKBIND program within the volume of the coordinate grid of the target molecule. The program then moved the binding agent towards the target surface (still within the grid) along one axis in 0.1 A intervals, and a score was calculated (see below). The structure was then moved another 0.1 A. If the score improved the binding agent was moved further in until the score gets worse. At that point it was moved out by 0.1 A (to the last best score) and is then it was moved up in the same manner, then down, and then left and right. All such movement and resetting of position, resulted in the "optimal locale for the fit."

A docking score or fit score for each binding agent variant was then computed as described below.

$$\text{Fit score}=-[E_{elect}+E_{vdw}+E_{HB}]$$

where $E_{elect}$ is the electrostatic energy, $E_{vdw}$ is the Van der Waals term and $E_{HB}$ is the hydrogen bond energy. This empirical energy function is a summation of these three individual energy terms:

$$\sum \frac{q_i q_j}{4\pi\varepsilon_0 r} + \sum\left(\frac{Aij}{r_{ij}^{12}} - \frac{Bij}{r_{ij}^{6}}\right) + \sum\left(\left(\frac{A}{r_{AD}^{6}} - \frac{B}{r_{A}^{4}}\right)\right)\cos(\theta_{A-H-D})$$

If the fit was poor, the loop sequences and the binding agent variant coordinate file were discarded 1526. A top score 1524 was obtained and the loop sequences and the binding agent variant coordinate file were saved 1528.

Once the best fit was found the binder coordinate file was written out. The target and the optimized binding agent structural images were examined on the screen to inspect the fit. All high scoring loop sequences were output for offline analysis (e.g. alignment). MKBIND was therefore used to construct a novel binding agent that was capable of binding to bovine trypsin.

Results:

The computer program, MKBIND, successfully and automatically identified a parental binding agent loop variant that can bind to bovine trypsin. In order to shorten computation time for this first trial, only loop i variants were searched. The remaining loops were constrained to their initial Ala-Gly repeat sequences. Loop i was searched fully, that is all 20 amino acids were allowed to occupy each sequence. Thus $20^7$ ($1.28\times10^9$) sequences were searched.

The program took approximately 0.01 seconds to complete one novel search (i.e. make the random loop variant structure, dock it into the trypsin search grid, calculate the fit score, and output the coordinate and loop sequence files). Hence the entire run consumed $1.28\times10^7$ seconds (148 days to run).

Computational speed was enhanced by running the system on the Rocketcalc, LLC cluster. The linear speed up on the 20 processor system is 18.9. However, a cluster is not required to run the program. The search speed can be greatly accelerated by optimizing the docking parameters (i.e. doing less stringent searches and not making the grid spacing too fine). Because it is written in standard FORTRAN 77, the program can be run on any computer system.

The search resulted in the identification of the top scoring loop variant binding agent that can bind to bovine trypsin. The identified loop-i sequence was ITAVCHK (SEQ ID NO:35). An actual binding reagent protein was constructed (see Table 6) with this sequence inserted into the parental binding reagent loop i.

The loop i sequence obtained by computer was different from the loop i sequence obtained by molecular biology procedures. Sequences for the computer-generated and the biologically-generated loops are compared in Table 7.

TABLE 7

Results of loop i computer search and biological screen using trypsin as the target.

| Method | Amino Acid Sequence | DNA Sequence |
|---|---|---|
| Biological Screen | RYLRYPS SEQ ID NO:33 | GctagcCGTTACCTGCGT TACCCGTCTtgcgca SEQ ID NO:34 |
| Computer Search | ITAVCHK SEQ ID NO:35 | GctagcATCACCGCTGTT TGCCACAAAtgcgca SEQ ID NO:36 |

Loop i sequences incorporate flanking Nhe I and Fsp I restriction sites (lower case)

The binding agents having SEQ ID NO:33 and SEQ ID NO:35 were expressed and purified as described above. The biochemical and biophysical properties of these binding agents are provided in Table 8.

TABLE 8

Miscellaneous properties of the binding agents.

|  | Parental Binding Agent | Loop i variant Screening | Loop i Variant Computer |
|---|---|---|---|
| Length (aa) | 134 | 134 | 134 |
| Molecular wt (kDa) | 12.8 | 13.3 | 13.2 |
| pI | 6.3 | 7.8 | 7.2 |
| Charge at pH 7.0 | −0.87 | 1.1 | 0.26 |
| Hydrophobic aa (#) | 54 | 50 | 52 |
| Polar aa (#) | 37 | 40 | 39 |
| Extinction coefficient | 16980 | 19540 | 17100 |
| Cysteine (#) | 4 | 4 | 5 |
| Tryptophan (#) | 2 | 2 | 2 |

The ability of three binding agents (SEQ ID NO:4, SEQ ID NO:33 and 35) was tested to ascertain whether they could effectively bind bovine trypsin. Binding was measured by isothermal titration calorimetry (ITC).

Figure 9:
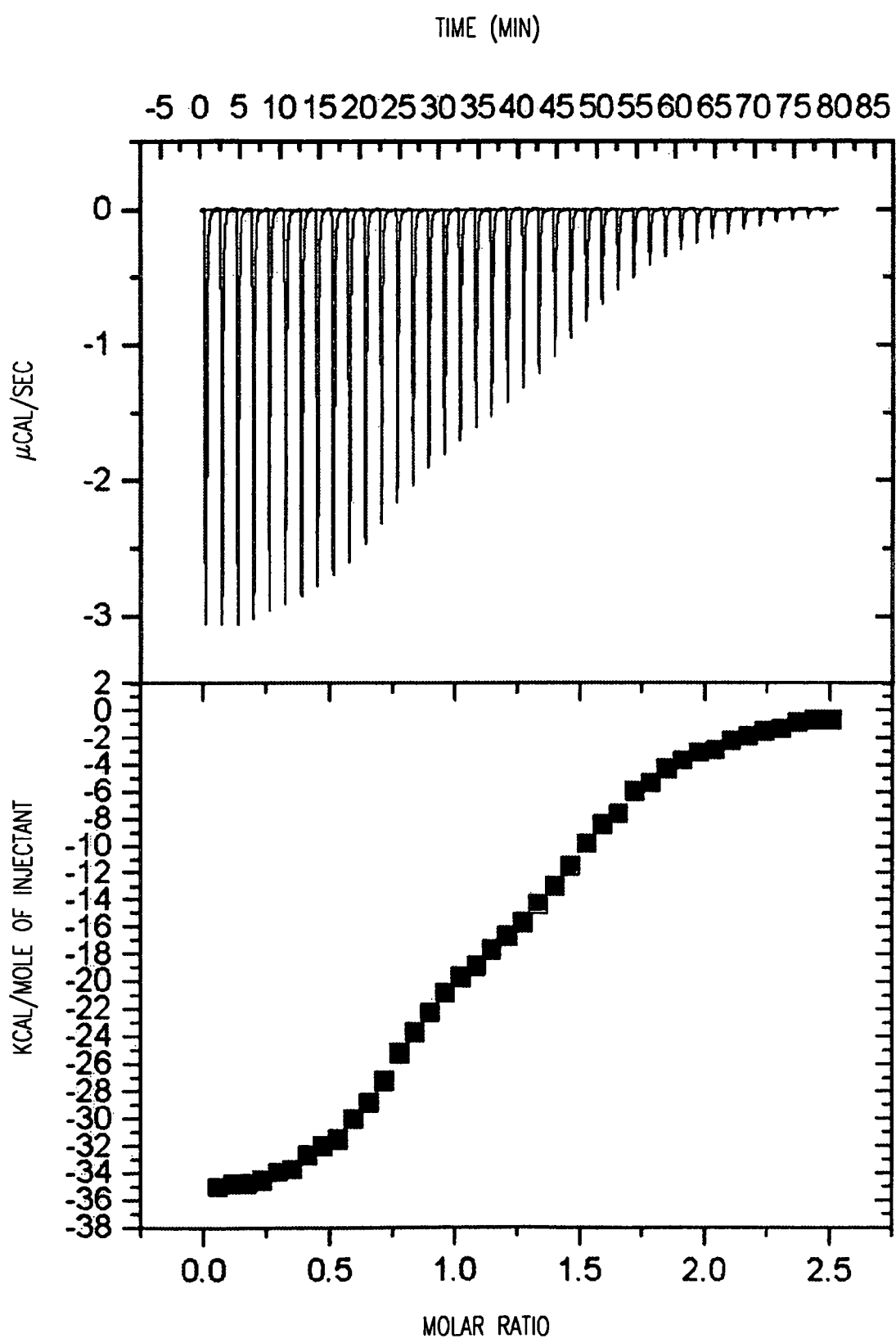
FIG. 9 is a graph illustrating the binding between the computer-generated loop i variant and bovine pancreatic trypsin as analyzed by ITC analysis. Binding reagents and trypsin were dialyzed into 20 mM sodium cacodylate (pH 6.9), 40 mM NaCl. The binding reagent was at a concentration of 1 mM and trypsin was used in the calorimeter cell at a concentration of 20 μM. The temperature was maintained at 20° C. 40 injections of 5 μL each were employed with a 240 second re-equilibrium time between injections.

The parental binding agent had no natural binding affinity for trypsin (data not shown). Under all experimental conditions, there is no detectable binding. However, as is shown in FIG. 9, the two loop variants had remarkable binding affinity for trypsin.

Table 9 provides a summary of some of the thermodynamic parameters observed for the various binding agents.

TABLE 9

Miscellaneous thermodynamic parameters of the binding agent-bovine trypsin interaction.

|  | Parental Binding Agent | Loop i variant Screening | Loop i Variant Computer |
|---|---|---|---|
| Stoichiometry: | nbd | 0.99 ± 0.04 | 1.02 ± 0.05 |
| $\Delta H$ (kcal/mol): |  | $-2.6 \times 10^6$ ±$1.45 \times 10^4$ | $-9.4 \times 10^5$ ±$1.10 \times 10^4$ |
| $\Delta S$ (cal mol$^{-1}$ K$^{-1}$) |  | −101.6 ± 2.2 | −96.6 ± 2.2 |
| $K_a$ (M$^{-1}$): |  | $1.65 \times 10^6$ ±$4.5 \times 10^4$ | $6.22 \times 10^5$ ±$1.9 \times 10^4$ |
| Temp (K) |  | 293 | 293 | nbd = no binding detected

These isothermal titration calorimetry results indicated that the interaction between trypsin and the SEQ ID NO:33 and 35 binding agents was enthalpically driven, that is $\Delta H$ was negative. The reaction was not favored entropically as evidenced by the negative value of $\Delta S$. However, the enthalpic term is larger in magnitude than the term, $T\Delta S$, hence the overall free energy ($\Delta G$) is negative. Even though only loop i was optimized in the computer screen, the procedures employed herein generated binding agent with excellent binding properties. A search of all five loops would therefore result in the identification of loop variant binding agents with very high affinity.

This work has shown that it is possible to engineer a stable monomeric binding agent based on a beta barrel topology so as to produce a binding agent that can be used in immunoassays as a potential antibody replacement. Amino acid changes were incorporated into a basic parental binding agent structure to increase the stability of the molecule and to provide additional functionality. The five target contacting loops selected for binding interactions provide a huge potential for discovering novel binding agents. Theoretically $20^{30}$ different molecules can be produced. This essentially means that this system can be used to generate binding agents against any target molecule or epitope.

A nucleic acid for this new binding agent was designed, synthesized, and was used to produce the binding agent in an *E. coli* expression system. The nucleic acid incorporated novel restriction endonuclease sites in order to generate a loop combinatorial library. Two variants of the binding agent were produced. The first variant was isolated from the combinatorial library and was found to have a loop i sequence that allowed the binding agent to bind trypsin. The second variant contained a novel loop i sequence that was discovered de novo, using a system of automatic and random loop generation and molecular docking. This molecule also bound to trypsin. The binding agent molecules are very stable and functional, hence the binding agent system can be used to create an unlimited number of binding agents and these can be used to replace conventional antibodies in diagnostic tests.

REFERENCES

Arnold, U., and Ulbrich-Hofmann, R. (1997). Kinetic and thermodynamic thermal stabilities of ribonuclease A and ribonuclease B. Biochemistry 36, 2166-2172.

Clark, M., Cramer, R. D., and van Opdensch, N. (1989). J. Computational Chem. 10, 982-986.

Guex, N. and Peitsch, M. C. (1997). Swiss Model and the Swiss-PdbViewer: An environment for comparative protein modeling. Electrophoresis 18, 2714-2723.

Higgins, D. G., Bleasby, A. J., and Fuchs, R. (1992). Clustal V: Improved software for multiple sequence alignment. CABIOS 8, 189-191.

Lakowicz, J. R. (1983). *Principles of Fluorescence Spectroscopy*, Chapter 10, Plenum Press, New York, London.

Muyldermans, S. (2001). Single domain camel antibodies: Current status. Reviews in Molec. Biotech. 74, 277-302.

Pace, C. N., Shirley, B. A., and Thomson, J. A. (1989). In Protein Structure a practical approach (T. E. Creighton, Ed.), pp. 311-330. IRL Press, Oxford, UK.

Peitsch, M. C. (1996). ProMod and Swiss-Model: Internet-based tools for automated comparative protein modeling. Biochem. Soc. Trans. 24:274-279.

Peitsch M C, Herzyk P, Wells T N C and Hubbard R E (1996) Automated modeling of the transmembrane region of G-protein coupled receptor by Swiss-Model. Receptors and Channels 4:161-164.

Sayle, R. A. and Milner-White, E. J. (1995). RasMol: Biomolecular graphics for all. Trends in Biochemical Sciences 20, 374-376.

Siegel, L M., and Monty, K J. (1966). Determination of molecular weights and frictional ratios of proteins in impure systems by the use of gel filtration and density gradient centrifugation. Application to crude preparations of sulfite and hydroxylamine reductases. Biochim. Biophys. Acta 112, 346-362.

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed:

1. A method of making a library of binding agent polypeptides comprising:

generating a collection of random oligonucleotides, each random oligonucleotide comprising a random sequence of from about 6 to about 30 nucleotides (n), wherein n is A, C, G or T;

substituting each random oligonucleotide into a generic binding agent nucleic acid present within an expression vector to generate a library of expression vectors that encode binding agent polypeptides; and placing the library of expression vectors into a population of host cells to generate a library of host cells that express a library of binding agent polypeptides;

wherein the generic binding agent nucleic acid comprises the nucleic acids of SEQ ID NO:1 or the generic binding agent nucleic acid encodes a binding agent polypeptide with a sequence comprising the amino acids 1-26, the amino acids 34-53, the amino acids 59-74, the amino acids 79-101, the amino acids 110-116 and the amino acids 123-134 of SEQ ID NO:2.

2. The method of claim 1, wherein at least one of the collection of random oligonucleotides comprises the random sequence of SEQ ID NO:25, SEQ ID NO:26, SEQ ID NO:27, SEQ ID NO:28 or SEQ ID NO:29.

3. The method of claim 1, wherein the generic binding agent nucleic acid encodes the binding agent polypeptide of SEQ ID NO:4.

4. The method of claim 1, wherein the binding agent polypeptide further has binding loops comprising Xaa amino acids, and wherein the Xaa amino acids are selected from the group consisting of genetically encoded L-amino acids, naturally occurring non-genetically encoded L-amino acids, synthetic L-amino acids and D-enantiomers thereof.

5. The method of claim 4, wherein each Xaa amino acid is exchanged for a specific amino acid and the binding agent polypeptide can bind to a selected target molecule.

* * * * *

SEQUENCE LISTING

```
<160> NUMBER OF SEQ ID NOS: 38

<210> SEQ ID NO 1
<211> LENGTH: 423
<212> TYPE: DNA
<213> ORGANISM: Artificial Sequence
<220> FEATURE:
<223> OTHER INFORMATION: Nucleic acid sequence of a binding agent
<220> FEATURE:
<221> NAME/KEY: misc_feature
<222> LOCATION: (1)...(423)
<223> OTHER INFORMATION: n = a, c, g or t

<400> SEQUENCE: 1
acacaccata tggacgttca gctgcaggct tctggtggtg gttctgttca ggctggtggt      60
tctctgcgtc tgtcttgcgc tgctagcnnn nnnnnnnnnn nnnnnnnntg cgcaggttgg     120
ttccgtcagg ctccgggtaa agaacgtgaa ggtgttgctg ctattaatnn nnnnnnnnnn     180
nnnactagtt acgctgactc tgttaaaggt cgtttcacca tctctcaatt gnnnnnnnnn     240
nnnaacgttt acctgctgat gaactctctg gaaccggaag acaccgctat ctactactgc     300
gctgctggcc acnnnnnnnn nnnnnnnnnn nncacgtgcg gtcacggtct gagtactnnn     360
nnnnnnnnnn nnnnnccatg gggtcagggt acccaggtta ccgtttcttc ttagatatca     420
cac                                                                  423

<210> SEQ ID NO 2
<211> LENGTH: 134
<212> TYPE: PRT
<213> ORGANISM: Artificial Sequence
<220> FEATURE:
<223> OTHER INFORMATION: A binding agent
<220> FEATURE:
<221> NAME/KEY: SITE
<222> LOCATION: (1)...(134)
<223> OTHER INFORMATION: Xaa = any natural or synthetic amino acid

<400> SEQUENCE: 2

Met Asp Val Gln Leu Gln Ala Ser Gly Gly Gly Ser Val Gln Ala Gly
 1               5                  10                  15

Gly Ser Leu Arg Leu Ser Cys Ala Ala Ser Xaa Xaa Xaa Xaa Xaa Xaa
            20                  25                  30

Xaa Cys Ala Gly Trp Phe Arg Asn Ala Pro Gly Lys Glu Arg Glu Gly
        35                  40                  45
```

-continued

```
Val Ala Ala Ile Asn Xaa Xaa Xaa Xaa Xaa Tyr Ser Tyr Ala Asp Ser
 50                  55                  60

Val Lys Gly Arg Phe Thr Ile Ser Gln Leu Xaa Xaa Xaa Asn Val
 65                  70                  75                  80

Tyr Leu Leu Met Asn Ser Leu Glu Pro Glu Asp Thr Ala Ile Tyr Tyr
                 85                  90                  95

Cys Ala Ala Gly His Xaa Xaa Xaa Xaa Xaa Xaa Xaa Cys Gly His
                100                 105                 110

Gly Leu Ser Thr Xaa Xaa Xaa Xaa Xaa Xaa Pro Trp Gly Gln Gly Thr
                115                 120                 125

Gln Val Thr Val Ser Ser
                130
```

<210> SEQ ID NO 3
<211> LENGTH: 423
<212> TYPE: DNA
<213> ORGANISM: Artificial Sequence
<220> FEATURE:
<223> OTHER INFORMATION: The nucleic acid sequence of a generic binding reagent

<400> SEQUENCE: 3

```
acacaccata tggacgttca gctgcaggct tctggtggtg gttctgttca ggctggtggt      60
tctctgcgtc tgtcttgcgc tgctagcgct ggtgctgctg gtgctgcttg cgcaggttgg     120
ttccgtcagg ctccgggtaa agaacgtgaa ggtgttgctg ctattaatgc tggtgctgct     180
ggtactagtt acgctgactc tgttaaaggt cgtttcacca tctctcaatt ggctggtgct     240
gctaacgttt acctgctgat gaactctctg gaaccggaag acaccgctat ctactactgc     300
gctgctggcc acgctggtgc tgctggtgct gccacgtgcg gtcacggtct gagtactgct     360
ggtgctgctg gtgctccatg gggtcagggt acccaggtta ccgtttcttc ttagatatca     420
cac                                                                   423
```

<210> SEQ ID NO 4
<211> LENGTH: 134
<212> TYPE: PRT
<213> ORGANISM: Artificial Sequence
<220> FEATURE:
<223> OTHER INFORMATION: A generic binding reagent

<400> SEQUENCE: 4

```
Met Asp Val Gln Leu Gln Ala Ser Gly Gly Gly Ser Val Gln Ala Gly
  1               5                  10                  15

Gly Ser Leu Arg Leu Ser Cys Ala Ala Ser Ala Gly Ala Ala Gly Ala
                 20                  25                  30

Ala Cys Ala Gly Trp Phe Arg Gln Ala Pro Gly Lys Glu Arg Glu Gly
                 35                  40                  45

Val Ala Ala Ile Asn Ala Gly Ala Gly Thr Ser Tyr Ala Asp Ser
 50                  55                  60

Val Lys Gly Arg Phe Thr Ile Ser Gln Leu Ala Gly Ala Asn Val
 65                  70                  75                  80

Tyr Leu Leu Met Asn Ser Leu Glu Pro Glu Asp Thr Ala Ile Tyr Tyr
                 85                  90                  95

Cys Ala Ala Gly His Ala Gly Ala Ala Gly Ala Ala Thr Cys Gly His
                100                 105                 110

Gly Leu Ser Thr Ala Gly Ala Ala Gly Ala Pro Trp Gly Gln Gly Thr
                115                 120                 125
```

Gln Val Thr Val Ser Ser
    130

<210> SEQ ID NO 5
<211> LENGTH: 40
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 5
acacaccata tggacgttca gctgcaggct tctggtggtg                          40

<210> SEQ ID NO 6
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 6
tgaacagaac caccaccaga agcctgcagc tgaacgtcca tatggtgtgt               50

<210> SEQ ID NO 7
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 7
gttctgttca ggctggtggt tctctgcgtc tgtcttgcgc tgctagcgct               50

<210> SEQ ID NO 8
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 8
cagcagcacc agcgctagca gcgcaagaca gacgcagaga accaccagcc               50

<210> SEQ ID NO 9
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 9
ggtggtgctg ctggtgcttg cgcaggttgg ttccgtcagg ctccgggtaa               50

<210> SEQ ID NO 10
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 10
ttcacgttct ttacccggag cctgacggaa ccaacctgcg caagcagcac          50

<210> SEQ ID NO 11
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 11
agaacgtgaa ggtgttgctg ctattaatgc tggtgctgct ggtactagtt          50

<210> SEQ ID NO 12
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 12
gagtcagcgt aactagtacc agcagcacca gcattaatag cagcaacacc          50

<210> SEQ ID NO 13
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 13
acgctgactc tgttaaaggt cgtttcacca tctctcaatt ggctggtgct          50

<210> SEQ ID NO 14
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 14
aaacgtaaga agcaccagcc aattgagaga tggtgaaacg acctttaaca          50

<210> SEQ ID NO 15
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 15
gctaacgttt acctgctgat gaactctctg gaaccggaag acaccgctat          50

<210> SEQ ID NO 16
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 16
gcagtagtag atagcggtgt cttccggttc cagagagttg atcagcaggt          50

<210> SEQ ID NO 17
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 17
ctactactgc gctgctggcc acgctggtgc tgctggtgct gccacgtgcg           50

<210> SEQ ID NO 18
<211> LENGTH: 50
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 18
agaccgttac cgcacgtggc agcaccagca gcaccagcgt ggccagcagc           50

<210> SEQ ID NO 19
<211> LENGTH: 40
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 19
gtcacggtct gagtactggc tggtgctgct ggtgctcatg                      40

<210> SEQ ID NO 20
<211> LENGTH: 40
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 20
accctgaccc catgagcacc agcagcacca gccagtactc                      40

<210> SEQ ID NO 21
<211> LENGTH: 43
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 21
gggtcagggt acccaggtta ccgtttcttc ttagatatca cac                  43

<210> SEQ ID NO 22
<211> LENGTH: 33
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 22
gtgygatatc taagaagaaa cggtaacctg ggt                             33

```
<210> SEQ ID NO 23
<211> LENGTH: 22
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 23
acacaccata tggacgttca gc                                              22

<210> SEQ ID NO 24
<211> LENGTH: 21
<212> TYPE: DNA
<213> ORGANISM: Artificial Sequence
<220> FEATURE:
<223> OTHER INFORMATION: DNA oligonucleotide used for the generic
      binding agent

<400> SEQUENCE: 24
gtgtgatatc taagaaacgg t                                               21

<210> SEQ ID NO 25
<211> LENGTH: 33
<212> TYPE: DNA
<213> ORGANISM: Artificial Sequence
<220> FEATURE:
<223> OTHER INFORMATION: Sequence of a degenerate loop oligonucleotide
      that was used to produce random libraries of binding agents
<220> FEATURE:
<221> NAME/KEY: misc_feature
<222> LOCATION: (1)...(33)
<223> OTHER INFORMATION: n = a, t, g or c

<400> SEQUENCE: 25
gctagcnnnn nnnnnnnnn nnnnnnntgc gca                                   33

<210> SEQ ID NO 26
<211> LENGTH: 27
<212> TYPE: DNA
<213> ORGANISM: Artificial Sequence
<220> FEATURE:
<223> OTHER INFORMATION: Sequence of a degenerate loop oligonucleotide
      that used to produce random libraries of binding agents
<220> FEATURE:
<221> NAME/KEY: misc_feature
<222> LOCATION: (1)...(27)
<223> OTHER INFORMATION: n = a, g, t or c

<400> SEQUENCE: 26
attaatnnnn nnnnnnnnn nactagt                                          27

<210> SEQ ID NO 27
<211> LENGTH: 24
<212> TYPE: DNA
<213> ORGANISM: Artificial Sequence
<220> FEATURE:
<223> OTHER INFORMATION: Sequence of a degenerate loop oligonucleotide
      that was used to produce random libraries of binding agents
<220> FEATURE:
<221> NAME/KEY: misc_feature
<222> LOCATION: (1)...(24)
<223> OTHER INFORMATION: n = a, t, g or c

<400> SEQUENCE: 27
caattgnnnn nnnnnnnaa cgtt                                             24

<210> SEQ ID NO 28
```

```
<211> LENGTH: 33
<212> TYPE: DNA
<213> ORGANISM: Artificial Sequence
<220> FEATURE:
<223> OTHER INFORMATION: Sequence of a degenerate loop oligonucleotide
      that was used to produce random libraries of binding agents
<220> FEATURE:
<221> NAME/KEY: misc_feature
<222> LOCATION: (1)...(33)
<223> OTHER INFORMATION: n = a, t, g or c

<400> SEQUENCE: 28
tggccannnn nnnnnnnnnn nnnnnnncac gtg                                    33

<210> SEQ ID NO 29
<211> LENGTH: 30
<212> TYPE: DNA
<213> ORGANISM: Artificial Sequence
<220> FEATURE:
<223> OTHER INFORMATION: Sequence of a degenerate loop oligonucleotide
      that was used to produce random libraries of binding agents
<220> FEATURE:
<221> NAME/KEY: misc_feature
<222> LOCATION: (1)...(30)
<223> OTHER INFORMATION: n = a, t, g or c

<400> SEQUENCE: 29
agtactnnnn nnnnnnnnnn nnnnccatgg                                        30

<210> SEQ ID NO 30
<211> LENGTH: 21
<212> TYPE: DNA
<213> ORGANISM: Artificial Sequence
<220> FEATURE:
<223> OTHER INFORMATION: A loop i DNA sequence

<400> SEQUENCE: 30
cgttacctgc gttacccgtc t                                                 21

<210> SEQ ID NO 31
<211> LENGTH: 7
<212> TYPE: PRT
<213> ORGANISM: Artificial Sequence
<220> FEATURE:
<223> OTHER INFORMATION: A loop i amino acid sequence

<400> SEQUENCE: 31

Arg Tyr Leu Arg Tyr Pro Ser
 1               5

<210> SEQ ID NO 32
<211> LENGTH: 7
<212> TYPE: PRT
<213> ORGANISM: Artificial Sequence
<220> FEATURE:
<223> OTHER INFORMATION: A parental binding agent amino acid sequence

<400> SEQUENCE: 32

Ala Gly Ala Ala Gly Ala Ala
 1               5

<210> SEQ ID NO 33
<211> LENGTH: 7
<212> TYPE: PRT
<213> ORGANISM: Artificial Sequence
<220> FEATURE:
<223> OTHER INFORMATION: A loop i sequence generated by molecular
      biology
```

```
<400> SEQUENCE: 33

Arg Tyr Leu Arg Tyr Pro Ser
 1               5

<210> SEQ ID NO 34
<211> LENGTH: 33
<212> TYPE: DNA
<213> ORGANISM: Artificial Sequence
<220> FEATURE:
<223> OTHER INFORMATION: A loop i sequence generated by molecular
      biology

<400> SEQUENCE: 34
gctagccgtt acctgcgtta cccgtcttgc gca                                33

<210> SEQ ID NO 35
<211> LENGTH: 7
<212> TYPE: PRT
<213> ORGANISM: Artificial Sequence
<220> FEATURE:
<223> OTHER INFORMATION: A loop i sequence generated by computer

<400> SEQUENCE: 35

Ile Thr Ala Val Cys His Lys
 1               5

<210> SEQ ID NO 36
<211> LENGTH: 33
<212> TYPE: DNA
<213> ORGANISM: Artificial Sequence
<220> FEATURE:
<223> OTHER INFORMATION: A loop i sequence generated by computer

<400> SEQUENCE: 36
gctagcatca ccgctgtttg ccacaaatgc gca                                33

<210> SEQ ID NO 37
<211> LENGTH: 134
<212> TYPE: PRT
<213> ORGANISM: Artificial Sequence
<220> FEATURE:
<223> OTHER INFORMATION: A variant parental bind agent
<220> FEATURE:
<221> NAME/KEY: SITE
<222> LOCATION: (1)...(134)
<223> OTHER INFORMATION: Xaa = any natural or synthetic amino acid
<220> FEATURE:
<221> NAME/KEY: SITE
<222> LOCATION: 1, 9, 10, 11, 16, 17, 36, 42, 43, 48, 67, 84, 89, 97,
      100, 111, 113, 123, 125, 127
<223> OTHER INFORMATION: Xaa = any apolar amino acid
<220> FEATURE:
<221> NAME/KEY: SITE
<222> LOCATION: 3, 5, 7, 13, 15, 19, 21, 24, 25, 35, 41, 49, 50, 51, 52,
      62, 65, 71, 74, 80, 82, 83, 87, 93, 94, 98, 99, 114, 130, 132
<223> OTHER INFORMATION: Xaa = any aliphatic amino acid
<220> FEATURE:
<221> NAME/KEY: SITE
<222> LOCATION: 4, 6, 8, 12, 14, 18, 22, 26, 40, 53, 59, 60, 61, 64, 70,
      72, 73, 79, 81, 85, 86, 92, 95, 96, 115, 116, 126, 128, 129
<223> OTHER INFORMATION: Xaa = any polar amino acid
<220> FEATURE:
<221> NAME/KEY: SITE
<222> LOCATION: 20, 39, 44, 46, 66, 68, 101, 112
<223> OTHER INFORMATION: Xaa = any basic amino acid
<220> FEATURE:
<221> NAME/KEY: SITE
<222> LOCATION: (37)...(38)
<223> OTHER INFORMATION: Xaa = any aromatic amino acid
<220> FEATURE:
<221> NAME/KEY: SITE
```

```
<222> LOCATION: (90)...(91)
<223> OTHER INFORMATION: Xaa = any acidic amino acid
<220> FEATURE:
<221> NAME/KEY: SITE
<222> LOCATION: (2)...(2)
<223> OTHER INFORMATION: Xaa = any acidic amino acid
<220> FEATURE:
<221> NAME/KEY: SITE
<222> LOCATION: (45)...(45)
<223> OTHER INFORMATION: Xaa = any acidic amino acid
<220> FEATURE:
<221> NAME/KEY: SITE
<222> LOCATION: (47)...(47)
<223> OTHER INFORMATION: Xaa = any acidic amino acid
<220> FEATURE:
<221> NAME/KEY: SITE
<222> LOCATION: (63)...(63)
<223> OTHER INFORMATION: Xaa = any acidic amino acid
<220> FEATURE:
<221> NAME/KEY: SITE
<222> LOCATION: (88)...(88)
<223> OTHER INFORMATION: Xaa = any acidic amino acid
<220> FEATURE:
<221> NAME/KEY: SITE
<222> LOCATION: (131)...(131)
<223> OTHER INFORMATION: Xaa = any polar amino acid
<220> FEATURE:
<221> NAME/KEY: SITE
<222> LOCATION: (133)...(133)
<223> OTHER INFORMATION: Xaa = any polar amino acid
<220> FEATURE:
<221> NAME/KEY: SITE
<222> LOCATION: (134)...(134)
<223> OTHER INFORMATION: Xaa = any polar amino acid
<220> FEATURE:
<221> NAME/KEY: SITE
<222> LOCATION: (69)...(69)
<223> OTHER INFORMATION: Xaa = any aromatic amino acid
<220> FEATURE:
<221> NAME/KEY: SITE
<222> LOCATION: (124)...(124)
<223> OTHER INFORMATION: Xaa = any aromatic amino acid
<220> FEATURE:
<221> NAME/KEY: SITE
<222> LOCATION: (23)...(23)
<223> OTHER INFORMATION: Xaa = any cysteine-like amino acid
<220> FEATURE:
<221> NAME/KEY: SITE
<222> LOCATION: (97)...(97)
<223> OTHER INFORMATION: Xaa = any cysteine-like amino acid
<220> FEATURE:
<221> NAME/KEY: SITE
<222> LOCATION: (34)...(34)
<223> OTHER INFORMATION: Xaa = any cysteine-like amino acid
<220> FEATURE:
<221> NAME/KEY: SITE
<222> LOCATION: (110)...(110)
<223> OTHER INFORMATION: Xaa = any cysteine-like amino acid

<400> SEQUENCE: 37

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95
```

-continued

```
Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa
    130

<210> SEQ ID NO 38
<211> LENGTH: 132
<212> TYPE: PRT
<213> ORGANISM: Artificial Sequence
<220> FEATURE:
<223> OTHER INFORMATION: A generic binding agent

<400> SEQUENCE: 38

Val Gln Leu Gln Ala Ser Gly Gly Gly Ser Val Gln Ala Gly Gly Ser
 1               5                  10                  15

Leu Arg Leu Ser Cys Ala Ala Ser Ala Gly Ala Ala Gly Ala Ala Cys
            20                  25                  30

Ala Gly Trp Phe Arg Gln Ala Pro Gly Lys Glu Arg Glu Gly Val Ala
        35                  40                  45

Ala Ile Asn Ala Gly Ala Ala Gly Thr Ser Tyr Ala Asp Ser Val Lys
 50                  55                  60

Gly Arg Phe Thr Ile Ser Gln Leu Ala Gly Ala Ala Asn Val Tyr Leu
65                  70                  75                  80

Leu Met Asn Ser Leu Glu Pro Glu Asp Thr Ala Ile Tyr Tyr Cys Ala
            85                  90                  95

Ala Gly His Ala Gly Ala Ala Gly Ala Ala Thr Cys Gly His Gly Leu
            100                 105                 110

Ser Thr Ala Gly Ala Ala Gly Ala Pro Trp Gly Gln Gly Thr Gln Val
        115                 120                 125

Thr Val Ser Ser
    130
```